(12) United States Patent
Hinuma et al.

(10) Patent No.: US 6,399,325 B1
(45) Date of Patent: Jun. 4, 2002

(54) DNA ENCODING A GALANIN RECEPTOR

(75) Inventors: Shuji Hinuma; Ryo Fujii; Shoji Fukusumi; Tetsuya Ohtaki, all of Tsukuba; Masaki Hosoya, Tsuchiura; Kazuhiro Ohgi, Tsukuba; Haruo Onda, Tsuchiura, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 08/540,650

(22) Filed: Oct. 11, 1995

(30) Foreign Application Priority Data

Oct. 13, 1994 (JP) .............................................. 6-247599
Dec. 28, 1994 (JP) .............................................. 6-326610
May 31, 1995 (JP) .............................................. 7-134412

(51) Int. Cl.$^7$ .................. C12N 15/12; C12N 15/63; C12N 5/10; C07K 14/705
(52) U.S. Cl. .................. 435/69.1; 435/320.1; 435/325; 530/350; 536/23.5
(58) Field of Search .................. 536/23.5; 435/69.1, 435/7.2, 240.1, 320.1, 325; 530/350, 395

(56) References Cited

U.S. PATENT DOCUMENTS 5,436,155 A * 7/1995 Bell et al. ................. 435/252.3

FOREIGN PATENT DOCUMENTS

| FR | A 2716205 | 8/1995 |
| WO | WO 9522608 A | 8/1995 |
| WO | WO 9605302 A | 2/1996 |

OTHER PUBLICATIONS

Habert–Ortoli, et al., *Proc. Natl. Acad. Sci. USA*, vol. 91, pp. 9780–9783 (1994).
Heuillet, et al., *European Journal of Pharmacology Molecular Pharmacology Section 269*, pp. 139–147 (1994).

\* cited by examiner

*Primary Examiner*—Michael Pak
(74) *Attorney, Agent, or Firm*—David G. Conlin; Edwards & Angell, LLP

(57) ABSTRACT

Galanin receptor proteins, production and use thereof including screening of galanin receptor agonists and antagonists are provided. Galanin receptor proteins, etc. or salts thereof, partial peptides thereof, DNAs coding for the above galanin receptor protein, processes for producing the above receptor protein, methods of screening for a galanin receptor agonist and/or antagonist or screening kits therefor, agonist and/or antagonist compounds or salts thereof obtained by the above screening method or the screening kit, pharmaceutical compositions containing the above compound or its salt, and antibodies against the above receptor protein are provided. It is allowable to efficiently screen a galanin receptor agonist or antagonist by using the galanin receptor protein, the partial peptide thereof, the galanin receptor protein-encoding DNA, the receptor protein-containing cell or its membrane fraction. The pharmaceuticals thus screened or characterized permits various applications including prophylactic and/or therapeutic treatments against a variety of diseases, e.g., stomach ulcer, diabetes, Alzheimer's disease, dementia, etc. and a sedative.

14 Claims, 27 Drawing Sheets

FIG. 1

| FIG. 1A |
|---------|
| FIG. 1B |

5'

```
         10              19              28              37              46        55
GTG GGC  CTG GTG GGC    AAC TTC CTG    GCC GCG ATG    TCT GTG GAT    CGC TAC GTG GCC
--- ---  --- --- ---    --- --- ---    --- --- ---    --- --- ---    --- --- --- ---
Val Gly  Leu Val Gly    Asn Phe Leu    Ala Ala Met    Ser Val Asp    Arg Tyr Val Ala 64              73              82              91              100       109
ATT GTG  CAC TCG CGG    CGC TCC TCC    CTC AGG GTG    TCC CGC AAC    GCA CTG CTG
--- ---  --- --- ---    --- --- ---    --- --- ---    --- --- ---    --- --- ---
Ile Val  His Ser Arg    Arg Ser Ser    Leu Arg Val    Ser Arg Asn    Ala Leu Leu 118             127             136             145             154       163
GGC GTG  GGC TTC ATC    TGG GCG CTG    TCC ATC GCC    ATG GCC TCG    CCG GTG GCC TAC
--- ---  --- --- ---    --- --- ---    --- --- ---    --- --- ---    --- --- --- ---
Gly Val  Gly Phe Ile    Trp Ala Leu    Ser Ile Ala    Met Ala Ser    Pro Val Ala Tyr 172             181             190             199             208       217
CAC CAG  CGT CTT TTC    CAT CGG GAC    AGC AAC CAG    ACC TTC TGC    TGG GAG CAG TGG
--- ---  --- --- ---    --- --- ---    --- --- ---    --- --- ---    --- --- --- ---
His Gln  Arg Leu Phe    His Arg Asp    Ser Asn Gln    Thr Phe Cys    Trp Glu Gln Trp
```

FIG. 1A

```
                226             235             244             253             262             271
       CCC AAG CTC CAC AAG AAG GCT TAC GTG GTG TGC ACT TTC GTC TTT GGG TAC
       --- --- --- --- --- --- --- --- --- --- --- --- --- --- --- --- ---
       Pro Asn Lys Leu His Lys Lys Ala Tyr Val Val Cys Thr Phe Val Phe Gly Tyr
                280             289             298             307             316             325
       CTT CTG CCC TTA CTG CTC ATC TGC TTT TGC TAT GCC AAG GTC CTT AAT CAT CTG
       --- --- --- --- --- --- --- --- --- --- --- --- --- --- --- --- --- ---
       Leu Leu Pro Leu Leu Leu Ile Cys Phe Cys Tyr Ala Lys Val Leu Asn His Leu
                334             343             352             361             370             379
       CAT AAA CTG AAA AAC ATG TCA AAA AAG TCT GAA GCA TCC AAG AAA AAG ACT
       --- --- --- --- --- --- --- --- --- --- --- --- --- --- --- --- ---
       His Lys Leu Lys Asn Met Ser Lys Lys Ser Glu Ala Ser Lys Lys Lys Thr
                388             397             406             415             424             433
       GCA CAG ACC GTC CTG GTC GTT GTA GTA TTT GCC CTC TGC TGG CTG CCT TTC
       --- --- --- --- --- --- --- --- --- --- --- --- --- --- --- --- ---
       Ala Gln Thr Val Leu Val Val Val Val Phe Ala Leu Cys Trp Leu Pro Phe

TAC 3'
       ---
       Tyr
```

FIG. 1B

| SEQ ID NO: | | | | | | | 50 |
|---|---|---|---|---|---|---|---|
| 12 | p3H2-34 | 1 | VGLVGNELAA | MSVDRYVALIV | HSRRSSSIRV | SRNFLIGVGF | IWALSIAMAS 50 |
| 13 | JN0605 | 1 | MFTSVFCLTV | LSVDRYVALIV | HPLRAATYRR | PSVAKLINIG | VWLASLLVTL 50 |
| 14 | B41795 | 1 | QFTSIFCLTV | MSIDRVLAVV | HPIKSAKWRR | PRITAKMITMA | VWGVSLLIVI 50 |
| 15 | A39297 | 1 | MFTSIYCLTV | LSVDRYVAVV | HPIKAARYRR | PTIVAKVVNLG | VWVLSLLIVII 50 |
| | p3H2-34 | 51 | PMA-YHQRLF | HRDSNQTFCW | EQWPNKLHK- | -KAVVVCTFV | FGVLLPLILI 100 |
| | JN0605 | 51 | PIAIFADTRP | ABGGQAVACN | LQWPHPAWS- | -AVFVVYTFI | LGFLLPVLAI 100 |
| | B41795 | 51 | PIMIYAGLRS | NQWGRSS-CT | INWPGESGAW | YTGFLIYTFI | LGFLVPIITI 100 |
| | A39297 | 51 | PIVVESRITAA | NSIDGTVA-CN | MLMPEPAQRW | LVGFVILYTFI | MGFLLPVGAI 100 |
| | p3H2-34 | 101 | CFCY---AK | VLNHLHKKLK | NMSKKSEASK | KKTAQTVLVV | VVVFALCWLP 150 |
| | JN0605 | 101 | CLCYLLIVGK | MRAVALRAGW | QQRRRSE--- | KKITRLVLMV | VVVFVLCWLP 150 |
| | B41795 | 101 | CLCYLFIIIK | VKSSGTRVGS | SKRKKSE--- | KKVTRMVSIV | VAVFLFCWLP 150 |
| | A39297 | 101 | CLCYMLIIAK | MRMWAIKAGW | QQRRKSE--- | RKITIMVMMV | MVFVICWMP 150 |
| | p3H2-34 | 151 | FY. | . . . . . . . . . . | . . . . . . . . . . | . . . . . . . . . . | . . . . . . . . . . 200 |
| | JN0605 | 151 | FY. | . . . . . . . . . . | . . . . . . . . . . | . . . . . . . . . . | . . . . . . . . . . 200 |
| | B41795 | 151 | FY. | . . . . . . . . . . | . . . . . . . . . . | . . . . . . . . . . | . . . . . . . . . . 200 |
| | A39297 | 151 | FY. | . . . . . . . . . . | . . . . . . . . . . | . . . . . . . . . . | . . . . . . . . . . 200 |

FIG. 3

```
  1  CAAAGCAACAGGTGCAACCTCAAGGCACTGAAAGCAAGGGACGCAGCTCACAAGGGCCAAGGGATTGAACC    72
  1
 73  CATAACCGCTCAGAAGATTCTCGCCTGCCGGAGAGCTGCGAGGAGTCCCACCGTCCAGCTTGCTGACTGC   144
  1
145  GAGCAGTGAGAGTCGCCTAGACCCGTACCTCTGTGTTCTCGGAGCCTGCGCCCCCGCACGGGAAAGGCTTAG  216
  1
217  CTCGGGACTTGCAGCACCGCCCTCCTCTTTAGCCAGGCCAGGCACGGAGGATAGTGTGATCGGGCACAGCCAGG  288
  1
289  GTCGCTCTTCCAGGCTTTCTTGCGGGTTGCCGGAGGTACTAGTTGGAGACGCGCCGCTCTCCGCGCT  360
  1
```

FIG. 4A

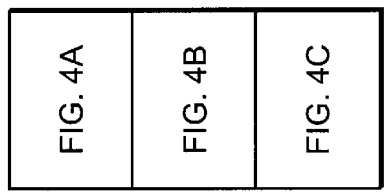

FIG. 4

```
361 CTGTCCTGGGCCACTCCGTGATCCTAGGCTACTTCCAGAGCCAGTTTCCCTGCTGGCACAACTCTCCAGG                                                                        432
  1                                                                                                                                                1

433 GCGCTCCGTCGTTGCACAGCCCCCAAGGGGTATCCCAGTAAGTGATGGAACTGGCTATGTGAACCTC                                                                           504
  1                                                                   MetGluLeuAlaMetValAsnLeu                                                      8

505 AGTGAAGGGAATGGGAGCGACCCAGAGCCCAGCCCTCTTCGGCATTGGCGTGGAG                                                                                       576
  8 SerGluGlyAsnGlySerAspProGluProAlaProProAlaProGluSerArgProLeuArgHisTrpArgGlyValGlu                                                              32

577 AACTTCATTACGCTGGTAGTGTTTGGCCTGATTTTCGGATGGCGTGGCAACAGCCTGGTGATCACC                                                                            648
 32 AsnPheIleThrLeuValValPheGlyLeuIleLeuPheAlaMetGlyLeuIleLysGlyLeuValLeuGlyAsnSerLeuValIleThr                                                     56

649 GTGCTGGCGCAGCAAACCAGGAGCAAGCACCACCAACCTGTTATCCTCAATCTGAGCATGCA                                                                               720
 56 ValLeuAlaArgSerLysLysProGlyLysProArgSerThrThrAsnLeuPheIleLeuAsnLeuSerIleAla                                                                    80

721 GACCTGGCCTACCTGCAAGTTATACACTACTTCTGCATCCCTTTTCAGGCGCAGGCGCAGATCGAGGCGCACCTGGGTGCTGGGC                                                        792
 80 AspLeuAlaTyrLeuLeuPheCysIleProPheGlnAlaThrValTyrAlaLeuProThrTrpValLeuGly                                                                      104

793 GCCTTCATCTGCAAGTTCATACACTACTTCTGCATCCGTCCATGTCGTGAGCATCTTCACCCTGGCCCGCCG                                                                     864
104 AlaPheIleCysLysPheIleHisTyrPhePheThrThrValSerMetLeuValSerIlePheThrLeuAlaAla                                                                   128

865 ATGTCTGTGGATGCTACTGTGGCCATTGTGCACTGTGGGTATGCACTGTCGGCGCGTCACGGTGTCCGCAACGCA                                                                 936
128 MetSerValAspArgTyrValAlaIleValHisSerArgArgArgSerArgValSerArgValSerArgAsnAla                                                                  152

937 CTGCTGGGGCTTCATCTGGGCGCTGTCCATGCCGGCGCCTCCACCGTCTT                                                                                           1008
152 LeuLeuGlyValGlyPheIleTrpAlaLeuSerIleAlaMetAlaSerProValAlaTyrHisGlnArgLeu                                                                     176
```

FIG. 4B

```
1009  TTCCATGGGACAGCAACCAGACCTTCTGCTGGGAGCAGTGGCCCAACAGCTCCACAAGAAGCTTACGTG    1080
 176  PheHisArgAspSerAsnGlnThrPheCysTrpGluGlnTrpProAsnLysLeuHisLysLysAlaTyrVal  200

1081  GTGTGCACTTTCGTCTTTGGTACTTCTGCCTTTGCTCATCTGCCCTTACTGCTCTTGCCCTTAATGCCAAGGTCCTTAAT    1152
 200  ValCysThrPheValPheGlyTyrLeuLeuLeuIleCysPheCysTyrAlaLysValLeuAsn           224

1153  CATCTGCATAAAAGTCTGAAAAAGTCTGAAGCATCAAGAAAAGACTGCACAGACCGTC              1224
 224  HisLeuHisLysSerLeuLysLysSerGluAlaSerLysLysLysThrAlaGlnThrVal             248

1225  CTGGTGGTCGTGTAGTATTGCATATCCTGCCCCATCATGTCGTCCACCTCTGGGCTGAGTTTGGA        1296
 248  LeuValValValValHisIleSerTrpLeuProHisValValHisLeuTrpAlaGluPheGly          272

1297  GCCTTCCCACTGACGCCAGTTCTTCTTCTCAGAATCACCGCCATGCCTGGCATACACCTCCTCA         1368
 272  AlaPheProLeuThrProAlaSerPhePheArgIleThrAlaHisCysLeuAlaTyrSerAsnSerSer    296

1369  GTGAACCCCATCATATATGCCTTTCTCAGAAAACTCCGAAGGCGTACAAGCAAGTGTTCAAGTGTCAT     1440
 296  ValAsnProIleIleTyrAlaPheLeuSerGluAsnPheArgLysAlaTyrLysGlnValPheLysCysHis  320

1441  GTTTGGCGATGAATCTCCACGCAGTGAAACTAAGGAAAACAGAGCCGATGGACACCCGCCATCCACCAAC   1512
 320  ValCysAspGluSerProArgSerGluThrLysGluAsnLysSerArgMetAspThrProProSerThrAsn 344

1513  TGCACCCACGGTGAAGGTTTGCGGGAGCCCTCCCGACTTCCAGTCTCCCATGTGTGTTAGAGAGGAGGGCG  1584
 344  CysThrHisVal***                                                           349

1585  GAGCGAATTATCAAGTAACATGG                                                   1607
 349                                                                            349
```

FIG. 4C

SEQ ID NO:

```
                  1                                                               50
  2  MOUSEGALRECE   MELAMVNLSE GNGSDPEPPA PESRPLFGIG VENFITLVVF GLIFAMGVLG   50
  5  HUMGALAMI      MELAVGNLSE GNASCPEPPA PEPGPLFGIG VENEVTLVVE GLIFALGVLG   50

51                                                             100
  2  MOUSEGALRECE   NSLVITVLAR SKPGKPRSTT NLFILNLSIA IHYFFTVSML DLAYLLFCIP  100
  5  HUMGALAMI      NSLVITVLAR SKPGKPRSTT NLFILNLSIA IHYFFTVSML DLAYLLFCIP  100

101                                                             150
  2  MOUSEGALRECE   WVLGAFICKE IHYFFTVSML VSIFTLAAMS VDRYAIVHS RRSSSLRVSR   150
  5  HUMGALAMI      WVLGAFICKE IHYFFTVSML VSIFTLAAMS VDRYAIVHS RRSSSLRVSR   150

151                                                             200
  2  MOUSEGALRECE   NALLGVGFIW ALSIAMASPV AYHQRLFHR DSNQTFCWEQ WPNKLHKKAY  200
  5  HUMGALAMI      NALLGVGCIW ALSIAMASPV AYHQGLFHPR ASNQTFCWEQ WPQPRHKKAY  200

201                                                             250
  2  MOUSEGALRECE   VVCTFVFGYL LPLLLICFCY AKVLNHLHKK LKNMSKKSEA SKKKTAQTVL  250
  5  HUMGALAMI      VVCTFVFGYL LPLLLICFCY AKVLNHLHKK LKNMSKKSEA SKKKTAQTVL  250

251                                                             300
  2  MOUSEGALRECE   VVVVVFGISW LPHHVVHLWA AYHQGLFHR SFIFRITAHC LAYSNSSVNP  300
  5  HUMGALAMI      VVVVVFGISW LPHHIIHLWA EFGWFPLTPA SFIFRITAHC LAYSNSSVNP  300

301                                                             350
  2  MOUSEGALRECE   IIYAFLSENF RKAYKQVFKC HVCDESPRSE FRITAHC TKENKSRMDT PPSTNCTHVX  350
  5  HUMGALAMI      IIYAFLSENF RKAYKQVFKC HIRKDSHISD FRITAHC TKENKSRHDT PPSTNCTHVX  350

351                                                             400
  2  MOUSEGALRECE   X . . . . . . . . .                                          400
  5  HUMGALAMI      . . . . . . . . . .                                          400
```

FIG. 6

| FIG. 11A |
| FIG. 11B |
| FIG. 11C |

FIG. 11

1   CGCGGATTTCCAGCCGAGCTGTGTTTCGCCCTCTCAGTTGCAGCAGAGAAGCCCCTGGCACCC   60
1                                                                   1
61  GACTCTATCCACCACCAGGAAGCCTCCCAAAAGAGCTCTCGCCCTGTGGACGACTCGGAA   120
1                                                                   1
121 TCCCTGGAAAAGCCGGGAGTCGAGGCGCCCAGCCCACTGGGGAGGTGGCGCTGGGC       180
1                                                                   1

FIG. 11A

```
181 GCGCGGGATGCGGCGGGGAGCCTTCTCTGCAGGAGCCCACAGTGCACTGTCGCGCTGG    240
181
241 GCAGTGCGGGGAAGCGCCGCGGAAGGAGCGCTCCGAGCAACAGGTGCAGCACGCCAGCC    300
241
301 GCTCCGGGAGCCAGGGAAAACCGCCGGGAAGATCTGGACGGTAAGCGGAGAGAAGGG    360
301
361 TCTTTCCACCTGCGCGGCTGCAGCCCTCTTCCCAGGCTCCGTGGTCGCGCA          420
361
421 GCGGGCGGAGGCCCCCGGGACCCCAGTGCTCTCGAGATCACCGTCCCTTCCCG        480
421
481 AGAAGGTCCAGCTCCGGAACCCTCTCTCAGAAGGTCGGGCGCAAAGAC            540
481
541 GGTGCCACCAGGCACGGATCCCCGGCTCCCGGCTCCCGGGGAAGC              600
541
601 TCAGACTCCTAAACTCGCACTCCGTGCTTGCGGACCCCTGGCCACCCCGGCG         660
601
661 CCTGCTATCCCGGCCCTCCCGCCCCCGGGCCCCGGGCGGACAGCCCCGGGC          720
661
```

FIG. 11B

```
 721 CATG GAG CTG GCG GTC GGG AAC CTC AGC GAG GGC AAC GCG AGC TGG  766
   1 Met Glu Leu Ala Val Gly Asn Leu Ser Glu Gly Asn Ala Ser Trp   15

767 CCG CAC CCC CCC CCC GAC CCG GGG CCG CTG CCC GAG GGC ATC GGC  811
  15 Pro His Pro Pro Pro Asp Pro Gly Pro Leu Pro Glu Gly Ile Gly   30

812 GTG GAG AAC TTC GTG ACG TTC GTG GTG CTG GTG TTC GCG  856
  30 Val Glu Asn Phe Val Thr Phe Val Val Leu Val Phe Ala   45

857 CTG GGC GTG GGC AAC GTG CTA GTG ATC ACC GTG CTG CTC  901
  45 Leu Gly Val Gly Asn Val Leu Val Ile Thr Val Leu Ala Arg  60

902 AGC AAG CCG GGC AAG CCG CGG AGC ACC AAC AAC TTC ATC CTC  946
  60 Ser Lys Pro Gly Lys Pro Arg Ser Thr Asn Leu Phe Ile Leu   75

947 AAC CTG AGC ATC GCC GAC CTG CTG TAC CTC TTC TGC ATC CCC  991
  75 Asn Leu Ser Ile Ala Asp Leu Ala Tyr Leu Leu Phe Cys Ile Pro  90

992 TTC CAG GCC ACC GTG TAC CTG CTG CCC ACC TGG GTG CTG GGC GCC  1036
  90 Phe Gln Ala Thr Val Tyr Ala Leu Pro Thr Trp Val Leu Gly Ala  105

1037 TTC ATC TGC AAG TTC ATC CAC TAC TTC TTC ACC GTG TCC ATG CTG  1081
 105 Phe Ile Cys Lys Phe Ile His Tyr Phe Phe Thr Val Ser Met Leu  120

1082 GTG AGC ATC TTC ACC CTG GCC GCC ATG TCC GTG GAC CGC TAC GTG  1126
 120 Val Ser Ile Phe Thr Leu Ala Ala Met Ser Val Asp Arg Tyr Val  135
```

FIG. 11C

```
1127  GCC ATC GTG CAC TCG CGG CGC TCC TCC CTC AGG GTG TCC CGC  1171
 135  Ala Ile Val His Ser Arg Arg Ser Ser Leu Arg Val Ser Arg   150

1172  AAC GCG CTG CTG GGC GTG GGC TGC ATC TGG GCG CTG TCC ATT GCC  1216
 150  Asn Ala Leu Leu Gly Val Gly Cys Ile Trp Ala Leu Ser Ile Ala   165

1217  ATG GCC TCG CCC GTG GCC TAC CAC CAG GGC CTC TTC CAC CCG CGC  1261
 165  Met Ala Ser Pro Val Ala Tyr His Gln Gly Leu Phe His Pro Arg   180
```

| | | | | | | | | | | |
|---|---|---|---|---|---|---|---|---|---|---|
| 1262 | GCC | AGC | AAC | CAG | ACC | TTC | TGC | TGG | GAG | CAG | 1306 |
| 180 | Ala | Ser | Asn | Gln | Thr | Phe | Cys | Trp | Glu | Gln | 195 |
| 1307 | CAC | AAG | AAG | GCC | TAC | GTG | TGC | GTG | TTC | ACC | 1351 |
| 195 | His | Lys | Lys | Ala | Tyr | Val | Cys | Val | Phe | Thr | 210 |
| 1352 | CTG | CCG | CTC | CTC | ATC | TGC | TTC | TGC | TAT | GCC | 1396 |
| 210 | Leu | Pro | Leu | Leu | Ile | Cys | Phe | Cys | Tyr | Ala | 225 |
| 1397 | CAC | TTG | CAT | AAA | AAG | TTG | AAG | AAC | ATG | TCA | 1441 |
| 225 | His | Leu | His | Lys | Lys | Leu | Lys | Asn | Met | Ser | 240 |
| 1442 | TCC | AAG | AAA | AAG | ACT | GCA | CAG | ACA | GTT | CTG | 1486 |
| 240 | Ser | Lys | Lys | Lys | Thr | Ala | Gln | Thr | Val | Leu | 255 |
| 1487 | TTT | GGA | ATC | TCC | TGG | CTG | CCG | CAC | CAC | ATC | 1531 |
| 255 | Phe | Gly | Ile | Ser | Trp | Leu | Pro | His | His | Ile | 270 |
| 1532 | GAG | TTT | GGA | GTT | TTC | CCG | CTG | ACG | CCG | GCT | 1576 |
| 270 | Glu | Phe | Gly | Val | Phe | Pro | Leu | Thr | Pro | Ala | 285 |

| | | | | | | | | | |
|---|---|---|---|---|---|---|---|---|---|
| CAG | TGG | CCC | GAC | CCT | CGC | | | | 1306 |
| Gln | Trp | Pro | Asp | Pro | Arg | | | | 195 |
| TTC | GTC | TTC | GGC | TAC | CTG | | | | 1351 |
| Phe | Val | Phe | Gly | Tyr | Leu | | | | 210 |
| TAT | GCC | AAG | GTC | CTT | AAT | | | | 1396 |
| Tyr | Ala | Lys | Val | Leu | Asn | | | | 225 |
| TCA | AAG | AAG | TCT | GAA | GCA | | | | 1441 |
| Ser | Lys | Lys | Ser | Glu | Ala | | | | 240 |
| CTG | GTG | GTG | GTT | GTG | GTG | | | | 1486 |
| Val | Val | Val | Val | Val | Val | | | | 255 |
| ATC | ATC | CAT | CTC | TGG | GCT | | | | 1531 |
| Ile | Ile | His | Leu | Trp | Ala | | | | 270 |
| TCC | TTC | CTC | TTC | AGA | | | | | 1576 |
| Ser | Phe | Leu | Phe | Arg | | | | | 285 |

FIG. 12B

```
1577  ATC ACC GCC CAC TGC CTG GCG TAC AGC AAT TCC TCC GTG AAT CCT  1621
 285  Ile Thr Ala His Cys Leu Ala Tyr Ser Asn Ser Ser Val Asn Pro   300

1622  ATC ATT TAT GCA TTT CTC TCT GAA AAT TTC AGG AAG GCC TAT AAA  1666
 300  Ile Ile Tyr Ala Phe Leu Ser Glu Asn Phe Arg Lys Ala Tyr Lys   315

1667  CAA GTG TTC AAG TGT CAC ATT CGC AAA GAT TCA CAC CTG AGT GAT  1711
 315  Gln Val Phe Lys Cys His Ile Arg Lys Asp Ser His Leu Ser Asp   330

1712  ACT AAA GAA AAT AAA AGT CGA ATA GAC ACC CCA TCA ACC AAT      1756
 330  Thr Lys Glu Asn Lys Ser Arg Ile Asp Thr Pro Ser Thr Asn       345

1757  TGT ACT CAT GTG TGA TAA AAGATAGAGTATCCTTATGGTTGAGTTTCCATATA  1809
 345  Cys Thr His Val ***  ***                                      351

1810  AGTGGACCAGACACAGAAACAAACAGAATGAGCTAGTAAGCGATGCTGCAACTTGTTATC 1869
 351                                                                351

1870  TTAACAAGAATTC                                                 1882
 351                                                                351
```

FIG. 12C

```
                     10           20           30           40            50
SEQ 2  m  MELAMVNLSE GNGSDPEPPA PESRPLFGIG VEN FITLVVF GLIFAMGVLG
                                                    (I)
SEQ 5  h  MELAVGNLSE GNASCPEPPA PEPGPLFGIG VEN FVTLVVF GLIFALGVLG 60           70           80           90            100
       m  NSLVITVLAR SKPGKPRSTT N FILNLSIA DLAYLLFCIP FQATVYALPT
                                  (II)
       h  NSLVITVLAR SKPGKPRSTT N FILNLSIA DLAYLLFCIP FQATVYALPT
```

FIG. 16A

| FIG. 16A |
|----------|
| FIG. 16B |

FIG. 16

```
     110 (III)    120          130          140          150
m  WVLGAFICKF IHYFFTVSML VSIFTLAAMS VDRYVAIVHS RRSSSLRVSR
   :::::::::: :::::::::: :::::::::: ::::::::::  :::::::::
h  WVLGAFICKF IHYFFTVSML VSIFTLAAMS VDRYVAIVHS RRSSSLRVSR (IV) 160        170          180          190          200
m  NALLGVGFIW ALSIAMASPV AYHQRLFH-R DSNQTFCWEQ WPNKLHKKAY
   :: :::: :: :::::::::: ::::  :: : :: ::::::: ::: :::::
h  NALLGVGCIW ALSIAMASPV AYHQGLFHPR ASNQTFCWEQ WPDPRHKKAY (V) 210         220          230          240     (VI) 250
m  VVCTFVFGYL LPLLLICFCY AKVLNHLHKK LKNMSKKSEA SKKKTAQTVL
   :::::::::: :::::::::: :::::::::: :::::::::: ::::::::::
h  VVCTFVFGYL LPLLLICFCY AKVLNHLHKK LKNMSKKSEA SKKKTAQTVL 260          270          280 (VII)     290          300
m  VVVVVFGISW LPHHVVHLWA EFGAFPLTPA SFFFRITAHC LAYSNSSVNP
   ::::::::: :::: :: ::: :::: :::: : : ::: ::: ::::::::::
h  VVVVVFGISW LPHHIIHLWA EFGVFPLTPA SFLFRITAHC LAYSNSSVNP 310          320          330          340          350
m  IIYAFLSENF RKAYKQVFKC HVCDESPRSE TKENKSRMDT PPSTNCTHV
   ::::::::::  ::::::::: :  :::: :: ::::::: :: :::::::::
h  IIYAFLSENF RKAYKQVFKC HIRKDSHLSD TKENKSRIDT PPSTNCTHV
```

FIG. 16B

DNA ENCODING A GALANIN RECEPTOR

FIELD OF THE INVENTION

The present invention relates to novel galanin receptor proteins and partial peptides thereof; novel DNAs containing a galanin receptor protein or partial peptide-encoding DNA; processes for producing said galanin receptor protein (or partial peptide); use of said receptor protein (or partial peptide) and said protein (or partial peptide)-encoding DNA; a method of measuring the physiological actions of galanin using a galanin receptor protein-expressing cell or the galanin receptor protein; a method of screening galanin receptor agonists/antagonists using the galanin receptor protein-expressing cell or galanin receptor protein; a kit for said screening; an agonist or antagonist obtained by said screening method; and a pharmaceutical composition containing said agonist or antagonist.

The present invention also relates to a novel mouse pancreatic β cell line MIN6-derived galanin receptor protein and a partial peptide thereof; a novel DNA coding for said mouse galanin receptor protein or its partial peptide; processes for producing said mouse galanin receptor protein or its partial peptide; use of said mouse galanin receptor protein and said protein or peptide-encoding DNA; a method of measuring the physiological actions of galanin using a mouse-derived cell line MIN6 or the mouse galanin receptor protein; and a method of screening a galanin receptor agonist/antagonist using said mouse-derived cell line MIN6 or the receptor protein.

The present invention also relates to a novel human galanin receptor protein; a partial peptide of the human galanin receptor protein; a novel DNA which codes for the galanin receptor protein or partial peptide; a vector carrying said DNA; a transformant harboring said vector; a process for producing the human galanin receptor protein (or its partial peptide); a method of screening a galanin receptor agonist/antagonist using the human galanin receptor protein or a human galanin receptor protein-expressing cell (including the transformant); a kit for said screening; an agonist or an antagonist, obtained by said screening method; and a pharmaceutical composition containing said agonist or antagonist.

BACKGROUND OF THE INVENTION

A variety of hormones, neurotransmitters and the like control, regulate or adjust the functions of living bodies via specific receptors located in cell membranes. Many of these receptors mediate the transmission of intracellular signals via activation of a guanine nucleotide-binding protein (hereinafter, sometimes referred to as "G protein") with which the receptor is coupled and possess the common (homologous) structure, i.e. seven transmembranes (membrane-spanning regions (domains)). Therefore, such a receptor is generically referred to as "G protein coupled receptor" or "seven transmembrane (membrane-spanning) receptor".

G protein coupled receptor proteins which are widely distributed in the functional cellular surface of cells and organs in the living bodies have a very important role as targets for molecules such as hormones, neurotransmitters and physiologically active substances, which molecules control, regulate or adjust the functions of living bodies.

The pancreas plays an important role of carrying out the carbohydrate metabolism by secreting not only a digestive fluid but also glucagon and insulin. Insulin is secreted from the β cells and its secretion is promoted chiefly by glucose. It has been known that a variety of receptors exist in the β cells, and the secretion of insulin is controlled by various factors such as peptide hormones (galanin, somatostatin, gastric inhibitory polypeptide, glucagon, amylin, etc.), sugars (mannose, etc.), amino acids, and neurotransmitters in addition to glucose. As for the galanin and amylin, however, there has not yet been reported any discovery concerning the structure of their receptor protein cDNA. It is not known whether there exist any unknown receptor proteins or receptor protein subtypes.

It is a very important means in investigating development of new pharmaceuticals to clarify the relation between substances controlling the complicated functions of pancreas and specific receptors thereto. In order to develop new pharmaceuticals by conducting an effective screening of agonists and antagonists to the receptor proteins for controlling the functions of pancreas, it was necessary to investigate the function of receptor protein genes and also to express them in a suitable expression system.

By utilizing the fact that a G protein coupled receptor protein exhibits homology in part of the structure thereof at the amino acid sequence level, an experiment of looking at DNAs coding for novel receptor proteins relying upon a polymerase chain reaction (hereinafter simply referred to as "PCR") has recently been made.

Galanin is a peptide existing in central and peripheral areas and, in central area, it shows an action of inhibition of liberation of neurotransmitter (acetylcholine) (European Journal of Pharmacology, vol.164, 355–360, 1989) and an action of antagonizing foreign acetylcholine (Proceedings of National Academy of Sciences, U.S.A., vol.85, 9841–9845, 1988) while, in pancreas, it shows a pharmacological action such as inhibition of insulin secretion (Diabates, vol. 34, 192–196, 1985). It has been also confirmed that galanin has an effect of inhibiting the behavior of learning (Neuroscience Letters, vol.88, 331–335, 1988) and of inhibiting the feeling of fullness after a meal. Such findings suggest a possibility that, if pharmaceuticals which inhibit the action of galanin are developed, they may be used as intelligence tropic agents and as remedies for obesity and for diabetes.

All of the pharmacological actions of galanin take place via a specific galanin receptor existing in target tissues. Accordingly, the simplest means for inhibiting the action of galanin is to develop pharmaceuticals which specifically inhibit the reaction of galanin with the receptor, i.e. galanin receptor antagonists. In the development of galanin receptor antagonists, it is usually necessary to conduct a receptor binding experiment. In the case of galanin, experiments on galanin receptor binding using membrane fractions of brain hippocampal formation (European Journal of Biochemistry, vol. 181, 269–276, 1989) and of stomach and duodenum (Peptides, vol. 11, 333–338, 1990) have been reported already.

It has been also reported that there is a specific galanin receptor in Rin-m-5F cells obtained from rat pancreas (Endocrinology, vol. 124, 2635–2641, 1989). According to the above-mentioned reports, it is already possible to conduct a galanin receptor binding experiment. However, the amount of the galanin receptor in those membrane fractions is as low as around 50 fmol/mg and, therefore, it was necessary to use a large amount of cell fractions for one measurement.

Galanin exhibits the above-mentioned pharmacological actions in living body and, if the actions can be easily measured in vitro, that will be meaningful for the process of developing the receptor antagonists. It has been reported already that the action of inhibiting the insulin secretion by galanin can be substituted with an in vitro measurement using Langerhans islet isolated from pancreas (European Journal of Pharmacology, Vol. 203, 111–114, 1991). However, Langerhans island is required to be isolated upon each experiment and, therefore, this method is not easily accomplished.

As easier means, several methods using pancreatic β-cell strains (Rin-m-5F cells) have reported. They are, for example, a method in which an effect of galanin receptor to a second messenger system (i.e. an activity of inhibiting the adenylate cyclase) is measured (European Journal of Biochemistry, Vol. 177, 147–152, 1988) and a method in which an activity of opening the potassium channel is measured (Proceedings of National Academy of Sciences, U.S.A., Vol. 85, 1312–1316, 1988). A method in which the activity of inhibiting the insulin secretion of galanin using said cell strain has been reported too. However, those methods are applicable only for insulin secretion which is dependent upon forskolin (an adenylate cyclase activator) and the measurement for secretion of glucose-dependent insulin is not possible. Further, the secretion amount of insulin is small and the sensitivity is low.

After those, a method of preparing the β-cell strains using pancreas of transgenic mice (Proceedings of National Academy of Sciences, U.S.A., Vol. 85, 9037–9041, 1988) has been developed and establishments of cell strains such as βTC-1 cells (Proceedings of National Academy of Sciences, U.S.A., Vol. 85, 9037–9041, 1988), IgSV 195 cells (Diabates, Vol. 38, 1056–1062, 1989) and MIN6 cells (Endocrinology, Vol. 127, 126–132, 1990) have been reported. Among those, MIN6 cells hold the ability of insulin secretion depending upon the glucose concentration (which is a differentiating function inherent to β-cells) in the best manner and, in addition, they secret insulin in a high amount. However, it has not been known yet that galanin receptor protein is expressed in said MIN6 cells. In addition, there has been no proposal yet for an evaluating system for the biological activity of galanin and also for an effective method for screening the galanin receptor agonist or antagonist using the MIN6 cells.

Recently, cDNA which codes for human galanin receptor protein was cloned and its nucleotide sequence and also its amino acid sequence encoded by said cDNA have been disclosed (Proceedings of National Academy of Sciences, U.S.A., Vol. 91, 9780–9783, Oct. 11, 1994). However, there is no disclosure at all for a specific means for screening the galanin receptor agonist/antagonist using said receptor.

Under such circumstances, a method for screening and assessing galanin receptor agonist/antagonist in an efficient manner is still desired.

Galanin is a polypeptide comprising 29 amino acid residues separated from porcine small intestine [Tatemoto, K. et al., FEBS Letter, 164, 124–128(1983)] and its primary structure is hardly similar to those of other brain and intestinal hormones. Galanin immunoactivity is widely distributed in central nervous system and peripheral nervous system together with its receptor [Scofitsch, G. and Jacobowitz, D. M., Peptides, 6, 509–546(1985); Melander, T. et al., Journal of Comparative Neurology, 248, 475–517 (1986); Rokaeus, A., Trends in Neuroscience, 10,158–164 (1987)] and, since its distribution pattern is identical with the region containing the traditional neurotransmitters such as 5-HT, noradrenaline and acetylcholine, it is likely that galanin is present together with such neurotransmitters and controls the prenervous and postnervous actions by those neurotransmitters.

Galanin has many physiological actions and, in central nervous system, it strongly inhibits the single synaptic reflection in spinal nerve [Yanagisawa, M. et al., Neuroscience Letter, 70, 278–282(1986)] and its action is known to be far stronger than somatostatin. In addition, the physiological importance of galanin in nerve center has been greatly suggested because of stimulation of action for taking food [Kyrokouli, S. E. et al., European Journal of Pharmacology, 122, 159–160(1986)], participation in formation of memory [Crawley, J. N. and Wenk, G. L., Trends in Neuroscience, 12,278–282(1989)], inhibition of dopamine in median elevation [Nordstrom, O. et al., Neuroscience Letter, 73, 21–26(1987)], inhibition of release of acetylcholine in hippocampal double sides [Fisone, G. et al., Proceedings of the National Academy of Sciences of U.S.A., 84, 7339–7343(1987)], a decrease in metabolic circulation of 5-HT [Fuxe K., et al., Acta. Physiol. Scand., 133, 579–581 (1988)] and a decrease in a glutamic acid release by activation of ATP-sensitive $K^+$ channel [Ben-Ari, Y., European Journal of Neuroscience, 2, 62–68(1990)] as a result of administration of galanin to paraventricular nucleus of rats.

Especially, galanin is an only neuropeptide in which choline acetyltransferase is coexisting in the medial septal nucleus, nucleus of diagonal band and basal nucleus [Melender, T. et al., Brain Research, 360, 130–138(1985); Melender, T. et al., Neuroscience Letter, 19, 223–240(1986); Chen-Palay, V., Brain Research Bulletin, 21, 465–472 (1988)] and is known to act on cholinergic nerves in an inhibiting manner while, on the other hand, it is expected that, since denaturation in cholinergic nerves is noted in those sites in Alzheimer's disease, galanin antagonist may prevent the denaturation of the cholinergic nerves in Alzheimer's disease or the like [Whitehouse, P. J., et al., Science, 215, 1237–1239(1982); Chen-Palay, V., Journal of Comparative Neurology, 273,543–557 (1988)]. In hypophysis, action of stimulating the secretion of growth hormones and prolactin has been noted [Tanoh, T., et al., Neuroendocrinology, 54, 83–88(1991); Koshiyama, H., et al., Neuroscience Letter, 75, 49–54(1987)]. Particularly in the secretion of growth hormones, participation of cholinergic neuron via adjustment of secretion of hypothalamic somatostatin is noted.

On the other hand, in peripheral systems, galanin inhibits the basal secretion of insulin both in vivo and in vitro [McDnald, T. J. et al., Diabates, 34, 192–196(1985); Takeda, Y. et al., Biomedical Research, 8 (Suppl.), 117–125 (1987); Lindskog, S. et al., Acta. Physiol. Scand., 129, 305–309 (1987)] and, in addition, it inhibits the release of insulin by stimulation of glucose [Dunning, B. E. and Taborsky, G. J., Jr., Diabates, 37, 1157–1162(1988)]. When further immunohistological observation that nerve fiber net containing a dense galanin immunoactivity is noted around Langerhans islet of β cells is taken into consideration, it has been strongly suggested that galanin is one of the nerve controlling factors for secretion of pancreatic hormones, especially insulin. It is also noted that, in stomach, galanin inhibits the basal secretion of somatostatin on a dose-depending manner or it inhibits the secretion of somatostatin or gastrin by stimulation of GRP and that nerve fiber net containing galanin immunoactivity is observed in stomach and, accordingly, it is suggested that, even in stomach, galanin acts as one of the important nerve controlling factors for adjusting the secretion in stomach [Yanaihara, N. et al., in "Galanin" (ed. by Hokfelt, T. et al.), Macmillan Press, 185–196(1991)].

From the above descriptions, it is understood that galanin agonist is useful as a pharmaceutical agent such as a stimulant for secretion of growth hormones and an inhibitor for secretion of insulin and that galanin antagonist is useful as another pharmaceutical agent such as an inhibitor for secretion of growth hormones and a stimulant for secretion of insulin.

Usually, in developing agonists and antagonists for physiologically-active substances, investigations are made on the compounds which have high affinity with the receptors to which said substance is specifically bonded. At present, bovine hippocampal membrane fraction is used as a galanin receptor but, because of the difference in the animal species used, there is no guarantee that the compound exhibiting a high affinity to said membrane fraction has a high affinity to human galanin receptor as well. Human galanin receptor cDNA has been cloned and reported to exhibit an expression in COS cells [Habert-Ortoll, E. et al., Proceedings of the National Academy of Sciences, U.S.A., 91, 9780–9783(1994)] but, since the expressed amount is small and the expression is mere transient, it is thought to be unsuitable for screening.

SUMMARY OF THE INVENTION

One object of the present invention is to provide novel galanin receptor proteins and partial peptides thereof or salts thereof; DNAs comprising a DNA coding for said galanin receptor protein or its partial peptide; vectors carrying said DNA; transformants harboring said vector; cell membrane fractions obtained from said transformant; processes for producing said receptor protein or its partial peptide, or a salt thereof; methods for measuring the physiological actions of galanin using the galanin receptor protein (including a cell membrane fraction containing the receptor protein) or a galanin receptor protein-expressing cell (including the transformant); screening methods for a galanin receptor agonist/antagonist using the galanin receptor protein or a galanin receptor protein-expressing cell (including the transformant); kits for said screening; agonists or antagonists, obtained by said screening method; pharmaceutical compositions containing said agonist or antagonist; antibodies against said receptor protein; immunoassays using said receptor protein or said antibody; and use of said receptor protein and encoding DNA.

Another object of the present invention is to provide novel mouse pancreatic β cell line MIN6-derived galanin receptor proteins or partial peptides thereof; DNAs comprising a DNA coding for said galanin receptor protein or partial peptide; processes for producing said receptor protein or its partial peptide; methods of measuring the physiological actions of galanin using a mouse-derived cell line MIN6 or the galanin receptor protein; screening methods for a galanin receptor agonist/antagonist using said mouse-derived cell line MIN6 or the receptor protein; antibodies against said receptor protein; immunoassays using said receptor protein or said antibody; and use of said galanin receptor protein or said receptor protein peptide-encoding DNA.

Human galanin receptor proteins manufactured by the conventional method and the COS cells which express said human galanin receptor protein are insufficient as receptor samples for conducting a screening for galanin receptor agonist/antagonist. Consequently, there has been a demand for developing a more practical method for manufacturing human galanin receptor proteins.

If it is possible to screen the agonist/antagonist of galanin receptor using human galanin receptor protein, it is now possible to overcome the disadvantage by the use of experimental animals (for example, the possibility that, due to a difference in species, compounds which do not achieve an effect to human being may be obtained) whereby it is expected to conduct a development of pharmaceutical agents effective to human being in an efficient manner.

Yet another object of the present invention is to provide novel human galanin receptor proteins; partial peptides of the human galanin receptor protein; novel DNAs which code for the galanin receptor protein or partial peptide; vectors carrying said DNA; transformants harboring said vector; cell membrane fractions obtained from said transformant; processes for producing the human galanin receptor protein (or its partial peptide); methods for measuring the physiological actions of galanin using a human galanin receptor protein-expressing cell, said human galanin receptor protein; screening methods for a galanin receptor agonist/antagonist using a human galanin receptor protein-expressing cell (including the transformant); kits for said screening; agonists or antagonists, obtained by said screening method; pharmaceutical compositions containing said agonist or antagonist; antibodies against said human galanin receptor protein; immunoassays using said receptor protein or said antibody; and use of said human galanin receptor protein and encoding DNA.

In order to achieve the above-mentioned aims, the present inventors have made extensive investigations. As a result, the present inventors have succeeded in synthesizing DNA primers effective in efficiently isolating DNAs (DNA fragments) coding for G protein coupled receptor proteins by PCR techniques. The present inventors have succeeded in amplifying cDNA derived from various cells with said synthetic DNA primer, and have forwarded the analysis. Thus, the present inventors have succeeded in isolating novel G protein coupled receptor protein-encoding cDNAs, in determining the partial structure thereof, and have considered that the isolated cDNAs are homologous to known G protein coupled receptors at the nucleotide sequence level and at the amino acid sequence level and are each coding for a novel galanin receptor protein. Based upon the above knowledge, the present inventors have discovered that these DNAs make it possible to obtain a cDNA having a full length open reading frame (ORF) of the receptor protein, hence, to produce the receptor protein. The inventors have further succeeded in sequencing an entire amino acid sequence and entire nucleotide sequence of said galanin receptor protein.

The present inventors have found that, when said receptor protein expressed by a suitable means is used, an agonist or an antagonist to said receptor protein can be screened in vivo or from natural or nonnatural compounds by a receptor protein binding experiment or by a measurement of intracellular second messenger as an index. The present inventors have further found that said agonist and antagonist can be developed as preventive and therapeutic agents for the diseases or symptoms related to or caused by galanin.

The present inventors have furthermore found that the glucose or forskolin-dependent insulin secretion in cells expressing said galanin receptor protein is inhibited by galanin. That has been a finding for the first time. Depending upon said finding, the present inventors have found an easy and simple method for measuring the activity of galanin and galanin antagonist. At the same time, the present inventors have also found that the cell membrane fractions of cells expressing said galanin receptor protein contain large amount of galanin receptors and succeeded in establishing a screening for galanin receptor agonist/antagonist using the cell membrane fractions thereof.

For example, the present inventors have amplified G protein coupled receptor protein-encoding cDNA derived from mouse pancreatic β-cell strain MIN6 using a synthetic DNA primer for more effective isolation thereof, whereby its analysis has been carried out.

As a result thereof, the present inventors have succeeded in isolating the mouse-derived cDNA fragment which codes for a novel G protein coupled receptor protein and in elucidating its partial structure. In said mouse-derived G protein coupled receptor protein, there are similarities (homologies) at DNA and amino acid levels to the known G protein coupled receptor and, therefore, it is believed that it codes for a novel receptor protein exhibiting an expressing function in mouse pancreas.

The present inventors further continued their studies and have succeeded in cloning cDNA having a full-length translation unit and in analyzing an entire amino acid sequence and an entire nucleotide sequence of said receptor protein. Since said mouse-derived G protein coupled receptor protein has a high homology at DNA and amino acid levels to the human-derived galanin receptor protein (Proceedings of National Academy of Sciences, U.S.A., 91, 9780–9783, 1994), it has been found that said mouse-derived G protein coupled receptor protein is identical with a mouse-derived galanin receptor protein.

Furthermore, the present inventors have newly found that the glucose or forskolin-dependent insulin secretion of MIN6 cells is inhibited by galanin. Based upon said finding, the present inventors have found an easy and simple method for measuring the activity of galanin and galanin antagonist. At the same time, the present inventors have also found that the cell membrane fractions of MIN6 cells contain large amount (0.5–1.0 pmol/mg) of galanin receptor and succeeded in establishing a method of screening galanin receptor agonist/antagonist using the cell membrane fractions of MIN6 cells.

To be more specific, the present inventors have amplified and cloned novel cDNA fragments derived from mouse pancreatic β-cell strain MIN6 as shown in FIG. 1 by PCR and, from the result of analysis of their sequence, have clarified that they code for a novel receptor protein. When said sequence was translated into amino acid sequences, third, fourth, fifth and sixth transmembrane domains were confirmed on hydrophobic plots (FIG. 2). The size of the amplified DNA was about 400 bp which was almost same as that of the known G protein coupled receptor protein.

The inventors have retrieved the data base based on, as a template, the nucleotide sequence of the isolated DNA and observed 36% homology to human-derived somatostatin receptor subtype 4 (JN0605), 30% homology to human-derived somatostatin receptor subtype 2 (B41795), and 30% homology to rat-derived ligand unknown receptor (A39297), respectively (FIG. 3), which are known G protein coupled receptor proteins. The aforementioned abbreviations in parentheses are reference numbers that are assigned when they are registered as data to NBRF-PIR/Swiss-PROT and are, usually, each called "Accession Number" or "Entry Name".

Moreover, the present inventors have prepared cDNA from the poly(A)+RNA fractions extracted from MIN6 cells and have inserted said cDNA into lambda gt22 phage to prepare a cDNA library. Further, the present inventors have screened the cDNA library using, as a probe, the G protein coupled receptor protein cDNA fragment p3H2-34 obtained by PCR and succeeded in cloning cDNA which completely codes for the G protein coupled receptor protein of the present invention. A nucleotide sequence of said cDNA and an amino acid sequence encoded thereby are given in FIG. 4. A hydrophobic plotting was conducted based upon said amino acid sequence and the first, second, third, fourth, fifth, sixth and seventh transmembrane domains were confirmed (FIG. 5). The G protein coupled receptor protein of the present invention has 92% homology at the amino acid level to the known human galanin receptor protein.

In another aspect, the present inventors have succeeded, for example, in cloning a DNA which codes for novel human galanin receptor protein having an amino acid sequence which differs from that of known human galanin receptor protein. In the known human galanin receptor protein, the fifteenth amino acid in its amino acid sequence is Cys while, in the human galanin receptor protein of the present invention, the fifteenth amino acid in its amino acid sequence (SEQ ID NO: 5 and FIGS. 12 & 13) is Trp. In addition, in the nucleotide sequence of DNA which codes for the known human galanin receptor protein, the base sequence which codes for the fifteenth amino acid of said human galanin receptor protein is $^{15}$Cys (TGT) while, in the base sequence of DNA which codes for the human galanin receptor protein of the present invention, the base sequence which codes for the fifteenth amino acid in said human galanin receptor protein is $^{15}$Trp (TGG).

The present inventors have further succeeded in manufacturing a CHO cell strain which expresses far more amount of the human galanin receptor protein of the present invention than the COS cells which express the known human galanin receptor protein [Habert-Ortoll, E. et al., Proceedings of the National Academy of Sciences of the U.S.A., 91, 9780–9783 (1994)]. It has been furthermore found that, when said CHO cell strain of the human galanin receptor protein of the present invention or partial peptide thereof is used, it is now possible to screen the human galanin receptor agonist/antagonist in an effective and reliable manner. Based upon those findings, the present inventors have continued various investigations and, as a result, they have achieved the present invention.

Accordingly, one aspect of the present invention is (1) a galanin receptor protein comprising an amino acid sequence selected from the group consisting of an amino acid sequence represented by SEQ ID NO: 1, SEQ ID NO: 2 or SEQ ID NO: 5 and substantial equivalents thereto, or a salt thereof;

(2) the receptor protein according to the above (1), which is produced by a transformant CHO cell;

(3) a DNA which comprises a nucleotide sequence coding for a galanin receptor protein of the above (1);

(4) a vector comprising the DNA according to the above (3);

(5) a transformant carrying the vector according to the above (4);

(6) the transformant according to the above (5), wherein the host cell is a CHO cell;

(7) a process for producing a galanin receptor protein according to the above (1), which comprises culturing a transformant of the above (5) under conditions suitable to express said galanin receptor protein;

(8) a screening method for an agonist or antagonist of a galanin receptor protein according to the above (1), which comprises carrying out a comparison between:

(i) at least one case where galanin is contacted with at least one component selected from the group consisting of a galanin receptor protein according to the above (1), a partial peptide thereof and a mixture thereof, and (ii) at least one case where galanin together with a compound to be tested is contacted with at least one component selected from the group consisting of a galanin receptor protein according to the above (1), a partial peptide thereof and a mixture thereof;

(9) a kit for the screening of one or more agonists or antagonists to a galanin receptor protein according to the above (1), which comprises at least one component selected from the group consisting of a galanin receptor protein according to the above (1), a partial peptide thereof and a mixture thereof; and

(10) an agonist or antagonist of a galanin receptor, which is obtained by the screening method according to the above (8) or by the kit according to the above (9).

Another aspect of the present invention is

(11) a mouse-derived galanin receptor protein comprising an amino acid sequence selected from the group consisting of an amino acid sequence represented by SEQ ID NO: 1 and substantial equivalents thereto; or a salt thereof;

(12) a mouse-derived galanin receptor protein according to the above (11), which comprises an amino acid sequence selected from the group consisting of an amino acid sequence represented by SEQ ID NO: 2 and substantial equivalents thereto; or a salt thereof;

(13) a human galanin receptor protein comprising an amino acid sequence selected from the group consisting of an amino acid sequence represented by SEQ ID NO: 5 and substantial equivalents thereto; or a salt thereof;

(14) a partial peptide of a galanin receptor protein according to the above (1), or a salt thereof;

(15) a partial peptide of a mouse-derived galanin receptor protein according to the above (11) or (12), or a salt thereof;

(16) a partial peptide of a human galanin receptor protein according to the above (13), or a salt thereof;

(17) a DNA which comprises a nucleotide sequence coding for a mouse-derived galanin receptor protein of the above (11) or (12);

(18) a DNA which comprises a nucleotide sequence coding for a human galanin receptor protein of the above (13);

(19) a DNA of the above (17) comprising a nucleotide sequence represented by SEQ ID NO: 3;

(20) a DNA of the above (17) comprising a nucleotide sequence represented by SEQ ID NO: 4;

(21) a DNA of the above (18) comprising a nucleotide sequence represented by SEQ ID NO: 6;

(22) a vector comprising a DNA according to the above (17);

(23) a vector comprising a DNA according to the above (18);

(24) a transformant (including a transfectant) carrying a vector of the above (22);

(25) a transformant (including a transfectant) carrying a vector of the above (23);

(26) a process for producing a mouse-derived galanin receptor protein or a salt thereof according to the above (11), which comprises culturing a transformant of the above (24) to produce said galanin receptor on the membrane of the transformant;

(27) a process for producing a human galanin receptor protein or a salt thereof according to the above (13), which comprises culturing a transformant of the above (25) under conditions to express said galanin receptor;

(28) a cell or membrane fraction containing a galanin receptor protein according to the above (1);

(29) a cell or membrane fraction containing a mouse-derived galanin receptor protein according to the above (11) or (12);

(30) a cell or membrane fraction containing a human galanin receptor protein according to the above (13);

(31) a screening method for a galanin receptor agonist and/or antagonist, which comprises using a galanin receptor protein according to the above (1), a partial peptide according to the above (14) or a cell or membrane fraction according to the above (28);

(32) a screening method for a mouse-derived galanin receptor agonist and/or antagonist, which comprises using a mouse-derived galanin receptor protein according to the above (11) or (12), a partial peptide according to the above (15) or a cell or membrane fraction according to the above (29);

(33) a screening method for a human galanin receptor agonist and/or antagonist, which comprises using a human galanin receptor protein according to the above (13), a partial peptide according to the above (16) or a cell or membrane fraction according to the above (30);

(34) a screening method for a galanin receptor agonist and/or antagonist, which comprises carrying out a comparison between:
(i) at least one case where galanin is contacted with at least one component selected from the group consisting of a galanin receptor protein or a salt thereof according to the above (1), a partial peptide or a salt thereof according to the above (14), a cell or membrane fraction according to the above (28), and a mixture thereof, and
(ii) at least one case where galanin together with a sample (including a compound) to be tested is contacted with at least one component selected from the group consisting of a galanin receptor protein or a salt thereof according to the above (1), a partial peptide or a salt thereof according to the above (14), a cell or membrane fraction according to the above (28), and a mixture thereof;

(35) a screening method for a mouse-derived galanin receptor agonist and/or antagonist, which comprises carrying out a comparison between:
(i) at least one case where galanin is contacted with at least one component selected from the group consisting of a mouse-derived galanin receptor protein or a salt thereof according to the above (11), a partial peptide or a salt thereof according to the above (15), and a mixture thereof, and
(ii) at least one case where galanin together with a sample (including a compound) to be tested is contacted with at least one component selected from the group consisting of a mouse-derived galanin receptor protein or a salt thereof according to the above (11), a partial peptide or a salt thereof according to the above (15), and a mixture thereof;

(36) a screening method for a human galanin receptor agonist and/or antagonist, which comprises carrying out a comparison between:
(i) at least one case where galanin is contacted with at least one component selected from the group consisting of a human galanin receptor protein or a salt thereof according to the above (13), a partial peptide or a salt thereof according to the above (16), a cell or membrane fraction according to the above (30), and a mixture thereof, and (ii) at least one case where galanin together with a sample (including a compound) to be tested is contacted with at least one component selected from the group consisting of a human galanin receptor protein or a salt thereof according to the above (13), a partial peptide or a salt thereof according to the above (16), a cell or membrane fraction according to the above (30), and a mixture thereof;

(37) a kit for the screening of a galanin receptor agonist and/or antagonist, which comprises at least one component selected from the group consisting of a galanin receptor protein or a salt thereof according to the above (1), a partial peptide or a salt thereof according to the above (14), a cell or membrane fraction according to the above (28), and a mixture thereof;

(38) a kit for the screening of a mouse-derived galanin receptor agonist and/or antagonist, which comprises at least one component selected from the group consisting of a mouse-derived galanin receptor protein or a salt thereof according to the above (11) or (12), a partial peptide or a salt thereof according to the above (15), a cell or membrane fraction according to the above (29), and a mixture thereof;

(39) a kit for the screening of a human galanin receptor agonist and/or antagonist, which comprises at least one component selected from the group consisting of a galanin receptor protein or a salt thereof according to the above (13), a partial peptide or a salt thereof according to the above (16), a cell or membrane fraction according to the above (30), and a mixture thereof;

(40) a galanin receptor agonist and/or antagonist, obtained by a method according to any of the above (31) to (36) or a kit according to any of the above (37) to (39);

(41) a galanin receptor agonist and/or antagonist, obtained by a method according to the above (32) or (35) or a kit according to the above (38);

(42) a galanin receptor agonist and/or antagonist, obtained by a method according to the above (33) or (36) or a kit according to the above (39);

(43) a pharmaceutical composition comprising an effective amount of the galanin receptor agonist according to (40);

(44) a pharmaceutical composition comprising an effective amount of the galanin receptor agonist according to (41);

(45) a pharmaceutical composition comprising an effective amount of the galanin receptor agonist according to (42);

(46) a pharmaceutical composition comprising an effective amount of the galanin receptor antagonist according to (40);

(47) a pharmaceutical composition comprising an effective amount of the galanin receptor antagonist according to (41);

(48) a pharmaceutical composition comprising an effective amount of the galanin receptor antagonist according to (42);

(49) a pharmaceutical composition according to (43) which is an inhibitor for acetylcholine liberation, an inhibitor for insulin secretion, a stimulant for growth hormone secretion, an inhibitor for learning behavior or satiety;

(50) a pharmaceutical composition according to (46) which is an agent for promoting the acetylcholine liberation, an agent for inhibiting the growth hormone secretion, an agent for promoting the insulin secretion, an agent for promoting the learning behavior or an agent for promoting satiety;

(51) an antibody against at least one component selected from the group consisting of a galanin receptor protein or a salt thereof according to the above (1) and a partial peptide or a salt thereof according to the above (14);

(52) an antibody against at least one component selected from the group consisting of a mouse-derived galanin receptor protein or a salt thereof according to the above (11) or (12) and a partial peptide or a salt thereof according to the above (15); and

(53) an antibody against at least one component selected from the group consisting of a human galanin receptor protein or a salt thereof according to the above (13) and a partial peptide or a salt thereof according to the above (16).

To be more specific, the present invention relates to the following:

(54) a method of screening a galanin receptor agonist or antagonist, characterized in that, the binding amount of the labeled galanin with the galanin receptor protein or its salt according to (1) (e.g., the mouse-derived galanin receptor protein or its salt according to (11), etc.) or with the partial peptide or its salt according to (14) (e.g., the partial peptide of the mouse-derived galanin receptor protein or its salt according to (15), etc.) is measured in the case where the labeled galanin is contacted with the galanin receptor protein or its salt according to (1) (e.g., the mouse-derived galanin receptor protein or its salt according to (11), etc.) or with the partial peptide or its salt according to (14) (e.g., the partial peptide of the mouse-derived galanin receptor protein or its salt according to (15), etc.) and also in the case where the labeled galanin and the test compound are contacted with the galanin receptor protein or its salt according to (1) (e.g., the mouse-derived galanin receptor protein or its salt according to (11), etc.) or with the partial peptide or its salt according to (14) (e.g., the partial peptide of the mouse-derived galanin receptor protein or its salt according to (15), etc.) and the comparison is made between them;

(55) a method of screening a galanin receptor agonist or antagonist, characterized in that, the labeled galanin is contacted with the cells (except mouse-derived MIN6 cells [FERM BP-4954]) containing the galanin receptor protein according to (1) (e.g., the mouse-derived galanin receptor protein according to (11), etc.) and the labeled galanin and the test compound are contacted with the cells (except mouse-derived MIN6 cells [FERM BP-4954]) containing the galanin receptor protein according to (1) (e.g., the mouse-derived galanin receptor protein according to (11), etc.) and the binding amounts of the labeled galanin with said cells in both cases are measured and compared;

(56) a method of screening a galanin receptor agonist or antagonist, characterized in that, the labeled galanin is contacted with the cell membrane fractions of cells (except mouse-derived MIN6 cells [FERM BP-4954]) containing the galanin receptor protein according to (1) (e.g., the mouse-derived galanin receptor protein according to (11), etc.) and the labeled galanin and the test compound are contacted with the cell membrane fraction of cells (except mouse-derived MIN6 cells [FERM BP-4954]) containing the galanin receptor protein according to (1) (e.g., the mouse-derived galanin receptor protein according to (11), etc.) and the binding amounts of the labeled galanin with the membrane fractions of said cells in both cases are measured and compared;

(57) a method of screening a galanin receptor agonist or antagonist, characterized in that, the labeled galanin is contacted with the galanin receptor protein according to (1) (e.g., the mouse-derived galanin receptor protein according to (11), etc.) expressed in cell membranes of the transformant according to (5) (e.g., the mouse-derived galanin receptor protein-expressible transformant according to (24), etc.) by culturing said transformant and the labeled galanin and the test compound are contacted with the galanin receptor protein according to (1) (e.g., the mouse-derived galanin receptor protein according to (11), etc.) expressed in cell membranes of the transformant according to (5) (e.g., the mouse-derived galanin receptor protein-expressible transformant according to (24), etc.) by culturing said transformant and the binding amounts of the labeled galanin with said galanin receptor in both cases are measured and compared;

(58) a method of screening a galanin receptor agonist or antagonist, characterized in that, galanin is contacted with the cells (except the mouse-derived MIN6 cells [FERM BP-4954]) containing the galanin receptor protein according to (1) (e.g., the mouse-derived galanin receptor protein according to (11), etc.) and galanin and the test compound are contacted with the cells (except the mouse-derived MIN6 cells [FERM BP-4954]) containing the galanin receptor protein according to (1) (e.g., the mouse-derived galanin receptor protein according to (11), etc.) and the resulting cell-stimulating activities via the galanin receptor protein in both cases are measured and compared;

(59) a method of screening a galanin receptor agonist or antagonist, characterized in that, galanin is contacted with the galanin receptor protein according to (1) (e.g., the mouse-derived galanin receptor protein according to (11), etc.) expressed in cell membranes of the transformant according to (5) (e.g., the mouse-derived galanin receptor protein-expressible transformant according to (24), etc.) by culturing said transformant and galanin and the test compound are contacted with the galanin receptor protein according to (1) (e.g., the mouse-derived galanin receptor protein according to (11), etc.) expressed in cell membranes of the transformant according to (5) (e.g., the mouse-derived galanin receptor protein-expressible transformant according to (24), etc.) by culturing said transformant and the resulting cell stimulating activities via the galanin receptor protein are measured and compared;

(60) a method of screening according to (58) or (59) in which the cell-stimulating activity is an activity which accelerates or inhibits arachidonic acid liberation, acetylcholine liberation, intracellular $Ca^{2+}$ liberation, intracellular cAMP production, intracellular cGMP production, inositol phosphate production, cell membrane potential variation, phosphorylation of intracellular protein, activation of c-fos, a decrease in pH, insulin secretion, etc. (especially the activity which accelerates or inhibits the intracellular cAMP production or insulin secretion);

(61) a galanin receptor agonist or antagonist obtained by a screening methods according to any of (31), (34) (e.g., (32), (35), etc.) and (54) to (60);

(62) an agent for inhibiting acetylcholine liberation, insulin secretion, learning behavior or feeling of satiety after a meal characterized in containing the galanin receptor agonist according to (61);

(63) an agent for accelerating acetylcholine liberation, insulin secretion, behavior of learning or feeling of fulfillment after a meal characterized in containing the galanin receptor antagonist according to (61);

(64) an intelligence tropic agent or a remedy for obesity or for diabetes characterized in containing the galanin receptor antagonist according to (40) (e.g., (41), etc.) or (61);

(65) a kit for screening according to (37) (e.g., (38), etc.), characterized in comprising a cell containing the galanin receptor protein according to (1) (e.g., the mouse-derived galanin receptor protein according to (11), etc.);

(66) a kit for screening according to (37) (e.g., (38), etc.), characterized in containing the membrane fractions of the cells which contain the galanin receptor protein according to (1) (e.g., the mouse-derived galanin receptor protein according to (11), etc.);

(67) a galanin receptor agonist or antagonist obtained by the use of the kit for screening according to (37) (e.g., (38), etc.), (65) or (66);

(68) an agent for inhibiting acetylcholine liberation, insulin secretion, learning behavior or feeling of fulfillment after a meal characterized in containing the galanin receptor agonist according to (67);

(69) an agent for accelerating acetylcholine liberation, insulin secretion, behavior of learning or feeling of fulfillment after a meal characterized in containing the galanin receptor antagonist according to (67);

(70) an intelligence tropic agent or a remedy for obesity or for diabetes characterized in containing the galanin receptor antagonist according to (40) (e.g., (41), etc.) or (69); and

(71) a method of quantitative determination of the galanin receptor protein or its salt according to (1) (e.g., the mouse-derived galanin receptor protein or its salt according to (11), etc.) or the partial peptide or its salt according to (14) (e.g., the partial peptide of the mouse-derived galanin receptor protein or its salt according to (15), etc.), characterized in that, the antibody according to (51) (e.g., the antibody according to (52), etc.) is contacted with the galanin receptor protein or its salt according to (1) (e.g., the mouse-derived galanin receptor protein or its salt according to (11), etc.) or the partial peptide or its salt according to (14) (e.g., the partial peptide of the mouse-derived galanin receptor protein or its salt according to (15), etc.).

The present invention furthermore provides the following:

(72) a method of measuring the physiological activity of galanin, characterized in that, the biological activity of the mouse-derived MIN6 cells when the mouse-derived MIN cells (FERM BP-4954) or the cell membrane fractions thereof are contacted with galanin;

(73) a method of screening a galanin receptor agonist or antagonist, characterized in that, a comparison is made between the cases where (i) galanin is contacted with the mouse-derived MIN6 cells (FERM BP-4954) or cell membrane fractions thereof and (ii) galanin and the test compound are contacted with the mouse-derived MIN6 cells (FERM BP-4954) or cell membrane fractions thereof;

(74) a kit for screening for a galanin receptor agonist or antagonist characterized in containing the mouse-derived MIN6 cells (FERM BP-4954) or cell membrane fractions thereof;

(75) a galanin receptor agonist or antagonist obtained by the method for screening according to (73) or by the kit for screening according to (74);

(76) an inhibitor for liberation of acetylcholine, an inhibitor for secretion of insulin, an inhibitor for the behavior of learning or an inhibitor for feeling satiety after a meal characterized in containing the galanin receptor agonist according to (75);

(77) an accelerator for liberation of acetylcholine, an accelerator for secretion of insulin, an accelerator for the behavior of learning or an accelerator for feeling satiety after a meal characterized in containing the galanin receptor antagonist according to (75);

(78) a method for screening a galanin receptor agonist or antagonist, characterized in that, the labeled galanin is contacted with the mouse-derived MIN6 cells (FERM BP-4954) and the labeled galanin and the test compound are contacted with the mouse-derived MIN6 cells (FERM BP-4954) and the binding amounts of the labeled galanin with said mouse-derived galanin MIN6 cells in both cases are measured and compared;

(79) a method of screening a galanin receptor agonist or antagonist, characterized in that, the labeled galanin is contacted with the cell membrane fractions of the mouse-derived MIN6 cells (FERM BP-4954) and the labeled galanin and the test compound are contacted with the cell membrane fractions of the mouse-derived MIN6 cells (FERM BP-4954) and the binding amounts of the labeled galanin with said membrane fractions of the mouse-derived MIN6 cells in both cases are measured and compared;

(80) a method of screening a galanin receptor agonist or antagonist, characterized in that, galanin is contacted with the mouse-derived MIN6 cells (FERM BP-4954) and galanin and the test compound are contacted with the mouse-derived MIN6 cells (FERM BP-4954) and the resulting cell-stimulating activities via the mouse-derived galanin receptor (especially the activity of secretion of insulin from MIN6 cells or the activity of inhibiting or accelerating the cAMP production in the MIN6 cells) in both cases are measured and compared;

(81) a method of screening according to the above (80) in which the cell-stimulating activity is an activity for accelerating or inhibiting the arachidonic acid liberation, acetylcholine liberation, intracellular $Ca^{2+}$ liberation, intracellular cAMP production, intracellular cGMP production, inositol phosphate production, cell membrane potential variation, phosphorylation of intracellular protein, activation of c-fos, a decrease in pH, secretion of insulin, etc. (especially the activity which accelerates or inhibits the intracellular cAMP production or the insulin secretion);

(82) a galanin receptor agonist or antagonist obtained by a method of screening according to any of (73) and (78) to (81);

(83) an inhibitor for liberation of acetylcholine, an inhibitor for secretion of insulin, an inhibitor for the behavior of learning and an inhibitor for feeling fulfillment after a meal characterized in containing the galanin receptor agonist according to (75) or (82);

(84) an accelerator for liberation of acetylcholine, an accelerator for secretion of insulin, an accelerator for the behavior of learning and an accelerator for feeling satiety after a meal characterized in containing the galanin receptor antagonist according to (75) or (82); and

(85) an intelligence tropic agent or a remedy for obesity or for diabetes characterized in containing the galanin receptor antagonist according to (75) or (82).

Yet another aspect of the present invention is:

(86) a partial peptide according to (16) in which the partial peptide is a region exposed outside the cell membrane of the human galanin receptor protein molecule according to (13);

(87) a vector according to (23) in which the vector is an expression vector for the human galanin receptor protein as indicated by pTS863;

(88) a transformant according to (25) in which the host cell is a CHO cell;

(89) a CHO cell according to (88) in which the CHO cell is CHO/pTS863-5 or CHO/pTS863-7;

(90) a cell or cell membrane fraction thereof according to (30) in which the cell is CHO/pTS863-5 or CHO/pTS863-7;

(91) a method of screening the galanin receptor agonist or antagonist according to (33), which comprises carrying out a comparison between the cases where (i) galanin is contacted with the human galanin receptor protein or salt thereof according to (13) or with the partial peptide or salt thereof according to (16) and (ii) galanin and the test compound are contacted with the human galanin receptor protein or salt thereof according to (13) or with the partial peptide or salt thereof according to (16);

(92) a method of screening the galanin receptor agonist or antagonist according to (33), which comprises measuring and comparing the binding amounts of the labeled galanin to said human galanin receptor protein, partial peptide thereof or salt thereof in the cases where (i) the labeled galanin is contacted with the human receptor protein or salt thereof according to (13) or with the partial peptide or salt thereof according to (16) and (ii) the labeled galanin and the test compound are contacted with the human galanin receptor protein or salt thereof according to (13) or with the partial peptide or salt thereof according to (16);

(93) a method of screening the galanin receptor agonist or antagonist according to (33), which comprises carrying out a comparison between the cases where (i) the labeled galanin is contacted with the cell or cell membrane fraction thereof according to (30) and (ii) the labeled galanin and the test compound are contacted with the cell or the cell membrane fraction thereof according to (30);

(94) a method of screening the galanin receptor agonist or antagonist according to (33), which comprises measuring and comparing the binding amounts of the labeled galanin with said cell or cell membrane fraction thereof in the cases where (i) the labeled galanin is contacted with the cell or the cell membrane fraction thereof according to (30) and (ii) the labeled galanin and the test compound are contact with the cell or the cell membrane fraction thereof according to (30);

(95) a method of screening the galanin receptor agonist or antagonist according to (33), which comprises measuring and comparing cell stimulating activities via the recombinant human galanin receptor (for example, activities which promote or inhibit the opening of $K^+$ channel, closing of N type Ca$^+$ channel, liberation of arachidonic acid, liberation of acetylcholine, variations in intracellular Ca$^{2+}$ concentration, inhibition of intracellular cAMP production, production of inositol phosphate, cell membrane potential changes, phosphorylation of intracellular protein, activation of c-fos, decrease in pH, cell migration activity, secretion of hormones, activation of G protein and cell promulgation, etc.) in the cases where (i) galanin is contacted with the cell or the cell membrane fraction thereof according to (30) and (ii) galanin and the test compound are contacted with the cell or the cell membrane fraction thereof according to (30);

(96) a pharmaceutical composition according to (45) for inhibiting liberation of acetylcholine, inhibiting secretion of insulin, stimulating secretion of growth hormones, inhibiting learning behavior or inhibiting satiety;

(97) a pharmaceutical composition according to (45) which is a prophylactic or therapeutic agent for schizophrenic illness or stomach ulcer or is a sedative;

(98) a pharmaceutical composition according to (48) for promoting the acetylcholine liberation, inhibiting the growth hormone secretion, promoting the insulin secretion, promoting the learning behavior or promoting satiety;

(99) a pharmaceutical composition according to (48) which is a prophylactic and therapeutic agent for diabetes, Alzheimer's disease or dementia;

(100) a preventive and therapeutic agent containing the DNA according to (18) for a galanin receptor protein-deficient disease; and (101) a preventive and therapeutic agent according to (100) in which the galanin receptor protein-deficient disease is diabetes, Alzheimer's disease or dementia.

Yet another aspect of the present invention is:

(102) a galanin receptor protein according to the above (1) which comprises
an amino acid sequence selected from the group consisting of an amino acid sequence represented by SEQ ID NO: 1, amino acid sequences wherein one or more amino acid residues (preferably from 1 to 30 amino acid residues, more preferably from 1 to 10 amino acid residues) are deleted from the amino acid sequence of SEQ ID NO: 1, amino acid sequences wherein one or more amino acid residues (preferably from 1 to 30 amino acid residues, more preferably from 1 to 10 amino acid residues) are added to the amino acid sequence of SEQ ID NO: 1, and amino acid sequences wherein one or more amino acid residues (preferably from 1 to 30 amino acid residues, more preferably from 1 to 10 amino acid residues) in the amino acid sequence of SEQ ID NO: 1 are substituted with one or more other amino acid residues,
or a salt thereof;

(103) a galanin receptor protein according to the above (1) which comprises
an amino acid sequence selected from the group consisting of an amino acid sequence represented by SEQ ID NO: 2, amino acid sequences wherein one or more amino acid residues (preferably from 1 to 30 amino acid residues, more preferably from 1 to 10 amino acid residues) are deleted from the amino acid sequence of SEQ ID NO: 2, amino acid sequences wherein one or more amino acid residues (preferably from 1 to 30 amino acid residues, more preferably from 1 to 10 amino acid residues) are added to the amino acid sequence of SEQ ID NO: 2, and amino acid sequences wherein one or more amino acid residues (preferably from 1 to 30 amino acid residues, more preferably from 1 to 10 amino acid residues) in the amino acid sequence of SEQ ID NO: 2 are substituted with one or more other amino acid residues,
or a salt thereof; and (104) a galanin receptor protein according to the above (1) which comprises an amino acid sequence selected from the group consisting of an amino acid sequence represented by SEQ ID NO: 5, amino acid sequences wherein one or more amino acid residues (preferably from 1 to 30 amino acid residues, more preferably from 1 to 10 amino acid residues) are deleted from the amino acid sequence of SEQ ID NO: 5, amino acid sequences wherein one or more amino acid residues (preferably from 1 to 30 amino acid residues, more preferably from 1 to 10 amino acid residues) are added to the amino acid sequence of SEQ ID NO: 5, and amino acid sequences wherein one or more amino acid residues (preferably from 1 to 30 amino acid residues, more preferably from 1 to 10 amino acid residues) in the amino acid sequence of SEQ ID NO: 5 are substituted with one or more other amino acid residues,
or a salt thereof.

Yet another aspect of the present invention is:

(105) a process according to the above (27), wherein said transformant is produced by transforming a host cell, CHO cell, with a vector comprising a nucleotide sequence coding for a human-derived galanin receptor protein;

(106) a pharmaceutical composition comprising an effective amount of an agonist according to the above (40) or a salt thereof in admixture with a pharmaceutically acceptable diluent, carrier or excipient;

(107) a pharmaceutical composition according to the above (106), which inhibits liberation of acetylcholine, secretion insulin, learning action, or satiety;

(108) a pharmaceutical composition comprising an effective amount of an antagonist according to the above (40) or a salt thereof in admixture with a pharmaceutically acceptable diluent, carrier or excipient;

(109) a pharmaceutical composition according to the above (108), which promotes liberation of acetylcholine, secretion insulin, learning action, or satiety; and (110) a transformant CHO cell capable of expressing human-derived galanin receptor proteins.

As used herein the term "substantial equivalent(s)" means that the activity of the protein, e.g., nature of the ligand binding activity, and physical characteristics are substantially the same. Substitutions, deletions or insertions of amino acids often do not produce radical changes in the physical and chemical characteristics of a polypeptide, in which case polypeptides containing the substitution, deletion, or insertion would be considered to be substantially equivalent to polypeptides lacking the substitution, deletion, or insertion. Substantially equivalent substitutes for an amino acid within the sequence may be selected from other members of the class to which the amino acid belongs. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine, The positively charged (basic) amino acids include arginine, lysine and histidine. The negatively charged (acidic) amino acids include aspartic acid and glutamic acid.

BRIEF DESCRIPTION OF THE DRAWINGS

FIG. 1 is the partial nucleotide sequence of the (SEQ ID NO: 16) of the novel receptor protein cDNA clone, p3H2-34, obtained from mouse pancreatic β-cell line, MIN6, by PCR amplification and the amino acid sequence encoded thereby (SEQ ID NO: 12), wherein the underlined parts correspond to the synthetic primers used for the PCR amplification.

FIG. 3 is the partial amino acid sequence encoded by the novel receptor protein cDNA included in p3H2-34 (SEQ ID NO: 12), relative to the partial amino acid sequence each of human somatostatin receptor subtype 4 protein (JN0605) (SEQ ID NO: 13), human somatostatin receptor subtype 2 protein (B41795) (SEQ ID NO: 14) and rat-derived ligand unknown receptor protein (A39297) (SEQ ID NO: 15), wherein reverse amino acid residues are in agreement.

FIG. 4 shows the nucleotide sequence of the mouse-derived galanin receptor protein cDNA clone (SEQ ID NO: 17), pMGR20, which has been cloned with, as a probe, the cDNA insert in p3H2-34 and the amino acid sequence encoded thereby (SEQ ID NO: 2).

FIG. 6 is the amino acid sequence (SEQ ID NO: 2) (MOUSEGALRECE) of the mouse-derived galanin receptor protein encoded by pMGR20, relative to the amino acid sequence (SEQ ID NO: 5) (HUMAGALAMI) of the human-derived galanin receptor protein, wherein reverse amino acid residues are in agreement.

FIG. 11 is the nucleotide sequence nucleotides 1-1126 of (SEQ ID NO: 15) and deduced amino acid sequence (1st to 135th) amino acids 1-135 (SEQ ID NO: 5) of the human galanin receptor protein obtained in Example 11.

Arrowheads indicate the sizes of the molecular weight markers.

Figure 15:
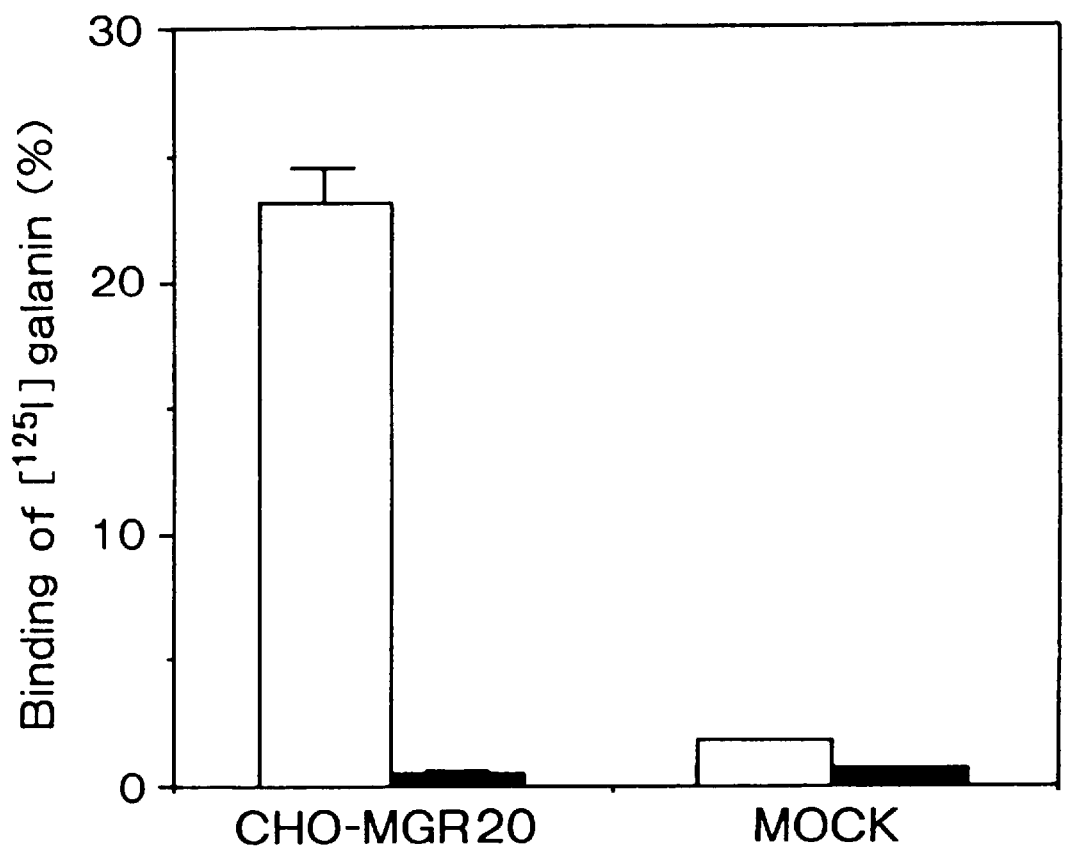

FIG. 15 illustrates a comparison of porcine [$^{125}$I]galanin binding to CHO cells transformed with or without a mouse galanin receptor cDNA. CHO-MGR20 cells transformed with a full-length translation unit or mock transformed CHO cells were incubated with [$^{125}$I]galanin (100 pM at final concentration) at 37° C. for 1 hr in the absence (open column) or presence (closed column) of unlabeled porcine galanin (1 μM at final concentration). The amounts of [$^{125}$I]galanin bound are represented as a percentages of the radioactivity remaining on the cells after washing. Values indicated are mean±S.E.M. in triplicate.

FIG. 16 is a primary structure comparison of mouse (SEQ ID NO: 2) and human (SEQ ID NO: 5) galanin receptors. Identical residues are indicated by the vertical line. Putative membrane spanning domains I–VII are boxed.

Figure 17:
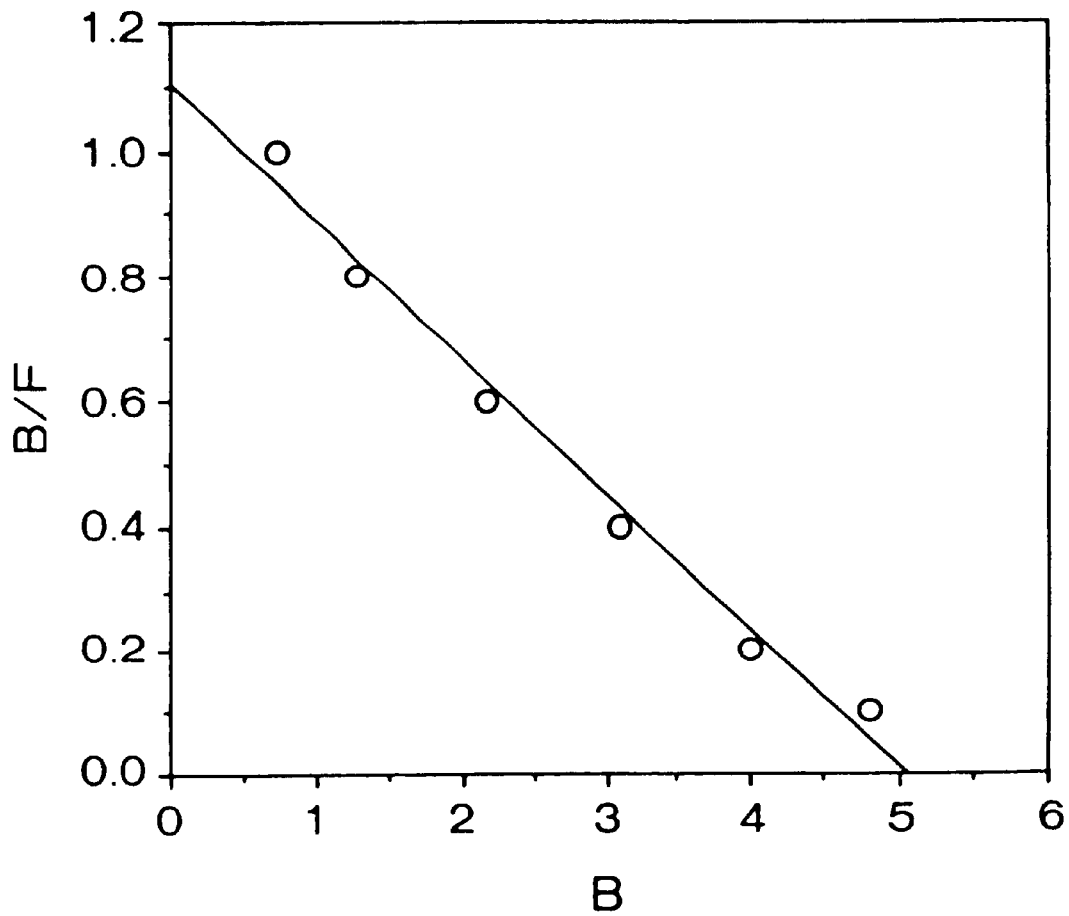

FIG. 17 depicts a profile of Scatchard analysis of [$^{125}$I] galanin binding to the membranes from CHO cells transformed with the mouse galanin receptor cDNA. Membrane fractions (1 μg of protein) were incubated with increasing concentrations of porcine [$^{125}$I] galanin for 75 min at 25° C. The results shown are from one representative experiment performed in triplicate assays. Each symbol represents the mean value ±S.E.M. The values for $K_d$ and $B_{MAX}$ were 45 pM and 5 pmol/mg protein, respectively. B, [$^{125}$I] galanin bound (pmol/mg protein), B/F, bound to free ratio (pmol/mg protein·nM).

Figure 18:
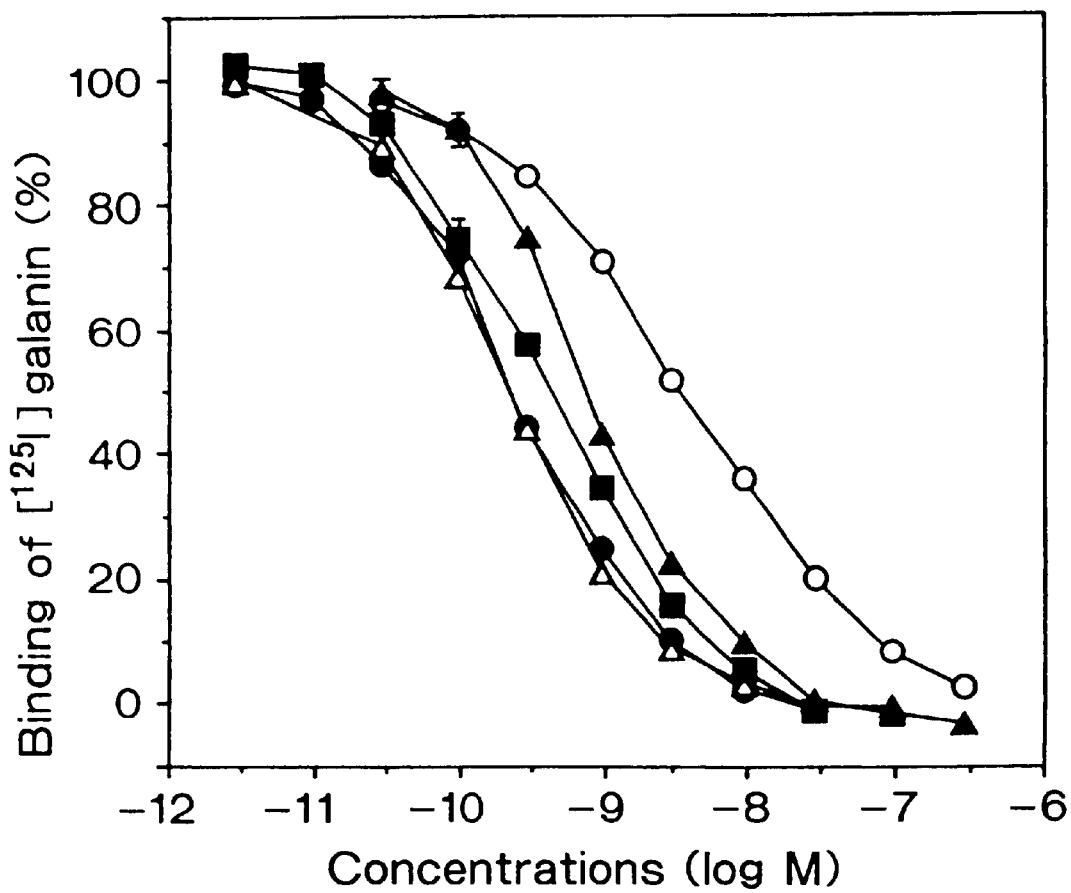

FIG. 18 illustrates a result of competitive experiments on the binding of porcine [$^{125}$I] galanin to mouse galanin receptor. Competitions to the porcine [$^{125}$I] galanin (100 pM at final concentrations) bindings were examined with unlabeled porcine (Δ), rat (●), human (■) galanins, galanin (1–16) (○), and M15 (▼). Membrane fractions (1 μg of protein) were incubated with the ligands for 75 min at 25° C. The amounts of [$^{125}$I] galanin bound were expressed as percentages against the control. Each symbol represents the mean value±S.E.M. of the triplicate assays. IC$_{50}$ values were 0.25±0.03 nM (porcine galanin), 0.25±0.01 nM (rat galanin), 0.43±0.03 nM (human galanin), 0.83±0.01 nM (M15), and 3.6±0.04 nM [galanin-(1–16)], respectively.

Figure 19:
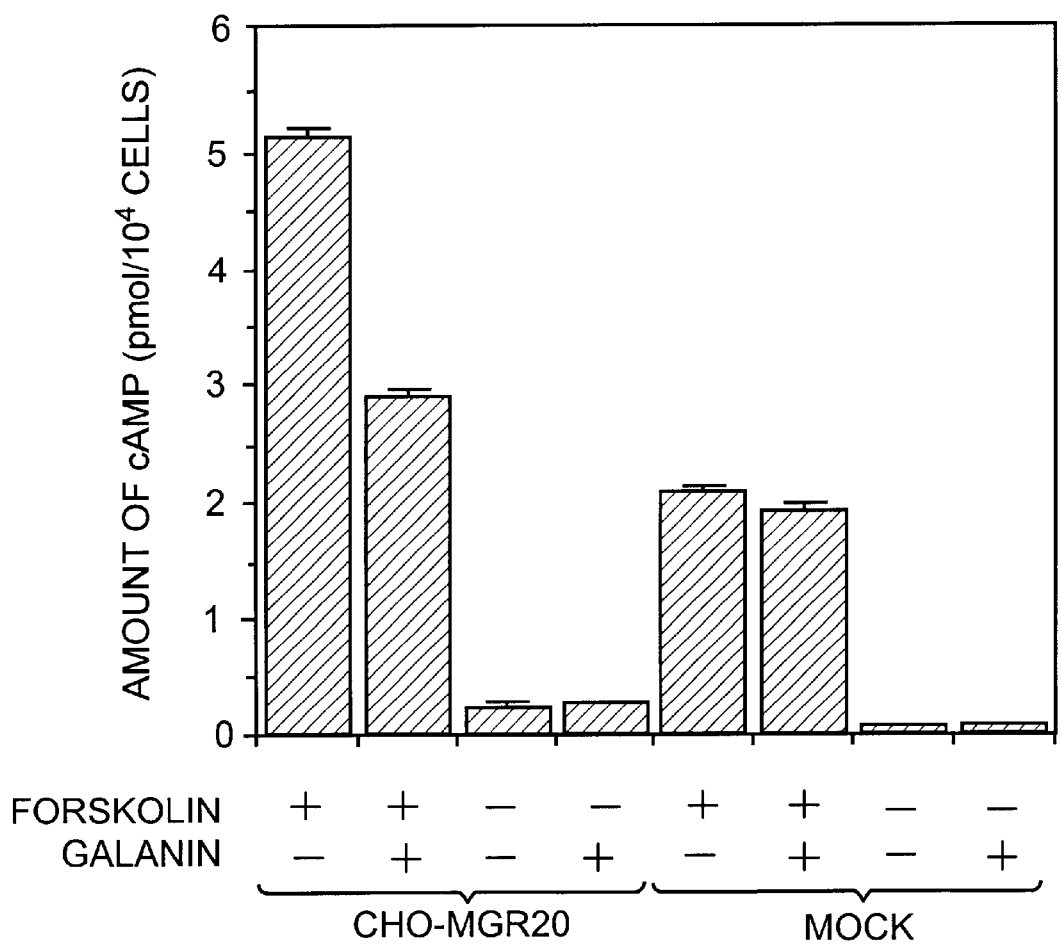

FIG. 19 shows a galanin receptor-mediated inhibition of forskolin-stimulated CAMP production. CHO-MGR20 or mock transformed CHO cells were incubated with forskolin (10 μM) and porcine galanin (0.1 μM) at 37° C. for 30 min. The reaction was terminated by extracting the cells with ice-cold ethanol. The amounts of intracellular cAMP were quantitated by EIA. Values indicated are mean±S.E.M. in triplicate assays.

DETAILED DESCRIPTION OF THE PREFERRED EMBODIMENT

According to the present invention, galanin receptor proteins and partial peptides thereof or salts thereof; DNAs comprising a DNA coding for said galanin receptor protein or its partial peptide; vectors carrying said DNA; transformants harboring said vector; cell membrane fractions obtained from said transformant; processes for producing said receptor protein or its partial peptide, or a salt thereof; methods for measuring the physiological actions of galanin using the galanin receptor protein (including a cell membrane fraction containing the receptor protein) or a galanin receptor protein-expressing cell (including the transformant); screening methods for a galanin receptor agonist/antagonist using the galanin receptor protein or a galanin receptor protein-expressing cell (including the transformant); kits for said screening; agonists or antagonists, obtained by said screening method; pharmaceutical compositions containing said agonist or antagonist; antibodies against said receptor protein; immunoassays using said receptor protein or said antibody; use of said receptor protein and encoding DNA; etc. may be successfully provided. For example, template DNAs coding for part or all of the polypeptide sequence of galanin receptor protein, can be successfully obtained and various DNA sequences encoding part or all of the polypeptide sequence of galanin receptor protein can be isolated and characterized. Further, galanin receptor proteins, partial peptides derived from the galanin receptor protein, modified derivatives or analogues thereof, and salts thereof are recognized, predicted, deduced, produced, expressed, isolated and characterized. More specifically, DNA sequences comprising each a nucleotide sequence indicated by a SEQ ID NO selected from the group consisting of SEQ ID NO: 3, SEQ ID NO: 4 and SEQ ID NO: 6 have been isolated and characterized. Galanin receptor proteins comprising each part or all of an amino acid sequence selected from the group consisting of an amino acid sequence represented by SEQ ID NO: 1, SEQ ID NO: 2 or SEQ ID NO: 5 and its substantial equivalents thereto, or a salt thereof.

These galanin receptor proteins are those derived from all cells and tissues (e.g. amygdaloid nucleus, pituitary gland, pancreas, brain (including whole brain, midbrain nigra and other regions), kidney, liver, gonad, thyroid gland, cholecyst, bone marrow, adrenal, skin, muscle, lung, digestive duct, stomach, blood vessel, heart, thymus, spleen, leukocyte, etc.) of warm-blooded animals (e.g. guinea pig, rat, mouse, swine, sheep, cattle, horse, monkey, human being, rabbit, cat, dog, etc.), and any of galanin receptor proteins as long as they comprise an amino acid sequence selected from the group consisting of an amino acid sequence represented by SEQ ID NO: 1, an amino acid sequence represented by SEQ ID NO: 2, an amino acid sequence represented by SEQ ID NO: 5, and substantial equivalents to the amino acid sequence represented by SEQ ID NO: 1, SEQ ID NO: 2, or SEQ ID NO: 5. These galanin receptor proteins may include proteins having an amino acid sequence selected from the group consisting of an amino acid sequence represented by SEQ ID NO: 1, an amino acid sequence represented by SEQ ID NO: 2, and an amino acid sequence represented by SEQ ID NO: 5, proteins wherein the amino acid sequence thereof is about 90% to 99.9% homologous to an amino acid sequence represented by SEQ ID NO: 1, an amino acid sequence represented by SEQ ID NO: 2 or an amino acid sequence represented by SEQ ID NO: 5 and the activity thereof is substantially equivalent to the protein having an amino acid sequence represented by SEQ ID NO: 1, an amino acid sequence represented by SEQ ID NO: 2 or an amino acid sequence represented by SEQ ID NO: 5 and the like. The substantially equivalent activity may include ligand binding activity, signal information transmitting, etc. The term "substantially equivalent" or "substantial equivalent" means that the nature of the ligand binding activity and the like is equivalent. Therefore, it is allowable that even differences among grades such as ligand binding affinity grades and ligand binding activity grades and quantitative factors such as molecular weights of receptor proteins are present.

In one embodiment of the present invention, mouse-derived galanin receptor proteins are those derived from all mouse-derived cells and tissues (e.g. amygdaloid nucleus, pituitary gland, pancreas, brain, kidney, liver, gonad, thyroid gland, cholecyst, bone marrow, lung, digestive duct, blood vessel, heart, thymus, spleen, leukocyte, etc.), and any of proteins as long as they comprise an amino acid sequence represented by SEQ ID NO: 1, and substantial equivalents thereto. The mouse-derived galanin receptor proteins may include proteins having an amino acid sequence represented by SEQ ID NO: 1, proteins wherein the amino acid sequence thereof is about 90% to 99.9% homologous to an amino acid sequence represented by SEQ ID NO: 1 and the activity thereof is substantially equivalent to the protein having an amino acid sequence represented by SEQ ID NO: 1 and the like. The substantially equivalent activity may include ligand binding activity, signal information transmitting, etc. The term "substantially equivalent" or "substantial equivalent" means that the nature of the ligand binding activity and the like is equivalent. Therefore, it is allowable that even differences among grades such as ligand binding affinity grades and ligand binding activity grades and quantitative factors such as molecular weights of receptor proteins are present.

In another embodiment of the present invention, mouse-derived galanin receptor proteins include mouse pancreatic β-cell line, MIN6 (FERM BP-4954)-derived galanin receptor proteins comprising an amino acid sequence represented by SEQ ID NO: 1, etc. Examples of the mouse-derived galanin receptor protein are mouse-derived galanin receptor proteins having an amino acid sequence represented by SEQ ID NO: 1, proteins wherein one or more amino acid residues (preferably from 1 to 30 amino acid residues, more preferably from 1 to 10 amino acid residues) are deleted from the amino acid sequence of SEQ ID NO: 1, proteins wherein one or more amino acid residues (preferably from 1 to 30 amino acid residues, more preferably from 1 to 10 amino acid residues) are added to the amino acid sequence of SEQ ID NO: 1, proteins wherein one or more amino acid residues (preferably from 1 to 30 amino acid residues, more preferably from 1 to 10 amino acid residues) in the amino acid sequence of SEQ ID NO: 1, are substituted with one or more amino acid residues, etc.

More specific examples of the mouse-derived galanin receptor protein are mouse pancreatic β-cell line, MIN6-derived galanin receptor proteins having an amino acid sequence represented by SEQ ID NO: 2, proteins having a substantial amino acid sequence thereto (for example, the amino acid sequence thereof is about 90% to 99.9% homologous to an amino acid sequence represented by SEQ ID NO: 2), proteins wherein one or more amino acid residues (preferably from 1 to 30 amino acid residues, more preferably from 1 to 10 amino acid residues) are deleted from the amino acid sequence of SEQ ID NO: 2, proteins wherein one or more amino acid residues (preferably from 1 to 30 amino acid residues, more preferably from 1 to 10 amino acid residues) are added to the amino acid sequence of SEQ ID NO: 2, proteins wherein one or more amino acid residues (preferably from 1 to 30 amino acid residues, more preferably from 1 to 10 amino acid residues) in the amino acid sequence of SEQ ID NO: 2, are substituted with one or more amino acid residues, etc.

In yet another embodiment of the present invention, human galanin receptor proteins are those derived from all human-derived cells and tissues (e.g. stomach, pituitary gland, pancreas, brain (including whole brain, midbrain nigra and other regions), kidney, liver, gonad, thyroid gland, cholecyst, bone marrow, adrenal, skin, muscle, lung, digestive duct, blood vessel, heart, etc.), and any of proteins as long as they comprise an amino acid sequence represented by SEQ ID NO: 5, and substantial equivalents thereto. The human galanin receptor proteins may include proteins having an amino acid sequence represented by SEQ ID NO: 5, proteins wherein the amino acid sequence thereof is about 90% to 99.9% homologous to an amino acid sequence represented by SEQ ID NO: 5 and the activity thereof is substantially equivalent to the protein having an amino acid sequence represented by SEQ ID NO: 5 and the like. The substantially equivalent activity may include ligand binding activity, signal information transmitting, etc. The term "substantially equivalent" or "substantial equivalent" means that the nature of the ligand binding activity and the like is equivalent. Therefore, it is allowable that even differences among grades such as ligand binding affinity grades and ligand binding activity grades and quantitative factors such as molecular weights of receptor proteins are present.

In another embodiment of the present invention, human galanin receptor proteins include human-derived galanin receptor proteins comprising an amino acid sequence represented by SEQ ID NO: 5, etc. Examples of the human galanin receptor protein are human-derived galanin receptor proteins having an amino acid sequence represented by SEQ ID NO: 5, proteins wherein one or more amino acid residues (preferably from 1 to 20 amino acid residues, more preferably from 1 to 10 amino acid residues) are deleted from the amino acid sequence of SEQ ID NO: 5, proteins wherein one or more amino acid residues (preferably from 1 to 20 amino acid residues, more preferably from 1 to 10 amino acid residues) are added to the amino acid sequence of SEQ ID NO: 5, proteins wherein one or more amino acid residues (preferably from 1 to 20 amino acid residues, more preferably from 1 to 10 amino acid residues) in the amino acid sequence of SEQ ID NO: 5, are substituted with one or more amino acid residues, etc.

A portion of the amino acid sequence may be modified (e.g. addition, deletion, substitution with other amino acids, etc.) in the galanin receptor proteins of the present invention.

Furthermore, the galanin receptor proteins of the present invention includes those wherein N-terminal Met is protected with a protecting group (e.g., $C_{1-6}$ acyl group such as formyl, acetyl, etc.), those wherein the N-terminal side of Glu is cleaved in vivo to make said Glu pyroglutaminated, those wherein the intramolecular side chain of amino acids is protected with a suitable protecting group (e.g., $C_{1-6}$ acyl group such as formyl, acetyl, etc.), conjugated proteins such as so-called "glycoproteins" wherein saccharide chains are bonded, etc.

However, the known human galanin receptor protein having an amino acid sequence in which the fifteenth Trp in the amino acid sequence represented by SEQ ID NO: 5 is substituted with Cys is excluded from the coverage of the human galanin receptor protein of the present invention.

The salt of said galanin receptor protein of the present invention includes preferably physiologically acceptable acid addition salts. Examples of such salts are salts thereof with inorganic acids (e.g. hydrochloric acid, phosphoric acid, hydrobromic acid, sulfuric acid, etc.), salts thereof with organic acids (e.g. acetic acid, formic acid, propionic acid, fumaric acid, maleic acid, succinic acid, tartaric acid, citric acid, maleic acid, oxalic acid, benzoic acid, methanesulfonic acid, benzenesulfonic acid, etc.), etc.

The galanin receptor protein or its salt of the present invention may be manufactured from the tissues or cells of warm-blooded animals by purifying methods which are known per se by those skilled in the art or methods similar thereto or may be manufactured by culturing the transformant (or transfectant) (as described herein below) containing galanin receptor protein encoding DNA. The protein or its salt of the present invention may be manufactured by the peptide synthesis as described herein below.

The galanin receptor protein fragment (the partial peptide of said galanin receptor protein) may include, for example, the site which is exposed outside cell membranes, among the galanin receptor protein molecule. Examples of the partial peptide are peptides containing a region which is analyzed as an extracellular area (hydrophilic region or site) in a hydrophobic plotting analysis on the galanin receptor protein. A peptide which partly contains a hydrophobic region or site may be used as well. Further, a peptide which separately contains each domain may be used too although the partial peptide (or peptide fragment) which contains plural domains at the same time will be used as well.

Figure 2:
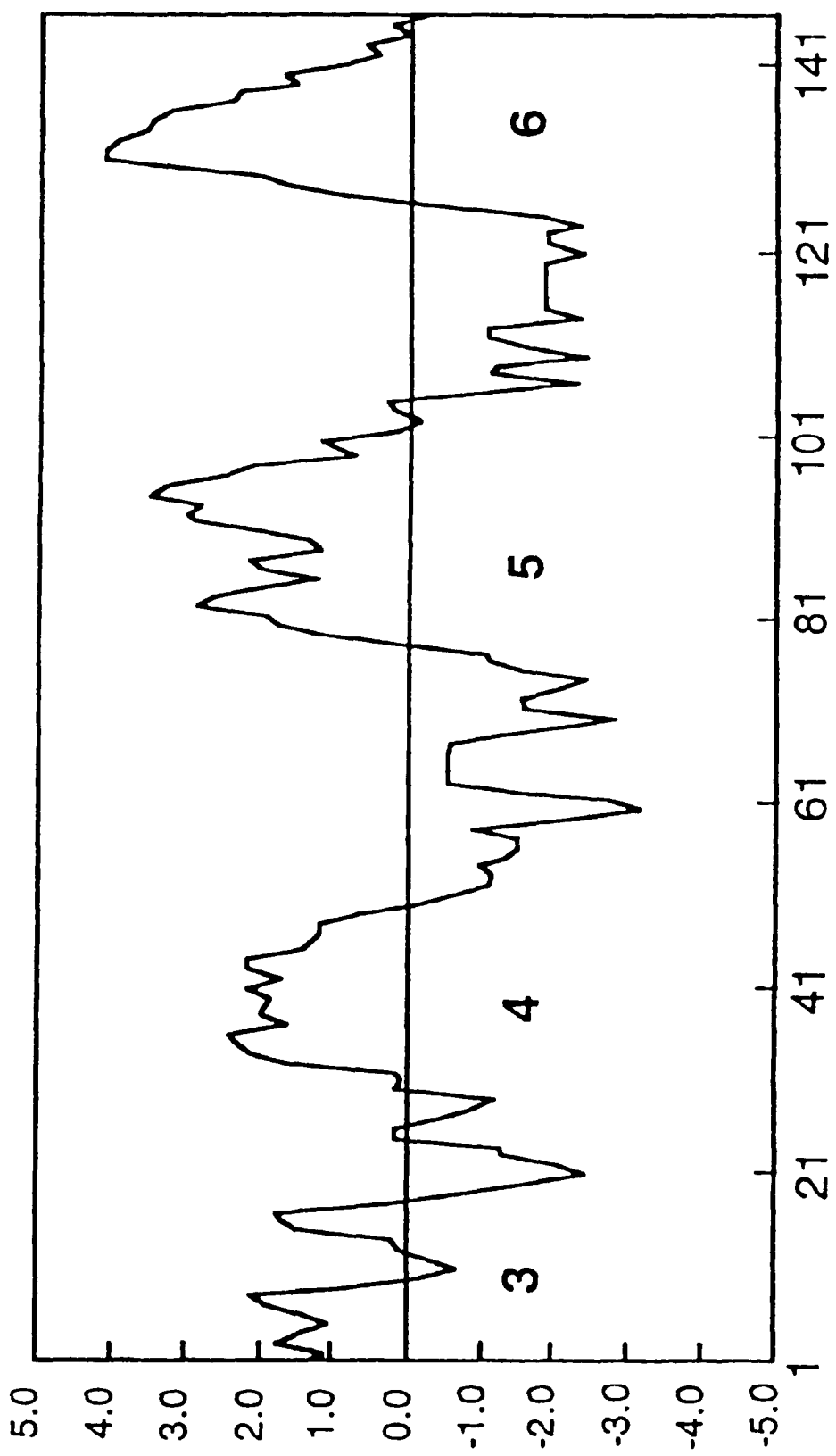
FIG. 2 is the hydrophobicity plotting profile, prepared based upon the amino acid sequence shown in FIG. 1, wherein the axis of ordinate represents an index of hydrophobicity, the axis of abscissa represents the number of amino acids and numerals 3 to 6 represent the presence of hydrophobic domains.
Figure 5:
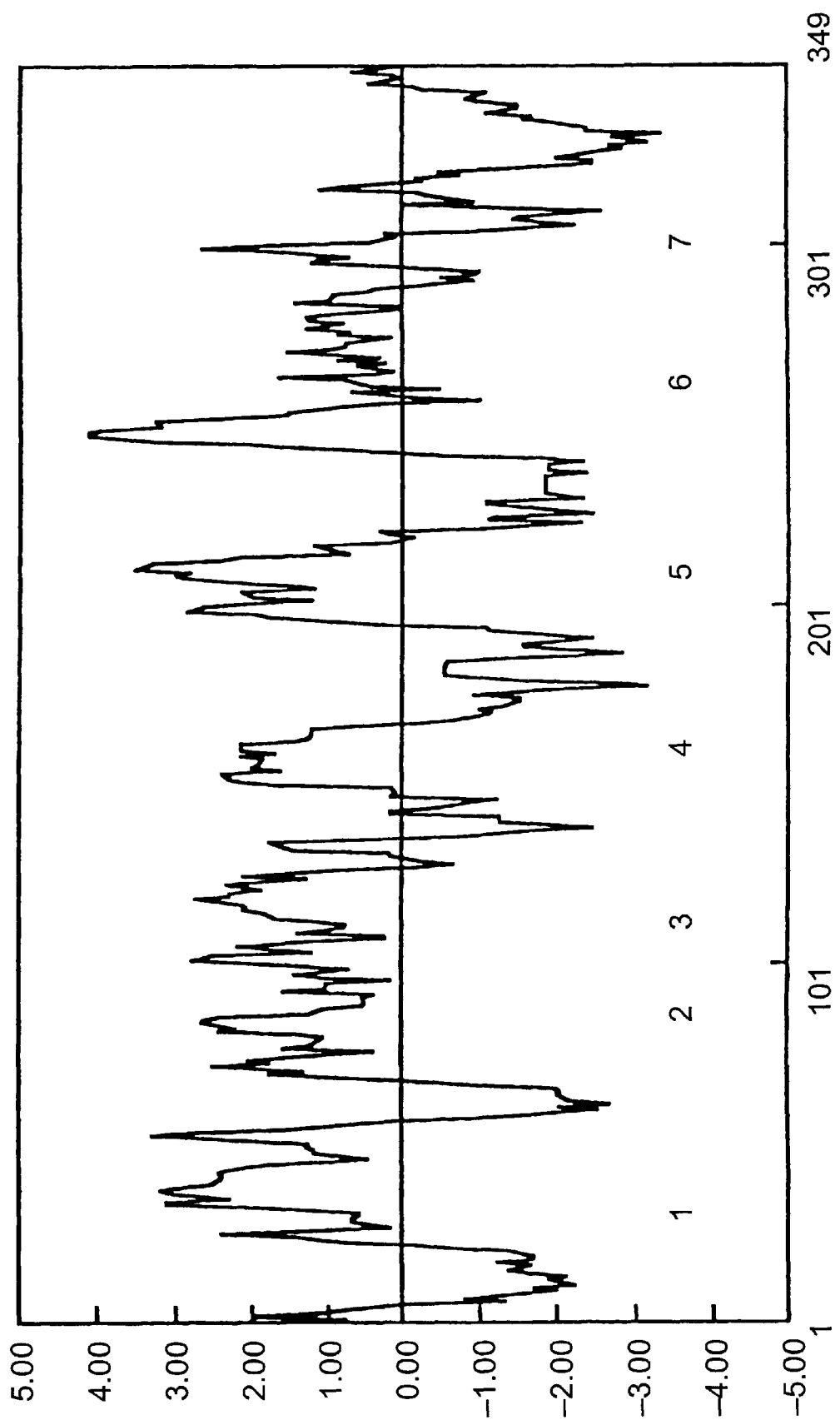
FIG. 5 is the hydrophobicity plotting profile, prepared based upon the amino acid sequence shown in FIG. 4, wherein the axis of ordinate represents an index of hydrophobic property, the axis of abscissa represents the number of amino acids, and numerals 1 to 7 represent the presence of hydrophobic domains.

In an embodiment of the present invention, the partial peptide of said mouse-derived galanin receptor protein may include, for example, the site which is exposed outside cell membranes, among the galanin receptor protein molecule. Examples of the mouse-derived galanin receptor partial peptide are peptides containing a region which is analyzed as an extracellular area (hydrophilic region or site) in a hydrophobic plotting analysis on the galanin receptor protein, represented by FIG. 2.

The salt of said galanin receptor partial peptide includes preferably physiologically acceptable acid addition salts. Examples of such salts are salts thereof with inorganic acids (e.g. hydrochloric acid, phosphoric acid, hydrobromic acid, sulfuric acid, etc.), salts thereof with organic acids (e.g. acetic acid, formic acid, propionic acid, fumaric acid, maleic acid, succinic acid, tartaric acid, citric acid, maleic acid, oxalic acid, benzoic acid, methanesulfonic acid, benzenesulfonic acid, etc.), etc.

The partial peptide of the galanin receptor protein may be manufactured by synthesizing methods for peptides which are known per se by those skilled in the art or methods similar thereto or by cleaving (digesting) galanin receptor proteins by a suitable peptidase. Methods of synthesizing peptide may be any of a solid phase synthesis and a liquid phase synthesis. Thus, a partial peptide (peptide fragment) or amino acids which can construct the protein of the present invention is condensed with the residual part thereof and, when the product has a protective group, said protective group is detached whereupon a desired peptide can be manufactured. Examples of the known methods for condensation and for detachment of protective groups include the following ① to ⑤:

① M. Bodanszky and M. A. Ondetti: Peptide Synthesis, Interscience Publishers, New York (1966).

② Schroeder and Luebke: The Peptide, Academic Press, New York, (1965).

③ Nobuo Izumiya et al.: Fundamentals and Experiments of the Peptide Synthesis, Maruzen KK, Japan (1975).

④ Haruaki Yajima and Shumpei Sakakibara: "Seikagaku Jikken Koza 1" (Experiments of Biochemistry, Part 1), "Tanpakusitu No Kagaku IV" (Chemistry of Protein, IV), p.205 (1977), Japan.

⑤ Haruaki Yajima (ed): Development of Pharmaceuticals (Second Series), Vol. 14, Peptide Synthesis, Hirokawa Shoten, Japan.

After the reaction, conventional purifying techniques such as salting-out, extraction with solvents, distillation, column chromatography, liquid chromatography, electrophoresis, recrystallization, etc. are optionally combined so that the protein of the present invention can be purified and isolated. When the protein obtained as such is a free compound, it may be converted to a suitable salt by known methods while, when it is obtained as a salt, the salt may be converted to a free compound or other salt compounds by known methods.

Furthermore, the product may be manufactured by culturing the transformant (transfectant) containing the DNA coding for said partial peptide.

The galanin receptor protein-encoding DNA of the present invention may be any coding DNA as long as it contains a nucleotide sequence coding for a galanin receptor protein which contains an amino acid sequence substantially equivalent to the amino acid sequence having SEQ ID NO: 1, SEQ ID NO: 2 or SEQ ID NO: 5 and/or which has an activity substantially equivalent to the amino acid sequence having SEQ ID NO: 1, SEQ ID NO: 2 or SEQ ID NO: 5, provided that the known galanin receptor protein wherein 15th Trp in the amino acid sequence of SEQ ID NO: 5 is replaced with Cys is excluded.

The DNA of the present invention may be any one of a genome DNA, a genome DNA library, a tissue and cell-derived cDNA, a tissue and cell-derived cDNA library and a synthetic DNA. The vector used for the library may include bacteriophage, plasmid, cosmid, phagemid, etc. The DNA can be further amplified directly by the reverse transcriptase polymerase chain reaction (hereinafter briefly referred to as "RT-PCR") using mRNA fractions prepared from tissues and cells.

In an embodiment, the DNA coding for the mouse-derived galanin receptor protein may be any coding DNA as long as it contains a nucleotide sequence coding for a mouse-derived galanin receptor protein which contains an amino acid sequence substantially equivalent to the amino acid sequence having SEQ ID NO: 1 and/or which has an activity substantially equivalent to the amino acid sequence having SEQ ID NO: 1. Examples of the DNA coding for the mouse-derived galanin receptor protein comprising the amino acid sequence of SEQ ID NO: 1 includes DNA having a nucleotide sequence represented by SEQ ID NO: 3, etc. The DNA coding for the mouse-derived galanin receptor protein comprising the amino acid sequence of SEQ ID NO: 2 includes DNA having a nucleotide sequence represented by SEQ ID NO: 4, etc.

In another embodiment, the DNA coding for the human galanin receptor protein may be any coding DNA as long as it contains a nucleotide sequence coding for a human-derived galanin receptor protein which contains an amino acid sequence substantially equivalent to the amino acid sequence having SEQ ID NO: 5 and/or which has an activity substantially equivalent to the amino acid sequence having SEQ ID NO: 5, provided that the known human galanin receptor protein wherein 15th Trp in the the amino acid sequence of SEQ ID NO: 5 is replaced with Cys is excluded. Examples of the DNA coding for the human galanin receptor protein comprising the amino acid sequence of SEQ ID NO: 5 includes DNA having a nucleotide sequence represented by SEQ ID NO: 6, etc.

The DNA completely coding for the galanin receptor protein of the present invention can be cloned by (1) carrying out the PCR amplification using a synthetic DNA primer having a partial nucleotide sequence (nucleotide fragment) of the galanin receptor protein; or (2) effecting the selection of a DNA constructed in a suitable vector, based on the hybridization with a labeled DNA fragment having part or all of the region encoding a galanin receptor protein (e.g., human galanin receptor protein, etc.) or a labeled synthetic DNA having part or all of the coding region thereof. The hybridization is carried out according to methods as disclosed in, for example, Molecular Cloning, 2nd Ed., J. Sambrook et al., Cold Spring Harbor Lab. Press, 1989. When a DNA library commercially available in the market is used, the hybridization is carried out according to protocols or manuals attached thereto.

For example, the DNA completely coding for the mouse-derived galanin receptor protein of the present invention is cloned by (1) carrying out the PCR amplification using a synthetic DNA primer having a partial nucleotide sequence (nucleotide fragment) of the mouse-derived galanin receptor protein; or (2) effecting the selection of a DNA constructed in a suitable vector, based on the hybridization with a labeled DNA fragment having part or all of the region encoding a human or mouse-derived galanin receptor protein or a labeled synthetic DNA having part or all of the coding region thereof.

The cloned galanin receptor protein-encoding DNA of the present invention can be used as it is, or can be used, as desired, after modifications including digestion with a restriction enzyme or addition of a linker or adapter, etc. depending upon objects. The DNA may have an initiation codon, ATG, on the 5' terminal side and a termination codon, TAA, TGA or TAG, on the 3' terminal side. These initiation and termination codons can be ligated by using a suitable synthetic DNA adapter.

A vector containing the galanin receptor protein-encoding DNA (for example, an expression vector for the galanin receptor protein; specifically, an expression plasmid comprising the human galanin receptor protein-encoding DNA, etc.) can be produced by, for example, (a) cutting out a target DNA fragment from the galanin receptor protein-encoding DNA of the present invention and (b) ligating the target DNA fragment with the downstream site of a promoter in a suitable expression vector (for example, an expression plasmid compatible with the human galanin receptor protein-encoding DNA, etc.).

The vector may include plasmids derived from *Escherichia coli* (e.g., pBR322, pBR325, pUC12, pUC13, etc.), plasmids derived from *Bacillus subtilis* (e.g., pUB110, pTP5, pC194, etc.), plasmids derived from yeasts (e.g., pSH19, pSH15, etc.), bacteriophages such as λ-phage, and animal virus such as retrovirus, vaccinia virus and baculovirus.

According to the present invention, any promoter can be used as long as it is compatible with a host which is used for expressing a gene. When the host for the transformation is *E. coli*, the promoters are preferably trp promoters, lac promoters, recA promoters, $\lambda_{PL}$ promoters, 1pp promoters, etc. When the host for the transformation is the Bacillus, the promoters are preferably SPO1 promoters, SPO2 promoters, penP promoters, etc. When the host is an yeast, the promoters are preferably PHO5 promoters, PGK promoters, GAP promoters, ADH promoters, etc. When the host is an animal cell, the promoters include SV40-derived promoters, retrovirus promoters, metallothionein promoters, heat shock promoters, cytomegalovirus (CMV) promoters, SRα promoters, etc. An enhancer can be effectively utilized for the expression.

As required, furthermore, a host-compatible signal sequence is added to the N-terminal side of the galanin receptor protein. When the host is *E. coli*, the utilizable signal sequences may include alkaline phosphatase signal sequences, OmpA signal sequences, etc. When the host is the Bacillus, they may include α-amylase signal sequences, subtilisin signal sequences, etc. When the host is an yeast, they may include mating factor α signal sequences, invertase signal sequences, etc. When the host is an animal cell, they may include insulin signal sequences, α-interferon signal sequences, antibody molecule signal sequences, etc.

Further, a preferred method of constructing an expression plasmid among the vectors containing the human galanin receptor protein DNA of the present invention will be concretely given as hereunder.

Examples of the plasmid used are pAKKO-111 (sometimes referred to as pA1-11), pRc/CMV, pRc/RSV, etc. and, among them, the use of pAKKO-111 (pA1-11) is preferred. With respect to a promoter, anything may be used so far as it functions in an effective manner in host cells and its examples are SV40 early gene promoter, CMV promoter, HSV-TK promoter, SRα promoter, RSV promoter, etc. Among them, CMV promoter and SRα promoter are preferred and the use of SRα promoter is particularly preferred.

With respect to an expression plasmid, the use of the agent containing an enhancer, a splicing signal, a poly A adding signal, a selective marker, etc. besides the above-mentioned ones is preferred. Examples of the selective marker are dihydrofolate reductase (hereinafter, sometimes referred to as "dhfr") gene and neomycin phosphate transferase (hereinafter, sometimes referred to as "neo" gene). The dhfr gene gives a resistance to methotrexate (MTX) while the neo gene gives a resistance to G-418. Especially when a dhfr gene-deficient CHO cell is used and a dhfr gene is utilized as a selective marker, it is possible to select even by a medium free from thymidine.

Specific and preferred examples of the expression plasmid carrying the human galanin receptor protein encoding DNA of the present invention are those in which the above-mentioned promoters (e.g., particularly, SRα-promoter, etc.) are inserted in the upstream of the human galanin receptor protein DNA and, preferably, an SV early gene poly A addition signal is inserted to the downstream of the human galanin receptor protein DNA followed by inserting dhfr gene, ampicillin-resisting gene, etc. into the downstream of the poly A addition signal.

More specific and preferred example is an expression plasmid designated pTS863 (FIG. 13) in which SRα promoter is inserted in an upstream of the human galanin receptor protein DNA, an SV early gene poly A addition signal is inserted in a downstream of the human galanin receptor protein DNA, a dhfr gene is inserted in a downstream thereof and then an ampicillin-resisting gene is inserted in the downstream thereof, etc.

When the expression plasmid containing the human galanin receptor protein DNA prepared as such is introduced into a host cell, it is possible to produce a cell which is able to highly express the DNA which codes for the human galanin receptor protein.

A transformant or transfectant is produced by using the vector thus constructed, which carries the galanin receptor protein-encoding DNA of the present invention. The host may be, for example, Escherichia microorganisms, Bacillus microorganisms, yeasts, insect cells, animal cells, etc. Examples of the Escherichia and Bacillus microorganisms include *Escherichia coli* K12-DH1 [Proc. Natl. Acad. Sci. USA, Vol. 60, 160 (1968)], JM103 [Nucleic Acids Research, Vol. 9, 309 (1981)], JA221 [Journal of Molecular Biology, Vol. 120, 517 (1978)], HB101 [Journal of Molecular Biology, Vol. 41, 459 (1969)], C600 [Genetics, Vol. 39, 440 (1954)], etc. Examples of the Bacillus microorganism are, for example, *Bacillus subtilis* MI114 [Gene, Vol. 24, 255 (1983)], 207–21 [Journal of Biochemistry, Vol. 95, 87 (1984)], etc. The yeast may be, for example, *Saccharomyces cerevisiae* AH22, AH22R⁻, NA87-11A, DKD-5D, 20B-12, etc. The insect may include a silkworm (*Bombyx mori* larva), [Maeda et al, Nature, Vol. 315, 592 (1985)] etc. The host animal cell may be, for example, monkey-derived cell line, COS-7, Vero, Chinese hamster ovary cell line (CHO cell), DHFR gene-deficient Chinese hamster cell line (dhfr⁻CHO cell), CHO K-1, human FL cell, 293 cell, L cell, myeloma cell, C127 cell, Balb/c3T3 cell, Sp-2/O cell, etc.

Depending on the host cell used, transformation is done using standard techniques appropriate to such cells. Transformation of Escherichia microorganisms can be carried out in accordance with methods as disclosed in, for example, Proc. Natl. Acad. Sci. USA, Vol. 69, 2110 (1972), Gene, Vol. 17, 107 (1982), etc. Transformation of Bacillus microorganisms can be carried out in accordance with methods as disclosed in, for example, Molecular & General Genetics, Vol. 168, 111 (1979), etc. Transformation of the yeast can be carried out in accordance with methods as disclosed in, for example, Proc. Natl. Acad. Sci. USA, Vol. 75, 1929 (1978), etc. The insect cells can be transformed in accordance with methods as disclosed in, for example, Bio/Technology, 6, 47–55, 1988. The animal cells can be transformed by methods as disclosed in, for example, Virology, Vol. 52, 456, 1973, etc. The transformants or transfectants harboring the expression vector carrying a galanin receptor protein-encoding DNA are produced according to the aforementioned techniques.

Among the above-mentioned host cells, animal cells are particularly preferred as the host cell for an expression plasmid containing the human galanin receptor protein DNA of the present invention. The examples thereof are 293 cell, CHO cell, Vero cell, L cell, myeloma cell, C127 cell, Balb/c3T3 cell and Sp-2/O cell, etc. Among them, CHO cell and 293 cell are preferred and particularly CHO cell [Journal of Experiment of Medicine, 108, 945(1958)] is more preferred. Among said CHO cell, the preferred ones are dhfr gene-deficient CHO cell (hereinafter, sometimes referred to as CHO (dhfr⁻) cell) [Proceedings of the National Academy of Sciences of the U.S.A., 77, 4216–4220(1980)], CHO K-1 cell [Proceedings of the National Academy of Sciences of the U.S.A., 60, 1275(1968)], etc. When dhfr gene is inserted in an expression plasmid as a selective marker, CHO(dhfr⁻) and the like are suitable.

With respect to the combination of the expression plasmid with the host cell, the preferred one can be suitably selected and, for example, CHO(dhfr⁻) cell and the like are suitable as the host cell of the expression plasmid (FIG. 13) indicated by pTS863. In introducing the expression plasmid into animal cells, known methods such as a calcium phosphate method [Graham, F. L. and van der Eb, A. J.: Virology, 52, 456–467(1973)], an electroporation [Neumann, E. et al., EMBO Journal, 1, 841–845(1982)], etc. may be used.

As such, a transformant in which a transformation is carried out using a vector containing a human galanin receptor protein DNA is produced. In addition, the transformant prepared by a transformation using an expression plasmid containing the human galanin receptor protein DNA may be used for the manufacture of human galanin receptor protein.

Cells which are able to highly express the human galanin receptor protein can be obtained by selecting the cells wherein the above-mentioned expression plasmid is incorporated in the chromosome by means of clone selection. Briefly, the transformant is first selected using the above-mentioned selective marker as an index for selection. Then the transformant produced as such using the selective marker is repeatedly subjected to a clone selection to give a cell strain which stably exhibits a high ability of expressing the human galanin receptor protein. When a dhfr gene is used as a selective marker, the resisting cells are selected by a culture with a sequential increase in the methotrexate (MTX) concentration to amplify the introduced gene in the cells whereby a cell strain exhibiting far higher expression can be obtained.

Figure 13:
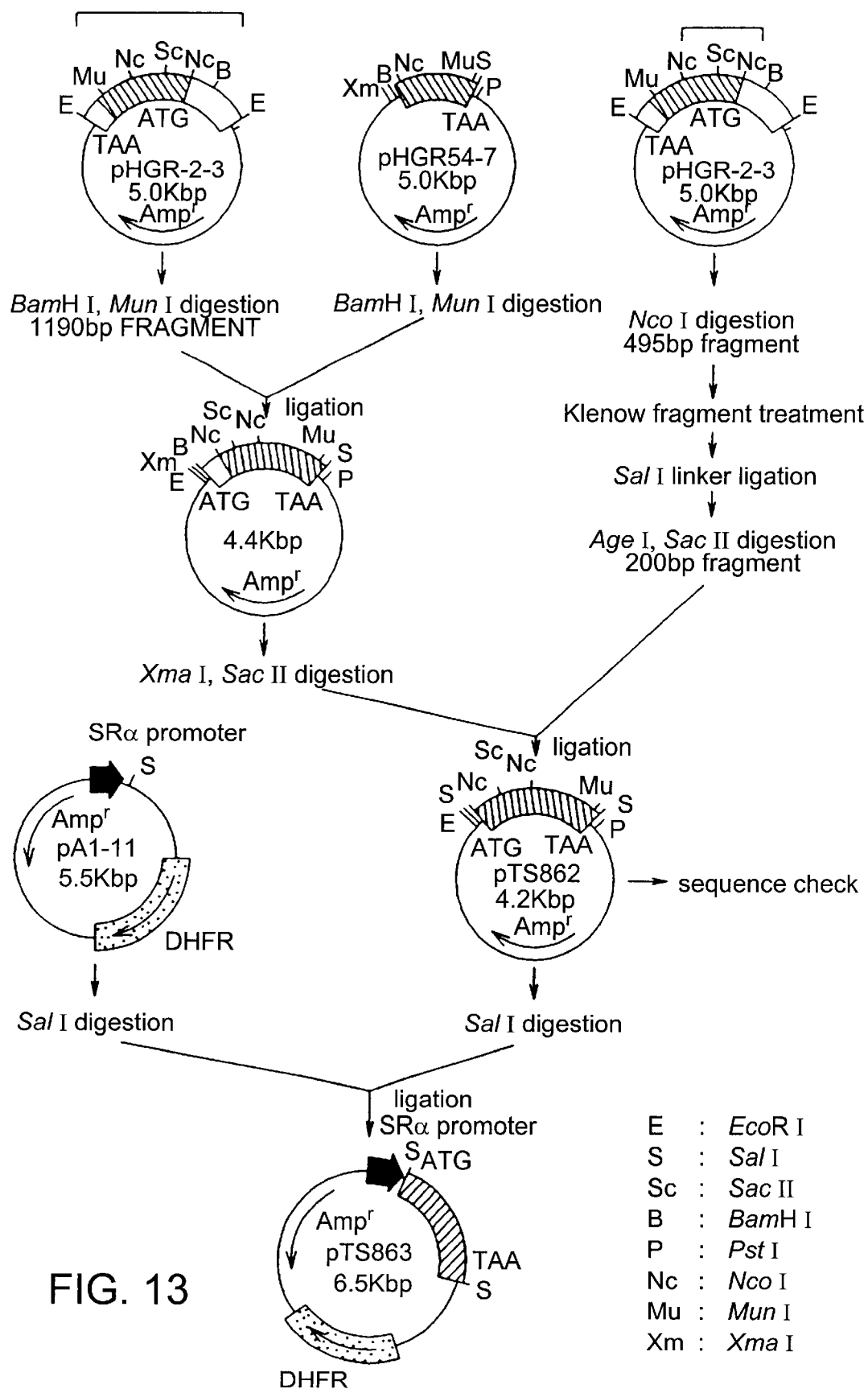
FIG. 13 is the construction of expression plasmid, pTS863, containing the human galanin receptor protein cDNA obtained in Example 12. The striped region of expression plasmid, pTS863, indicates the human galanin receptor protein cDNA. DHFR; dhfr gene and Amp$^r$; ampicillin resistant gene.

Even when CHO (dhfr$^-$) cell is used as a host, the CHO containing an expression plasmid indicated by pTS863 also has a dhfr gene as a result because a dhfr gene is introduced, for example, into an expression plasmid indicated by pTS863 (FIG. 13). In this specification, the CHO cell obtained by giving an expression plasmid (e.g. pTS 863, etc.) containing dhfr gene may be sometimes referred to as "CHO(dhfr$^+$) cell".

An example of the transformant which is able to highly express the human galanin receptor protein DNA in the present invention is a CHO (dhfr$^+$) cell obtained by giving an expression plasmid indicated by pTS863 obtained in Example 11 (mentioned herein later) to a CHO (dhfr$^-$) cell, etc. More specific examples are CHO (dhfr$^+$) cell indicated by CHO/pTS863-5, CHO (dhfr$^+$) cell indicated by CHO/pTS863-7, etc. As compared with the known human galanin receptor protein-expressing COS cells, the above-mentioned CHO (dhfr$^+$) cells are able to express more amount of human galanin receptor protein and, further, there are some which exhibit a receptor activity (e.g., ligand binding activity, etc.) of about 10 to 100-fold (preferably about 100-fold) as compared with natural tissues containing human galanin receptor proteins (e.g. human melanoma Bowes cells, etc.). Accordingly, those CHO (dhfr$^+$) cells are effective in conducting a method of screening for the human galanin receptor agonist/antagonist which will be mentioned herein later.

The cells which contain the human galanin receptor protein of the present invention can be also manufactured by culturing the transformant containing the vector (particularly, the expression plasmid) carrying the human galanin receptor protein DNA of the present invention under a condition where the human galanin receptor protein DNA can be expressed.

Cultivation of the transformant (transfectant) in which the host is Escherichia or Bacillus microorganism can be carried out suitably in a liquid culture medium. The culture medium may contains carbon sources, nitrogen sources, minerals, etc. necessary for growing the transformant. The carbon source may include glucose, dextrin, soluble starch, sucrose, etc. The nitrogen source may include organic or inorganic substances such as ammonium salts, nitrates, corn steep liquor, peptone, casein, meat extracts, bean-cakes, potato extracts, etc. Examples of the minerals may include calcium chloride, sodium dihydrogen phosphate, magnesium chloride, etc. It is further allowable to add yeasts, vitamins, growth-promoting factors, etc. It is desired that the culture medium is pH from about 5 to about 8.

The Escherichia microorganism culture medium is preferably an M9 medium containing, for example, glucose and casamino acid (Miller, Journal of Experiments in Molecular Genetics), 431–433, Cold Spring Harbor Laboratory, New York, 1972. Depending on necessity, the medium may be supplemented with drugs such as 3β-indolyl acrylic acid in order to improve efficiency of the promoter. In the case of the Escherichia host, the cultivation is carried out usually at about 15 to 43° C. for about 3 to 24 hours. As required, aeration and stirring may be applied. In the case of the Bacillus host, the cultivation is carried out usually at about 30 to 40° C. for about 6 to 24 hours. As required, aeration and stirring may be also applied. In the case of the transformant in which the host is an yeast, the culture medium used may include, for example, a Burkholder minimum medium [Bostian, K.L. et al., Proc. Natl. Acad. Sci. USA, Vol. 77, 4505 (1980)], an SD medium containing 0.5% casamino acid [Bitter, G. A. et al., Proc. Natl. Acad. Sci. USA, Vol. 81, 5330 (1984)], etc. It is preferable that pH of the culture medium is adjusted to be from about 5 to about 8. The cultivation is carried out usually at about 20 to 35° C. for about 24 to 72 hours. As required, aeration and stirring may be applied. In the case of the transformant in which the host is an insect, the culture medium used may include those obtained by suitably adding additives such as passivated (or immobilized) 10% bovine serum and the like to the Grace's insect medium (Grace, T.C.C., Nature, 195, 788 (1962)). It is preferable that pH of the culture medium is adjusted to be about 6.2 to 6.4. The cultivation is usually carried out at about 27° C. for about 3 to 5 days. As desired, aeration and stirring may be applied. In the case of the transformant in which the host is an animal cell, the culture medium used may include MEM medium [Science, Vol. 122, 501 (1952)], DMEM medium [Virology, Vol. 8, 396 (1959)], RPMI 1640 medium [Journal of the American Medical Association, Vol. 199, 519 (1967)], 199 medium [Proceedings of the Society for the Biological Medicine, Vol. 73, 1 (1950)], α-MEM medium, etc. which are containing, for example, about 5 to 20% of fetal calf serum. Especially when CHO (dhfr$^-$) cells and dhfr selective marker gene are used, it is preferred to use a DMEM medium containing a dialyzed fetal bovine serum which rarely contains thymidine. It is preferable that the pH is from about 6 to about 8. The cultivation is usually carried out at about 30 to 40° C. for about 15 to 72 hours. As required, medium exchange, aeration and stirring may be applied.

As such, cells containing the human galanin receptor protein can be manufactured from the transformant retaining the vector (particularly, expression plasmid) containing the human galanin receptor protein-encoding DNA. Examples of the cell containing the human galanin receptor protein are CHO cells containing the human galanin receptor protein and the like. The cells containing the human galanin receptor protein can be obtained by culturing CHO (dhfr$^+$) cell indicated by CHO/pTS863-5, CHO (dhfr$^+$) cell indicated by CHO/pTS863-7, etc.

Separation and purification of the galanin receptor protein (for example, human galanin receptor protein, etc.) from the above-mentioned cultures can be carried out according to methods described herein below.

To extract galanin receptor proteins from the cultured microorganisms or cells, the microorganisms or cells are collected by known methods after the cultivation, suspended in a suitable buffer solution, disrupted by ultrasonic waves, lysozyme and/or freezing and thawing, etc. and, then, a crude extract of the galanin receptor protein is obtained by centrifugation or filtration. Other conventional extracting or isolating methods can be applied. The buffer solution may contain a protein-denaturing agent such as urea or guanidine hydrochloride or a surfactant such as Triton X-100 (registered trademark, hereinafter often referred to as "TM").

In the case where galanin receptor proteins are secreted into culture media, supernatant liquids are separated from the microorganisms or cells after the cultivation is finished and the resulting supernatant liquid is collected by widely known methods. The culture supernatant liquid and extract containing galanin receptor proteins can be purified by suitable combinations of widely known methods for separation, isolation and purification. The widely known methods of separation, isolation and purification may include methods which utilizes solubility, such as salting out or sedimentation with solvents methods which utilizes chiefly a difference in the molecular size or weight, such as dialysis, ultrafiltration, gel filtration and SDS-polyacrylamide gel electrophoresis, methods utilizing a difference in the electric charge, such as ion-exchange chromatography, methods utilizing specific affinity such as affinity chromatography, methods utilizing a difference in the hydrophobic property, such as inverse-phase high-performance liquid chromatography, and methods utilizing a difference in the isoelectric point such as isoelectric electrophoresis, etc.

In case where the galanin receptor protein thus obtained is in a free form, the free protein can be converted into a salt thereof by known methods or method analogous thereto. In case where the galanin receptor protein thus obtained is in a salt form vice versa, the protein salt can be converted into a free form or into any other salt thereof by known methods or method analogous thereto.

The galanin receptor protein produced by the transformant can be arbitrarily modified or a polypeptide can be partly removed therefrom, by the action of a suitable protein-modifying enzyme before or after the purification. The protein-modifying enzyme may include trypsin, chymotrypsin, arginyl endopeptidase, protein kinase, glycosidase, etc. The activity of the galanin receptor protein thus formed can be measured by experimenting the coupling (or binding) with a ligand including galanin or by enzyme immunoassays (enzyme linked immunoassays) using specific antibodies.

When the DNA which codes for the known human galanin receptor protein is used in the above-mentioned means instead of that which codes for the human galanin receptor protein of the present invention, it is also possible to isolate the cells which highly express recombinant human galanin receptor protein or to isolate recombinant human galanin receptor protein.

Although the known human galanin receptor protein is expressed by COS cells, the expressed amount in the case of the COS cells are usually small. However, in accordance with a method of constructing the expression plasmid of the present invention, it is possible to manufacture not only the cells (particularly CHO cells) which highly express the human galanin receptor protein of the present invention but also the cells (particularly CHO cells) which highly express the known human galanin receptor protein.

The cell membrane fraction of a cell containing said galanin receptor protein (for example, cell membrane fraction of a cell containing human galanin receptor protein, cell membrane fraction of a cell containing mouse-derived galanin receptor protein, etc.) is a cell membrane-rich fraction which is prepared by methods per se known to those of skill in the art or methods similar thereto after disruption of cells containing the galanin receptor protein (for example, the human galanin receptor protein, the mouse-derived galanin receptor protein, etc.). Examples of cell disruption may include a method for squeezing cells using a Potter-Elvejem homogenizer, a disruption by a Waring blender or a Polytron (manufactured by Kinematica), a disruption by ultrasonic waves, a disruption via blowing out cells from small nozzles together with applying a pressure using a French press or the like, etc. In the fractionation of the cell membrane, a fractionation method by means of centrifugal force such as a fractional centrifugal separation and a density gradient centrifugal separation is mainly used. For example, disrupted cellular liquid is centrifuged at a low speed (500 rpm to 3,000 rpm) for a short period (usually, from about one to ten minutes), the supernatant liquid is further centrifuged at a high speed (15,000 rpm to 30,000 rpm) usually for 30 minutes to two hours and the resulting precipitate is used as a membrane fraction. Said membrane fraction contains a lot of the expressed galanin receptor protein (for example, the human galanin receptor protein, the mouse-derived galanin receptor protein, etc.) and a lot of membrane components such as phospholipids and membrane proteins derived from the cells.

The amount of the galanin receptor protein in the membrane fraction cell containing said galanin receptor protein is preferably $10^3$ to $10^8$ molecules per cell or, suitably, $10^5$ to $10^7$ molecules per cell. Incidentally, the more the expressed amount, the higher the ligand binding activity (specific activity) per membrane fraction whereby the construction of a highly sensitive screening system becomes possible and, moreover, it may enable us to measure a large amount of samples within the same lot.

The galanin receptor protein, the partial peptide thereof and the galanin receptor protein-encoding DNA of the present invention can be used for:

① obtaining an antibody and an antiserum,
② constructing a system for expressing a recombinant receptor protein,
③ developing a receptor-binding assay system using the above developing system and screening pharmaceutical candidate compounds,
④ designing drugs based upon the comparison with ligands and receptors which have a similar or analogous structure,
⑤ preparing a probe in the analysis of genes and preparing a PCR primer,
⑥ gene manipulating therapy,
⑦ producing a transgenic animal (for example, transgenic mouse, etc.),
⑧ producing a model animal suffering from diseases caused by gene deficiency, etc.

In particular, it is allowable to screen a galanin receptor agonist or antagonist specific to a warm-blooded animal such as human being by a receptor-binding assay system which uses a system for expressing a recombinant galanin receptor protein of the present invention. The agonist or antagonist thus screened or characterized permits various applications including prevention and/or therapy of a variety of diseases.

For example, the mouse-derived galanin receptor protein, the partial peptide of the mouse-derived galanin receptor protein and the DNA which codes for the mouse-derived galanin receptor protein can be used for ① obtaining antibody and antiserum; ② construction of an expression system of the recombinant receptor protein; ③ development of the receptor-binding assay system using said expression system and screening of the candidate compounds as pharmaceuticals; ④ conducting a drug design based upon a comparison with ligands and receptors which have a similar or analogous structure; ⑤ preparing probes and designing PCR primers in gene diagnosis; ⑥ gene therapy, etc.

The human galanin receptor protein, the partial peptide of the human galanin receptor protein and the DNA which codes for the human galanin receptor protein can be used for ① obtaining antibody and antiserum; ② construction of an expression system of the recombinant receptor protein; ③ development of the receptor-binding assay system using said expression system and screening of the candidate compounds as pharmaceuticals; ④ conducting a drug design based upon a comparison with ligands and receptors which have a similar or analogous structure; ⑤ preparing probes and designing PCR primers in gene diagnosis; ⑥ gene therapy, etc. Especially when the receptor binding assay system utilizing the expression system for the human galanin receptor protein of the present invention is used, it is possible to screen the galanin receptor agonist or antagonist which is specific to warm-blooded animals (especially, human being) whereupon said agonist or antagonist can be used as a preventive and therapeutic agent for various diseases.

Concretely described below are uses of galanin receptor proteins, partial peptides thereof (peptide fragments thereof), galanin receptor protein-encoding DNAs and antibodies against the galanin receptor protein according to the present invention.

(1) Quantitative Measurement of Galanin

The galanin receptor protein, a partial peptide thereof or a salt thereof has a binding property to galanin and, therefore, it is capable of determining quantitatively an amount of galanin in vivo with good sensitivity.

This quantitative measurement may be carried out by, for example, combining with a competitive method. Thus, samples to be measured is contacted with galanin receptor proteins or partial peptide thereof so that the galanin concentration in said sample can be measured. In one embodiment of the quantitative measurement, the protocols described in the following ① and ② or the methods similar thereto may be used:

① Hiroshi Irie (ed): "Radioimmunoassay" (Kodansha, Japan, 1974); and

② Hiroshi Irie (ed): "Radioimmunoassay, Second Series" (Kodansha, Japan, 1979).

Further, the quantitative determination method of galanin according to the present invention can be used as a diagnostic method for the diseases caused by increase/decrease in galanin concentrations such as stomach ulcer, diabetes and Alzheimer's disease.

(2) Screening of Galanin Receptor Agonist and/or Antagonist

Galanin receptor proteins or partial peptides thereof are used. Alternatively, expression systems for recombinant type galanin receptor proteins or partial peptides thereof are constructed and receptor binding assay systems using said expression system are used. In these assay systems, it is possible to screen compounds (e.g. peptides, proteins, non-peptidic compounds, synthetic compounds, fermented products, cell extracts, plant extracts, animal tissue extracts, etc.) or salts thereof which inhibits the binding of galanin with the galanin receptor protein. Such a compound includes a compound exhibiting a galanin receptor-mediated cell stimulating activity (e.g. activity of promoting or activity of inhibiting physiological reactions including liberation of arachidonic acid, liberation of acetylcholine, endocellular $Ca^{2+}$ liberation, endocellular cAMP production, endocellular cGMP production, production of inositol phosphate, changes in cell membrane potential, phosphorylation of endocellular proteins, activation of c-fos, lowering of pH, secretion of insulin, etc.; in particular, activity of promoting or activity of inhibiting endocellular cAMP production and secretion of insulin) (so-called "galanin receptor agonist"), a compound free of such a cell stimulating activity (so-called "galanin receptor antagonist"), etc.

Thus, the present invention provides a method of screening a galanin receptor agonist and/or galanin receptor antagonist with a galanin receptor protein or a salt thereof, characterized in comparing the following cases:

(i) the case wherein galanin is contacted with the galanin receptor protein or salt thereof, or a partial peptide thereof or a salt thereof; and (ii) the case wherein galanin is contacted with a mixture of the galanin receptor protein or salt thereof or the partial peptide or salt thereof and said test sample (including a test compound).

In said screening method, one characteristic feature of the present invention resides in that the amount of galanin bonded with said galanin receptor protein (for example, human or mouse-derived galanin receptor protein) or partial peptide thereof, the cell stimulating activity of galanin, etc. are measured in the case where (i) galanin is contacted with said galanin receptor protein (for example, human or mouse-derived galanin receptor protein) or its partial peptide and in the case where (ii) galanin and a test sample (including a test compound) are contacted with the galanin receptor protein or its partial peptide, respectively and then compared therebetween.

In the screening of the galanin receptor agonist or antagonist, it may be considered to use human hippocampus as a human galanin receptor protein source. However, tissues derived from human being are hardly available and, therefore, they are not suitable for use in screening whereupon recombinant human galanin receptor proteins which are abundantly expressed in cells (particularly, animal cells such as CHO cells) are suitable in practice. More preferably, the cell strain in which human galanin receptor proteins are continuously and stably expressed is advantageously used.

Accordingly, the human galanin receptor protein of the present invention or the salt thereof, the human galanin receptor protein-partial peptide of the present invention or the salt thereof and the cell or cell fraction thereof containing the human galanin receptor protein of the present invention are remarkably useful as a reagent for screening the galanin receptor agonist or antagonist.

Briefly, the present invention offers a method of screening galanin receptor agonist or antagonist, characterized in that, the human galanin receptor protein of the present invention or the salt thereof, the partial peptide of the human galanin receptor protein of the present invention or the salt thereof or the cells or cell fraction thereof containing the human galanin receptor protein of the present invention is used.

More specifically, the present invention offers:

(I) a method of screening the human galanin receptor agonist or antagonist, characterized in that, a comparison is conducted between the cases where (i) the human galanin receptor protein of the present invention or the partial peptide or the salt thereof is contacted with galanin and where (ii) the human galanin receptor protein of the present invention or the partial peptide or the salt thereof is contacted with galanin and a test compound; and (II) a method of screening the galanin receptor agonist or antagonist, characterized in that, a comparison is conducted between the cases where (i) cells containing the human galanin receptor protein of the present invention or cell membrane fraction thereof are contacted with galanin and where (ii) cells containing the human galanin receptor protein of the present invention or cell membrane fraction thereof are contacted with galanin and a test compound.

To be more specific, in the screening methods (I) and (II) of the present invention, the cell-stimulating activity and/or binding amount of galanin to said human galanin receptor protein or partial peptide or salt thereof or cells containing the human galanin receptor protein or cell membrane fraction thereof in (i) and (ii) are measured and compared.

In one more specific embodiment of the present invention,

① a method of screening a galanin receptor agonist and/or galanin receptor antagonist or a salt thereof, characterized in that, when a labeled galanin is contacted with a galanin receptor protein (e.g., human-derived galanin receptor protein, etc.) or a partial peptide thereof and when a labeled galanin and a test compound are contacted with a galanin receptor protein (e.g., human-derived galanin receptor protein, etc.) or a partial peptide thereof, the amounts of the labeled galanin bonded with said protein or partial peptide thereof or salt thereof are measured and compared;

② (a) (i) a method of screening a galanin receptor agonist and/or galanin receptor antagonist or a salt thereof, characterized in that, when a labeled galanin is contacted with galanin receptor protein (e.g., human or mouse galanin receptor protein, etc.)-containing cells (e.g., mouse MIN 6 cell (FERM BP-4954), etc.) or a membrane fraction of said cells and when a labeled galanin and a test compound are contacted with galanin receptor protein (e.g., human or mouse galanin receptor protein, etc.)-containing cells (e.g., mouse MIN 6 cell (FERM BP-4954), etc.) or a membrane fraction of said cells, the amounts of the labeled galanin binding with said protein or partial peptide thereof or a salt thereof are measured and compared;

(b) (ii) a method of screening a galanin receptor agonist and/or galanin receptor antagonist or a salt thereof, characterized in that, when a galanin receptor protein-activating compound (e.g. galanin) is contacted with galanin receptor protein (e.g., human or mouse galanin receptor protein, etc.)-containing cells (e.g., mouse MIN 6 cell (FERM BP-4954), etc.) or a membrane fraction of said cells and when the galanin receptor protein-activating compound and a test compound are contacted with galanin receptor protein (e.g., human or mouse galanin receptor protein, etc.)-containing cells (e.g., mouse MIN 6 cell (FERM BP-4954), etc.) or a membrane fraction of said cells, the resulting galanin receptor protein-mediated cell stimulating activities (e.g. activities of promoting or activities of inhibiting physiological responses including the opening of $K^+$ channel, closing of N type $Ca^+$ channel liberation of arachidonic acid, liberation of acetylcholine, endocellular $Ca^{2+}$ changes, endocellular CAMP production (or its depression), endocellular cGMP production, insulin secretion, production of inositol phosphate, cell membrane potential changes, phosphorylation of endocellular proteins, activation of c-fos, decrease of pH, cell migration activity, secretion of hormones, activation of G protein, cell promulgation, etc.) are measured and compared; and ③ a method of screening a galanin receptor agonist and/or galanin receptor antagonist or a salt thereof, characterized in that, when a labeled galanin is contacted with galanin receptor proteins (e.g., human or mouse galanin receptor proteins, etc.) expressed on the cell membrane by culturing a transformant containing a galanin receptor protein encoding DNA and when a labeled galanin and a test compound are contacted with galanin receptor proteins (e.g., human or mouse galanin receptor proteins, etc.) expressed on the cell membrane by culturing a transformant containing a galanin receptor protein encoding DNA, the amounts of the labeled galanin binding with said galanin receptor protein are measured and compared;

④ a method of screening a galanin receptor agonist and/or galanin receptor antagonist or a salt thereof, characterized in that, when a galanin receptor protein-activating compound (e.g. galanin) is contacted with galanin receptor proteins (e.g., human or mouse galanin receptor proteins, etc.) expressed on cell membranes by culturing transformants containing galanin receptor protein-encoding DNA and when a galanin receptor protein-activating compound and a test compound are contacted with the galanin receptor protein expressed on the cell membrane by culturing the transformant containing the galanin receptor protein-encoding DNA, the resulting galanin receptor protein-mediated cell stimulating activities (activities of promoting or activities of inhibiting physiological responses such as liberation of arachidonic acid, liberation of acetylcholine, endocellular $Ca^{2+}$ liberation, endocellular cAMP production, endocellular cGMP production, production of inositol phosphate, changes in cell membrane potential, phosphorylation of endocellular proteins, activation of c-fos, lowering of pH, insulin secretion, etc.) are measured and compared:

are provided.

In the above-mentioned screening methods ① or ② (a), a compound which binds with a galanin receptor protein (e.g., human galanin receptor protein, etc.) and inhibits the binding of galanin with the galanin receptor protein can be selected as a galanin receptor agonist or antagonist.

Further, in the above-mentioned screening method ② (b), a compound which exhibits a cell-stimulating activity (for example, activities of promoting or inhibiting the opening of $K^+$ channel, closing of N type $Ca^+$ channel, liberation of arachidonic acid, liberation of acetylcholine, variations in intracellular $Ca^{2+}$ concentration, inhibition of intracellular CAMP production, production of inositol phosphate, variations in cell membrane potential, phosphorylation of intracellular protein, activation of c-fos, decrease in pH, cell migration activity, secretion of hormones, activation of G protein, cell promulgation, etc.) via the galanin receptor (e.g., human galanin receptor, etc.) upon said galanin receptor binding can be selected as a galanin receptor agonist.

On the other hand, in the above-mentioned screening methods ① and ② (a), a compound having no stimulating activity to said cells among the test compounds which exhibit an activity of inhibiting the binding of galanin with the galanin protein receptor (e.g., human galanin receptor protein, etc.) can be selected as a galanin receptor antagonist.

Before the cells containing the galanin receptor protein (e.g., human galanin receptor protein, etc.) of the present invention were developed, there was no cell which highly expressed the galanin receptor protein (e.g., human galanin receptor protein, etc.) and, therefore, it has not been possible to conduct an effective screening of galanin receptor agonists or antagonists.

Specific explanations of the screening method will be given as hereunder.

First, with respect to the galanin receptor protein such as the mouse-derived galanin receptor protein used for the screening method of the present invention, any product may be used so far as it contains galanin receptor proteins or partial peptide thereof such as mouse-derived galanin receptor proteins or partial peptide thereof although the use of a membrane fraction derived from mammalian organs, tissues, cells, including mouse, is suitable. Galanin receptor proteins which are expressed in a large amount using a recombinant are suitable for the screening.

In the manufacture of the galanin receptor protein (for example, mouse-derived galanin receptor protein, etc.), the above-mentioned method can be used and it may be carried out by expressing the DNA coding for said protein in mammalian cells or in insect cells. With respect to the DNA fragment coding for the target region, complementary DNA may be used although it is not limited thereto. Thus, for example, gene fragments or synthetic DNA may be used as well.

In order to introduce the galanin receptor protein-encoding DNA fragment (for example, mouse-derived galanin receptor protein-encoding DNA fragment, etc.) into host animal cells and to express it efficiently, it is preferred that said DNA fragment is incorporated into the downstream of polyhedron promoter of nuclear polyhedrosis virus belonging to baculovirus, promoter derived from SV40, promoter of retrovirus, metallothionein promoter, human heat shock promoter, cytomegalovirus promoter, SRα promoter, etc. Examinations of the quantity and the quality of expressed receptors can be carried out by known methods per se or modified methods substantially analogous thereto. For example, they may be conducted by the method described in publications such as Nambi, P. et al.: The Journal of Biochemical Society, vol.267, pages 19555–19559 (1992).

Accordingly, in the screening method, the substance containing a galanin receptor protein or a partial peptide thereof (for example, mouse-derived galanin receptor protein or its partial peptide, etc.) may be a galanin receptor protein or its partial peptide (for example, mouse-derived galanin receptor protein or its partial peptide, etc.) which is purified by known methods per se or a cell containing said protein or a cell membrane fraction of the cell containing said protein, etc.

When the galanin receptor protein-containing cells are used in the screening method, said cells may be immobilized with glutaraldehyde, formalin, etc. The immobilization may be carried out by known methods per se or modified methods substantially analogous thereto.

For example, the mouse-derived galanin receptor protein-containing cells are host cells expressing the mouse-derived galanin receptor, naturally occurring cells containing the mouse-derived galanin receptor protein, etc. Examples of said host cells may include *Escherichia coli*, *Bacillus subtilis*, yeasts, insect cells, animal cells such as CHO cell and COS cell, etc. The host cell expressing the mouse-derived galanin receptor can be produced by the method according to the above-mentioned transformant production.

In conducting the above-mentioned methods ①, ② (a) and ③ for screening the galanin receptor agonist and/or galanin receptor antagonist, a suitable galanin receptor fraction and a labeled galanin are necessary. With respect to the galanin receptor fraction, it is preferred to use naturally occurring galanin receptors (natural type galanin receptors), recombinant type galanin receptor fractions with the activity equivalent to that of the natural type galanin receptor, cells expressing the recombinant type mouse-derived galanin receptor, naturally occurring cells containing the mouse-derived galanin receptor, etc. Here the term "activity equivalent to" means the same galanin binding activity, or the substantially equivalent galanin binding activity.

With respect to the labeled galanin, it is possible to use labeled galanin, labeled galanin analogized compounds, etc. For example, galanin labeled with [$^3$H], [$^{125}$I], [$^{14}$C], [$^{35}$S], etc. and other labeled substances may be utilized. Known galanin agonists and antagonists labeled with [$^3$H], [$^{125}$I], [$^{14}$C], etc. may be utilized. Preferred examples of the labeled galanin are galanin labeled with [$^{125}$I] (Dupont/NEN), etc.

Specifically, galanin receptor protein-containing cells or cell membrane fractions (for example, human or mouse galanin receptor protein-containing cells or cell membrane fractions of the present invention) or the galanin receptor proteins or partial peptides thereof are first suspended in a buffer which is suitable for the measuring method to prepare the receptor sample in conducting the screening for a galanin receptor agonist and/or galanin receptor antagonist. With respect to the buffer, any buffer such as Tris-HCl buffer or phosphate buffer of pH 4–10 (preferably, pH 6–8) which does not inhibit the binding of galanin with the receptor may be used.

In addition, a surface-active agent such as CHAPS, Tween 80™ (Kao-Atlas, Japan), digitonin, deoxycholate, etc. and/or various proteins such as bovine serum albumin (BSA), gelatin, etc. may be added to the buffer with an object of decreasing the nonspecific binding. Further, a protease inhibitor such as PMSF, leupeptin, bacitracin, aprotinin, E-64 (manufactured by Peptide Laboratory, Japan), pepstatin, etc. may be added with an object of inhibiting the decomposition of the receptor and galanin by protease. A labeled galanin in a certain amount (for example, about 10,000 cpm to 1,000,000 cpm in case of 2000Ci/mmol; 5,000 cpm to 500,000 cpm in other cases) is added to 0.01 ml to 10 ml of said receptor solution and, at the same time, $10^{-4}$ M to $10^{-10}$ M of a test compound coexists. In order to determine the nonspecific binding amount (NSB), a reaction tube to which a great excessive amount of unlabeled test compounds is added is prepared as well.

The reaction is carried out at 0–50° C. (preferably at 4–37° C.) for 20 minutes to 24 hours (preferably 30 minutes to three hours). After the reaction, it is filtered through a glass fiber filter, a filter paper, or the like, washed with a suitable amount of the same buffer and the radioactivity (for example, the amount of [$^{125}$I], etc.) retained in the glass fiber filter, etc. is measured by means of a liquid scintillation counter or a γ-counter. Although a manifold or a cell harvester may be used for the filtration, the use of cell harvester is recommended for improving the efficiency. Supposing that the count ($B_0$–NSB) obtained by subtracting the nonspecific binding amount (NSB) from the total binding amount ($B_0$) wherein an antagonizing substance is not present is set at 100%, the test compound in which the specific binding amount (B–NSB) obtained by subtracting the nonspecific binding amount (NSB) from the total binding amount (B) is, for example, less than 50% may be selected as a inhibitory candidate substance, i.e., agonist and/or antagonist candidate compound.

In an embodiment of the screening using human galanin receptor proteins, the operation is carried out in accordance with the following procedures:

(i) A reaction buffer (pH: 7.4) comprising 20 mM of Tris-HCl, 1 mM of EDTA, 0.1% of BSA, 0.05% of CHAPS, 0.5 mM of PMSF, 40 μg/ml of leupeptin, 20 μg/ml of E-64 and 10 μg/ml of pepstatin is prepared.

(ii) A test compound solution (2 μl) in which the test compound is suspended in the reaction buffer is placed in a reaction tube on an ice bath. The final concentration of the test compound is adjusted to 100 μM.

(iii) The cell membrane fraction containing human galanin receptor protein freeze-dried at −80° C. is returned to a room temperature and then vortex is gently generated and diluted to a suitable concentration to prepare a cell membrane fraction solution (for example, 0.5 mg protein/ml (bovine hippocampal membrane fraction, CHO cell membrane fraction) etc.). This cell membrane fraction solution is passed through a cell strainer and each 200 µl of it is placed in each reaction tube using a separator.

(iv) Each 2 µl of [$^{125}$I] galanin diluted in a reaction buffer is placed in a reaction tube on an ice bath.

(v) The reaction is carried out at 25° C. for 60 or 75 minutes.

(vi) A B/F separation is conducted using a manifold. The filter (GF/F, Whatman) which is used therefor is previously dipped in a PEI solution (20 mM Tris-HCl and 0.3% polyethyleneimide; pH: 7.4) for more than one hour.

(vii) The filter is counted using a gamma-counter. The compound which inhibits the specific binding to an extent of 40–50% or more and of 50% or more is evaluated as ± and +, respectively.

In conducting the above-mentioned methods ② (b) and ④ for screening the galanin receptor agonist and/or galanin receptor antagonist, the galanin receptor protein (e.g., mouse-derived galanin receptor protein)-mediated cell stimulating activity (e.g., activities of promoting or activities of inhibiting physiological responses such as liberation of arachidonic acid, liberation of acetylcholine, endocellular $Ca^{2+}$ liberation, endocellular cAMP production, endocellular cGMP production, production of inositol phosphate, changes in the cell membrane potential, phosphorylation of endocellular proteins, activation of c-fos, lowering of pH, secretion of insulin, etc.) may be measured by known methods or by the use of commercially available measuring kits.

In conducting a screening method of the above-mentioned ② (b), it is possible to measure the cell stimulating activity via the galanin receptor protein (e.g., human galanin receptor protein, etc.) (for example, activities of promoting or inhibiting the opening of $K^+$ channel, closing of N type $Ca^+$ channel, liberation of arachidonic acid, liberation of acetylcholine, variations in intracellular $Ca^{2+}$ concentration, inhibition of intracellular CAMP production, production of inositol phosphate, variations in cell membrane potential, phosphorylation of intracellular protein, activation of c-fos, decrease in pH, cell migration activity, secretion of hormones, activation of G protein, cell promulgation, etc.) by known method or by commercially-available measuring kits. To be more specific, galanin receptor protein (e.g., human or mouse-derived galanin receptor protein, etc.)-containing cells are at first cultured in a multiwell plate or the like.

In conducting the screening, it is substituted with a suitable buffer which does not show toxicity to fresh media or cells in advance, incubated for a certain period after adding a test compound, etc. thereto. The resultant cells are extracted or the supernatant liquid is recovered and the resulting product is determined, preferably quantitatively, by each of the methods. When it is difficult to identify the production of the index substance (e.g. arachidonic acid, etc.) which is to be an index for the cell stimulating activity due to the presence of decomposing enzymes contained in the cell, an assay may be carried out by adding an inhibitor against said decomposing enzyme. With respect to the activities such as an inhibitory action against cAMP production, it may be detected as an inhibitory action against the CAMP production in the cells whose fundamental production has been increased by forskolin or the like.

In conducting a screening by measuring the cell stimulating activity, cells in which a suitable galanin receptor protein (e.g., mouse-derived galanin receptor protein) is expressed are necessary. Preferred galanin receptor protein (e.g., mouse-derived galanin receptor protein)-expressing cells are naturally occurring mouse-derived galanin receptor protein (natural type mouse-derived galanin receptor protein)-containing cell lines or strains (e.g., mouse MIN6 (FERM BP-4954), etc.), the above-mentioned recombinant type mouse-derived galanin receptor protein-expressing cell lines or strains, etc. Among them, the natural type mouse-derived galanin receptor protein-containing cell line, mouse pancreas-derived MIN6 cell, is capable of secreting insulin from intracellular regions when galanin binds with galanin receptors on the cell membrane of said cell. In case where the insulin secretion is used as an index for the cell stimulating activity, mouse pancreas-derived MIN6 cell is particularly preferred.

Examples of the test compound includes peptides, proteins, non-peptidic compounds, synthesized compounds, fermented products, cell extracts, plant extracts, animal tissue extracts, serum, blood, body fluid, etc. Those compounds may be novel or known.

A kit for screening the galanin receptor agonist and/or galanin receptor antagonist comprises a galanin receptor protein or a salt thereof according to the present invention (e.g., human or mouse-derived galanin receptor protein or its salt) or a partial peptide thereof according to the present invention (e.g., human or mouse-derived galanin receptor partial peptide or its salt), a galanin receptor protein (e.g., human or mouse-derived galanin receptor protein)-containing cell or its cell membrane fraction according to the present invention, etc.

Examples of the screening kit include as follows:

1. Reagent for Determining Ligand

① Buffer for Measurement and Buffer for Washing.

The product wherein 0.05% of bovine serum albumin (manufactured by Sigma) is added to Hanks' Balanced Salt Solution (manufactured by Gibco).

This may be sterilized by filtration through a membrane filter with a 0.45 µm pore size, and stored at 4° C. or may be prepared upon use.

② Sample of Mouse-Derived Galanin Receptor Protein.

CHO cells in which a mouse-derived galanin receptor protein is expressed are subcultured at the rate of 5×10$^5$ cells/well in a 12-well plate and cultured at 37° C. with a 5% $CO_2$ and 95% air atmosphere for two days to prepare the sample.

③ Labeled Galanin.

The galanin which is labeled with commercially available [$^3$H], [$^{125}$I], [$^{14}$C], [$^{35}$S]etc.

The product in a state of an aqueous solution is stored at 4° C. or at −20° C. and, upon use, diluted to 5 µM with a buffer for the measurement.

④ Standard Galanin Solution.

Galanin is dissolved in PBS containing 0.1% of bovine serum albumin (manufactured by Sigma) to make 100 µM and stored at −20° C.

2. Method of the Measurement

① CHO cells are cultured in a 12-well tissue culture plate to express mouse-derived galanin receptor proteins. The receptor protein-expressing CHO cells are washed with 1 ml of buffer for the measurement twice. Then 490 µl of buffer for the measurement is added to each well.

② Five µl of a test compound solution of 10$^{-3}$ to 10$^{-10}$ M is added, then 5 µl of a labeled galanin is added and is made to react at room temperature for one hour. For knowing the non-specific binding amount, 5 μl of the galanin of $10^{-4}$ M is added instead of the test compound.

③ The reaction solution is removed from the well, which is washed with 1 ml of buffer for the measurement three times. The labeled ligand binding with the cells is dissolved in 0.2N NaOH-1% SDS and mixed with 4 ml of a liquid scintillator A (manufactured by Wako Pure Chemical, Japan).

④ Radioactivity is measured using an automatic γ-counter or a liquid scintillation counter (manufactured by Beckmann) and PMB (percent of maximum binding) is calculated by the following expression (1):

$$PMB=[(B-NSB)/(B_0-NSB)]\times 100 \quad (1)$$

| | |
|---|---|
| PMB: | Percent of maximum binding |
| B: | Value when a sample is added |
| NSB: | Nonspecific binding |
| $B_0$: | Maximum binding |

Another example of the screening kit is as follows:
[Reagents for the Screening]
① Buffer for Measurement and for Washing.

Hanks buffer to which 0.01% of bovine serum albumin and 0.05% of CHPS are added is used. This is filtered through a filter with a pore size of 0.22 μm, sterilized and stored at 4° C. or may be prepared upon use.

② Human Galanin Receptor Protein Sample.

Cells containing the human galanin receptor protein are subcultured in a 12-well plate at $5\times 10^5$/well and cultured at 37° C. with 5% $CO_2$ and 95% air until cells become confluent.

③ Labeled galanin.

Commercially-available galanin which is labeled with [$^3$H], [$^{125}$I], [$^{14}$C], etc. is used. That which is in a state of solution is stored at 4° C. or −20° C. and, upon use, it is diluted to 1 μl with a buffer for the measurement.

④ Standard Galanin Solution.

Galanin is diluted with sterilized water to make $10^{-4}$ M and stored at −20° C.
[Method of Measurement]
① Cells containing human galanin receptor protein cultured in a 12-well culturing plate are washed, about twice, with 1 ml of a buffer for measurement.

② After the buffer for measurement is sucked out, 5 μl of a test compound solution ($10^{-3}$ to $10^{-10}$ M) cooled at 4° C. is added, then 0.5 ml of a buffer for measurement, containing 100 pM of a labeled galanin, is added and the mixture is made to react at 37° C. for one hour with 5% $CO_2$ and 95% air. In order to know the nonspecific binding amount, 1 μM of galanin is added together with the test compound.

③ The reaction solution is removed and washed, three times, with 1 ml of buffer for washing which is kept at 37° C. The labeled galanin bonded to the cells is removed with 0.5 ml of 0.2N NaOH and the radioactivity is measured by a γ-counter to calculate the PMB (percent of maximum binding) from the above formula (1).

In the above-mentioned screening methods and screening kit, it is also possible to use recombinant human galanin receptor protein manufactured from DNA such as known human galanin receptor protein DNA or the like or partial peptide thereof or cells containing said recombinant human galanin receptor protein or a cell membrane fraction thereof instead of the human galanin receptor protein of the present invention or the partial peptide thereof or cells containing the human galanin receptor protein or a cell membrane fraction thereof.

The compound or its salt obtained by the screening method or screening kit of the present invention is a compound which inhibits the binding of galanin with a galanin receptor protein and, more particularly, it is a compound having a cell stimulating activity mediated via a galanin receptor or a salt thereof (so-called "galanin receptor agonist") or a compound having no said stimulating activity (so-called "galanin receptor antagonist"). Examples of said compound are peptides, proteins, non-peptidic compounds, synthesized compounds, fermented products, etc. and the compound may be novel or known. The galanin receptor agonist or antagonist obtained by the screening method or the screening kit of the present invention is a compound or salt thereof selected from the test sample including the compounds (for example, peptides, proteins, nonpeptidic compounds, synthesized compounds, fermented products, cell extracts, plant extracts, animal tissue extracts, cell or tissue cultures, biological fluids, etc.; said test compounds may be either novel or known) using the screening method or the screening kit of the present invention and is a compound which inhibits the binding of galanin with the recombinant human galanin receptor protein of the present invention. Among those compounds, galanin receptor agonist is a compound which exhibits a cell-stimulating activity via a human galanin receptor while galanin receptor antagonist is a compound which does not exhibit said cell-stimulating activity.

In addition, the compounds in which the structure of said galanin receptor agonist or antagonist obtained by the screening method or the screening kit of the present invention is chemically modified or substituted or the compounds in which a design is conducted based upon said structure are also included in the galanin receptor agonist or antagonist obtained by the screening method or the screening kit of the present invention.

With respect to the salt of said galanin receptor agonist or antagonist, physiologically-acceptable acid addition salts thereof are particularly preferred. Examples of such salts are those with inorganic acids (for example, hydrochloric acid, phosphoric acid, hydrobromic acid and sulfuric acid) or with organic acids (for example, acetic acid, formic acid, propionic acid, fumaric acid, maleic acid, succinic acid, tartaric acid, citric acid, maleic acid, oxalic acid, benzoic acid, methanesulfonic acid and benzenesulfonic acid).

The galanin receptor agonist exhibits all or part of the physiological activities of galanin or its equivalent and, therefore, it is useful as an active ingredient for a pharmaceutical composition with safety and low toxicity depending upon said physiological activities. On the other hand, the galanin receptor antagonist may inhibit all or part of the physiological activities of galanin or its equivalent and, therefore, it is useful as an active ingredient for a pharmaceutical composition with safety and low toxicity inhibiting said physiological activities.

More specifically, galanin receptor agonists are useful as an inhibitor for liberation of acetylcholine, an inhibitor for insulin secretion, a stimulant for growth hormone secretion, an inhibitor for learning behavior or an inhibitor for satiety, etc. and, moreover, it is useful as a preventive and therapeutic agent for schizophrenic disease, gastric ulcer, as a sedative, etc. On the other hand, galanin receptor antagonists are useful as an accelerator for liberation of acetylcholine, an accelerator for insulin secretion, an inhibitor for growth hormone secretion, an accelerator for learning behavior and an accelerator for satiety, etc. and, moreover, it is useful as a preventive and therapeutic agent for diabetes, Alzheimer's disease, dementia, etc.

When the galanin receptor agonist and/or galanin receptor antagonist or the salt thereof obtained by the screening method or by the screening kit is used as the above-mentioned pharmaceutical composition, a conventional means may be applied therefor. The compound or the salt thereof may be orally, parenterally, by inhalation spray, rectally, or topically administered as pharmaceutical compositions or formulations (e.g. powders, granules, tablets, pills, capsules, injections, syrups, emulsions, elixirs, suspensions, solutions, etc.). For example, it may be used by an oral route as tablets (sugar-coated if necessary), capsules, elixirs, microcapsules, etc. or by a parenteral route as injections such as an aseptic solution or a suspension in water or in other pharmaceutically acceptable liquid. The pharmaceutical compositions or formulations may comprise at least one such compound alone or in admixture with pharmaceutically acceptable carriers, adjuvants, vehicles, excipients and/or diluents. The pharmaceutical compositions can be formulated in accordance with conventional methods. For example, said compound or the salt thereof is mixed in a unit dose form which is required for preparing a generally approved pharmaceutical preparations together with a physiologically acceptable carriers, flavoring and/or perfuming agents (fragrances), fillers, vehicles, antiseptics, stabilizers, binders, etc. whereupon the preparation can be manufactured. An amount of the effective component in those preparations is to be in such an extent that the suitable dose within an indicated range is achieved.

Examples of the additives which can be admixed in the tablets, capsules, etc. are binders such as gelatin, corn starch, tragacanth and gum arabicum; fillers such as crystalline cellulose; swelling agents such as corn starch, gelatin and alginic acid; lubricants such as magnesium stearate; sweetening agents such as sucrose, lactose and saccharine; preservatives such as parabens and sorbic acid; antioxidants such as ascorbic acid, α-tocopherol and cysteine; fragrances such as peppermint, akamono oil and cherry; disintegrants; buffering agents; etc. Other additives may include mannitol, maltitol, dextran, agar, chitin, chitosan, pectin, collagen, casein, albumin, synthetic or semi-synthetic polymers, glyceride, lactide, etc. When the unit form of the preparation is a capsule, a liquid carrier such as fat/oil may be further added besides the above-mentioned types of materials. The aseptic composition for injection may be formulated by a conventional technique or practice for the preparations such as that the active substance in a vehicle such as water for injection is dissolved or suspended in a naturally occurring plant oil such as sesame oil and palm oil.

Examples of an aqueous liquid for the injection are a physiological saline solution and isotonic solutions containing glucose and other auxiliary agents (e.g. D-sorbitol, D-mannitol, sodium chloride, etc.) wherein a suitable auxiliary solubilizers such as alcohol (e.g. ethanol, etc.), poly-alcohol (e.g. propylene glycol, polyethylene glycol, etc.), nonionic surface-active agent (e.g. Polysorbate 80™, HCO-50, etc.), etc. may be jointly used. In the case of the oily liquid, sesame oil, soybean oil, etc. may be exemplified wherein benzyl benzoate, benzyl alcohol, etc. may be jointly used as auxiliary solubilizers.

In addition, buffers (e.g. phosphate buffer, sodium acetate buffer, etc.), analgesic agents (e.g. benzalkonium chloride, procaine hydrochloride, etc.), stabilizers (e.g. human serum albumin, polyethylene glycol, etc.), stabilizers (e.g. benzyl alcohol, phenol, etc.), antioxidants, etc. may be compounded therewith too. The prepared injection solution is filled in suitable ampoules. The formulation prepared as such is safe and less toxic and, therefore, it can be administered to warm-blooded mammals such as rats, rabbits, sheep, swines, cattle, cats, dogs, monkeys, human being, etc.

Dose levels of said galanin receptor agonist and/or galanin receptor antagonist or the salt thereof may vary depending upon the symptom. Specific dose levels for any particular patient will be employed depending upon a variety of factors including the activity of specific compounds employed, the age, body weight, general health, sex, diet, time of administration, route of administration, rate of excretion, drug combination, and the severity of the particular disease undergoing therapy. In the case of oral administration, it is usually about 0.1–100 mg, preferably about 1.0–50 mg or, more preferably, about 1.0–20 mg per day for adults (as 60 kg). When it is administered parenterally, its dose at a time may vary depending upon the object to be administered, organs to be administered, symptoms, administering methods, etc. The term "parenteral" as used herein includes subcutaneous injections, intravenous, intramuscular, intraperitoneal injections, or infusion techniques. In the case of injections, it is usually convenient to give by an intravenous route in an amount of about 0.01–30 mg, preferably about 0.1–20 mg or, more preferably, about 0.1–10 mg per day to adults (as 60 kg). In the case of other animals, the dose calculated for 60 kg may be administered as well.

(3) Preventive and Therapeutic Agent for of Galanin Receptor Protein Deficiency Diseases The galanin receptor protein (e.g., human galanin receptor protein)-encoding DNA can be used a preventive and/or therapeutic agent for treating said galanin receptor protein deficiency diseases.

For example, when there is a patient for whom the physiological action of galanin cannot be expected because of a decrease in the galanin receptor protein (e.g., human galanin receptor protein) in vivo, the amount of the galanin receptor protein in the cells of said patient can be increased whereby the action of galanin can be fully achieved by:

(a) administering the galanin receptor protein (e.g., human galanin receptor protein)-encoding DNA to the patient to express it; or (b) inserting the galanin receptor protein (e.g., human galanin receptor protein)-encoding DNA into cells or the like to express it, followed by transplanting said cells or the like to said patient. Accordingly, the galanin receptor protein (e.g., human galanin receptor protein)-encoding DNA can be used as a safe and less toxic preventive and therapeutic agent for the galanin receptor protein (e.g., human galanin receptor protein) deficiency diseases (e.g., diabetes, Alzheimer's disease, dementia, etc.). It may be used in treating or remedying defects by promoting the acetylcholine liberation, inhibiting the growth hormone secretion, promoting the insulin secretion, promoting the learning behavior, promoting satiety, etc.

When the DNA of the present invention is used as the above-mentioned agent, said DNA may be used alone or after inserting it into a suitable vector such as retrovirus vector, adenovirus vector, adenovirus-associated virus vector, etc. followed by subjecting the product vector to a conventional means. Thus, it may be administered orally parenterally, by inhalation spray, rectally, or topically as pharmaceutical compositions or formulations. Oral formulations include tablets (sugar-coated if necessary), capsules, elixirs, microcapsules, etc. Parenteral formulations include injections such as an aseptic solution or a suspension in water or in other pharmaceutically acceptable liquid. For example, the DNA of the present invention is admixed in a unit dose form which is required for preparing generally approved pharmaceutical preparations together with a physiologically acceptable carriers, flavoring agents, adjuvants, excipients, diluents, fillers, vehicles, antiseptics, stabilizers, binders, etc. whereupon the preparation can be manufactured. The amount of the effective component in those preparations is to be in such an extent that the suitable dose within an indicated range is achieved.

Examples of the additives which can be admixed in the tablets, capsules, etc. are binders such as gelatin, corn starch, tragacanth and gum arabicum; fillers such as crystalline cellulose; swelling agents such as corn starch, gelatin and alginic acid; lubricating agents such as magnesium stearate; sweetening agents such as sucrose, lactose and saccharine; and flavoring agents such as pepper mint, akamono oil and cherry. When the unit dose form of the preparation is a capsule, a liquid carrier such as fat/oil may be further added in addition of the above-mentioned types of materials. The aseptic composition for injection may be formulated by conventional practices for the preparations such as that the active substance in a vehicle such as water for injection is dissolved or suspended in naturally occurring plant oil such as sesame oil and palm oil.

Examples of an aqueous liquid for injection are a physiological saline solution and isotonic solutions containing glucose and other auxiliary agents (e.g. D-sorbitol, D-mannitol, sodium chloride, etc.) wherein a suitable auxiliary solubilizers such as alcohol (e.g. ethanol, etc.), polyalcohol (e.g. propylene glycol polyethylene glycol, etc.), nonionic surface-active agent (e.g. Polysorbate 80™, HCO-50, etc.), etc. may be jointly used. Examples of an oily liquid include sesame oil, soybean oil, etc. wherein benzyl benzoate, benzyl alcohol, etc. may be jointly used as auxiliary solubilizers. In addition, buffers (e.g. phosphate buffer, sodium acetate buffer, etc.), analgesic agents (e.g. benzalkonium chloride, procaine hydrochloride, etc.), stabilizers (e.g. human serum albumin, polyethylene glycol, etc.), stabilizers (e.g. benzyl alcohol phenol, etc.), antioxidants, etc. may be admixed therewith too. The prepared injection solution is filled in suitable ampoules. The preparation prepared as such is safe and less toxic and, therefore, it can be administered to warm-blooded animals (e.g., rat, rabbit, sheep, swine, cattle, cat, dog, monkey, human beings, etc.).

Specific dose levels of said DNA may vary depending upon a variety of factors including the activity of drugs employed, the age, body weight, general health, sex, diet, time of administration, route of administration, drug combination, and the severity of the symptom. In the case of oral administration, it is usually about 0.1–100 mg, preferably about 1.0–50 mg or, more preferably, about 1.0–20 mg per day for adults (as 60 kg). When it is administered parenterally, its dose at a time may vary depending upon the object (patient) to be administered, organs to be administered, symptoms, administering methods, etc. but, in the case of injections, it is usually convenient to give by an intravenous route in an amount of about 0.01–30 mg, preferably about 0.1–20 mg or, more preferably, about 0.1–10 mg per day to adults (as 60 kg). For other animals, the dose calculated from the above based upon the body weight may be administered.

Furthermore, the method of inserting the DNA of the present invention into cells to express said galanin receptor protein (e.g., human galanin receptor protein, etc.) followed by transplanting said cells to the patient may be carried out by a method which is known per se or is similar thereto.

(4) Manufacture of Antibody or Antiserum against the Galanin Receptor Protein of the Present Invention, Its Partial Peptide or Its Salt Antibodies (e.g. polyclonal antibody and monoclonal antibody) and antisera against the galanin receptor protein or salt thereof of the present invention or against the peptide fragment of the galanin receptor protein or salt thereof of the present invention may be manufactured by antibody or antiserum-manufacturing methods per se known to those of skill in the art or methods similar thereto, using the galanin receptor protein or its salt of the present invention or the partial peptide (fragment) of the galanin receptor protein or its salt of the present invention. For example, monoclonal antibodies can be manufactured by the method as given herein below.

[Preparation of Monoclonal Antibody]

(a) Preparation of Monoclonal Antibody-Producing Cells.

The galanin receptor protein of the present invention or its salt or the partial peptide of the galanin receptor protein of the present invention or its salt is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every two to six weeks and two to ten times in total. Examples of the applicable warm-blooded animals are monkeys, rabbits, dogs, guinea pigs, mice, rats, sheep, goats chickens and hamsters and the use of mice, rats and hamsters is preferred.

In the preparation of the cells which produce monoclonal antibodies, an animal wherein the antibody titer is noted is selected from warm-blooded animals (e.g. mice) immunized with antigens, then spleen or lymph node is collected after two to five days from the final immunization and antibody-producing cells contained therein are fused with myeloma cells to give monoclonal antibody-producing hybridomas. Measurement of the antibody titer in antisera may, for example, be carried out by reacting a labeled galanin receptor protein (which will be mentioned later) with the antiserum followed by measuring the binding activity of the labeling agent with the antibody. The operation for fusing may be carried out, for example, by a method of Koehler and Milstein (Nature, 256, 495, 1975). Examples of the fusion accelerator are polyethylene glycol (PEG), Sendai virus, etc. and the use of PEG is preferred.

Examples of the myeloma cells are NS-1, P3U1, SP2/0, AP-1, etc. and the use of P3U1 is preferred. The preferred fusion ratio of the numbers of antibody-producing cells used (spleen cells) to the numbers of myeloma cells is within a range of about 1:1 to 20:1. When PEG (preferably, PEG 1000 to PEG 6000) is added in a concentration of about 10–80% followed by incubating at 20–40° C. (preferably, at 30–37° C.) for one to ten minutes, an efficient cell fusion can be carried out.

Various methods may be applied for screening a hybridoma which produces anti-galanin receptor antibody. For example, a supernatant liquid of hybridoma culture is added to a solid phase (e.g. microplate) to which the galanin receptor protein antigen is adsorbed either directly or with a carrier, then anti-immunoglobulin antibody (anti-mouse immunoglobulin antibody is used when the cells used for the cell fusion are those of mouse) which is labeled with a radioactive substance, an enzyme or the like, or protein A is added thereto and then anti-galanin receptor monoclonal antibodies bound on the solid phase are detected; or a supernatant liquid of the hybridoma culture is added to the solid phase to which anti-immunoglobulin or protein A is adsorbed, then the galanin receptor labeled with a radioactive substance or an enzyme is added and anti-galanin receptor monoclonal antibodies bonded with the solid phase is detected.

Selection and cloning of the anti-galanin receptor monoclonal antibody-producing hybridoma may be carried out by methods per se known to those of skill in the art or methods similar thereto. Usually, it is carried out in a medium for animal cells, containing HAT (hypoxanthine, aminopterin and thymidine). With respect to a medium for the selection, for the cloning and for the growth, any medium may be used so far as hybridoma is able to grow therein. Examples of the medium are an RPMI 1640 medium (Dainippon Pharmaceutical Co., Ltd., Japan) containing 1–20% (preferably 10–20%) of fetal calf serum (FCS), a GIT medium (Wako Pure Chemical, Japan) containing 1–20% of fetal calf serum and a serum-free medium for hybridoma culturing (SFM-101; Nissui Seiyaku, Japan). The culturing temperature is usually 20–40° C. and, preferably, about 37° C. The culturing time is usually from five days to three weeks and, preferably, one to two weeks. The culturing is usually carried out in 5% carbon dioxide gas. The antibody titer of the supernatant liquid of the hybridoma culture may be measured by the same manner as in the above-mentioned measurement of the antibody titer of the anti-galanin receptor in the antiserum.

The cloning can be usually carried out by methods known per se such as techniques in semi-solid agar and limiting dilution. The cloned hybridoma is preferably cultured in modern serum-free culture media to obtain optimal amounts of antibody in supernatants. The target monoclonal antibody is also preferably obtained from ascitic fluid derived from a mouse, etc. injected intraperitoneally with live hybridoma cells.

(b) Purification of the Monoclonal Antibody.

Like in the separation/purification of conventional polyclonal antibodies, the separation/purification of the anti-galanin receptor monoclonal antibody may be carried out by methods for separating/purifying immunoglobulin (such as salting-out, precipitation with an alcohol, isoelectric precipitation, electrophoresis, adsorption/deadsorption using ion exchangers such as DEAE, ultracentrifugation, gel filtration, specific purifying methods in which only an antibody is collected by treatment with an active adsorbent (such as an antigen-binding solid phase, protein A or protein G) and the bond is dissociated whereupon the antibody is obtained.

The galanin receptor antibody of the present invention which is manufactured by the aforementioned method (a) or (b) is capable of specifically recognizing galanin receptors and, accordingly, it can be used for a quantitative determination of the galanin receptor in test liquid samples and particularly for a quantitative determination by sandwich immunoassays.

Thus, the present invention provides, for example, the following methods:

(i) a quantitative determination of a galanin receptor in a test liquid sample, which comprises
   (a) competitively reacting the test liquid sample and a labeled galanin receptor with an antibody which reacts with the galanin receptor of the present invention, and
   (b) measuring the ratio of the labeled galanin receptor binding with said antibody; and
(ii) a quantitative determination of a galanin receptor in a test liquid sample, which comprises
   (a) reacting the test liquid sample with an antibody immobilized on an insoluble carrier and a labeled antibody simultaneously or continuously, and
   (b) measuring the activity of the labeling agent on the insoluble carrier wherein one antibody is capable of recognizing the N-terminal region of the galanin receptor while another antibody is capable of recognizing the C-terminal region of the galanin receptor.

When the monoclonal antibody of the present invention recognizing a galanin receptor (hereinafter, may be referred to as "anti-galanin receptor antibody") is used, galanin receptors can be measured and, moreover, can be detected by means of a tissue staining, etc. as well. For such an object, antibody molecules per se may be used or $F(ab')_2$, Fab' or Fab fractions of the antibody molecule may be used too. There is no particular limitation for the measuring method using the antibody of the present invention and any measuring method may be used so far as it relates to a method in which the amount of antibody, antigen or antibody-antigen complex, depending on or corresponding to the amount of antigen (e.g. the amount of galanin receptor, etc.) in the liquid sample to be measured, is detected by a chemical or a physical means and then calculated using a standard curve prepared by a standard solution containing the known amount of antigen. For example, nephrometry, competitive method, immunometric method and sandwich method are suitably used and, in terms of sensitivity and specificity, the sandwich method which will be described herein later is particularly preferred.

Examples of the labeling agent used in the measuring method using the labeling substance are radioisotopes, enzymes, fluorescent substances, luminescent substances, colloids, magnetic substances, etc. Examples of the radioisotope are $[^{125}I]$, $[^{131}I]$, $[^{3}H]$ and $[^{14}C]$; preferred examples of the enzyme are those which are stable and with big specific activity, such as β-galactosidase, β-glucosidase, alkali phosphatase, peroxidase and malate dehydrogenase; examples of the fluorescent substance are fluorescamine, fluorescein isothiocyanate, etc.; and examples of the luminescent substance are luminol, luminol derivatives, luciferin, lucigenin, etc. Further, a biotin-avidin system may also be used for binding an antibody or antigen with a labeling agent.

In an insolubilization (immobilization) of antigens or antibodies, a physical adsorption may be used or a chemical binding which is usually used for insolubilization or immobilization of proteins or enzymes may be used as well. Examples of the carrier are insoluble polysaccharides such as agarose, dextran and cellulose; synthetic resins such as polystyrene, polyacrylamide and silicone; glass; etc.

In a sandwich (or two-site) method, the test liquid is made to react with an insolubilized anti-galanin receptor antibody (the first reaction), then it is made to react with a labeled anti-galanin receptor antibody (the second reaction) and the activity of the labeling agent on the insoluble carrier is measured whereupon the amount of the galanin receptor in the test liquid can be determined. The first reaction and the second reaction may be conducted reversely or simultaneously or they may be conducted with an interval. The type of the labeling agent and the method of insolubilization (immobilization) may be the same as those mentioned already herein. In the immunoassay by means of a sandwich method, it is not always necessary that the antibody used for the labeled antibody and the antibody for the solid phase is one type or one species but, with an object of improving the measuring sensitivity, etc., a mixture of two or more antibodies may be used too.

In the method of measuring galanin receptors by the sandwich method of the present invention, the preferred anti-galanin receptor antibodies used for the first and the second reactions are antibodies wherein their sites binding to the galanin receptors are different each other. Thus, the antibodies used in the first and the second reactions are those wherein, when the antibody used in the second reaction recognizes the C-terminal region of the galanin receptor, then the antibody recognizing the site other than C-terminal regions, e.g. recognizing the N-terminal region, is preferably used in the first reaction.

The anti-galanin receptor antibody of the present invention may be used in a measuring system other than the sandwich method such as a competitive method, an immunometric method and a nephrometry. In a competitive method, an antigen in the test solution and a labeled antigen are made to react with an antibody in a competitive manner, then an unreacted labeled antigen (F) and a labeled antigen binding with an antibody (B) are separated (i.e. B/F separation) and the labeled amount of any of B and F is measured whereupon the amount of the antigen in the test solution is determined. With respect to a method for such a reaction, there are a liquid phase method in which a soluble antibody is used as the antibody and the B/F separation is conducted by polyethylene glycol, a second antibody to the above-mentioned antibody, etc.; and a solid phase method in which an immobilized antibody is used as the first antibody or a soluble antibody is used as the first antibody while an immobilized antibody is used as the second antibody.

In an immunometric method, an antigen in the test solution and an immobilized antigen are subjected to a competitive reaction with a certain amount of a labeled antibody followed by separating into solid and liquid phases; or the antigen in the test solution and an excess amount of labeled antibody are made to react, then a immobilized antigen is added to bind an unreacted labeled antibody with the solid phase and separated into solid and liquid phases. After that, the labeled amount of any of the phases is measured to determine the antigen amount in the test solution.

In a nephrometry, the amount of insoluble sediment which is produced as a result of the antigen-antibody reaction in a gel or in a solution is measured. Even when the antigen amount in the test solution is small and only a small amount of the sediment is obtained, a laser nephrometry wherein scattering of laser is utilized can be suitably used.

In applying each of those immunological measuring methods (immunoassays) to the measuring method of the present invention, it is not necessary to set up any special condition, operation, etc. therefor. A measuring system (assay system) for galanin receptor may be constructed taking the technical consideration of the persons skilled in the art into consideration in the conventional conditions and operations for each of the methods. With details of those conventional technical means, a variety of reviews, reference books, etc. may be referred to. They are, for example, Hiroshi Irie (ed): "Radioimmunoassay" (Kodansha, Japan, 1974); Hiroshi Irie (ed): "Radioimmunoassay; Second Series" (Kodansha, Japan, 1979); Eiji Ishikwa et al. (ed): "Enzyme Immunoassay" (Igaku Shoin, Japan, 1978); Eiji Ishikawa et al. (ed): "Enzyme Immunoassay" (Second Edition) (Igaku Shoin, Japan, 1982); Eiji Ishikawa et al. (ed): "Enzyme Immunoassay" (Third Edition) (Igaku Shoin, Japan, 1987); "Methods in Enzymology" Vol. 70 (Immunochemical Techniques (Part A)); ibid. Vol. 73 (Immunochemical Techniques (Part B)); ibid. Vol. 74 (Immunochemical Techniques (Part C)); ibid. Vol. 84 (Immunochemical Techniques (Part D: Selected Immunoassays)); ibid. Vol. 92 (Immunochemical Techniques (Part E: Monoclonal Antibodies and General Immunoassay Methods)); ibid. Vol. 121 (Immunochemical Techniques (Part I: Hybridoma Technology and Monoclonal Antibodies)) (Academic Press); etc.

As such, the amount of galanin receptor proteins can now be determined with a high precision using the anti-galanin receptor antibody of the present invention.

(5) Preparation of Animals Having the Galanin Receptor Protein-Encoding DNA of the Present Invention.

It is possible to prepare transgenic animals expressing galanin receptors using galanin receptor protein-encoding DNA. Examples of the animals are warm-blooded mammals such as rats, mice, rabbit, sheep, swines, cattle, cats, dogs and monkeys.

In transferring the galanin receptor protein-encoding DNA to the aimed animal, it is generally advantageous that said DAN is used by ligating with a site at the downstream of a promoter which is capable of expressing in animal cells. For example, when galanin receptor protein DNA is to be transferred to a rabbit, a gene construct ligated with a site at the downstream of various promoters which are capable of expressing the galanin receptor protein DNA derived from an animal compatible to the animal in animal host cells is subjected to a microinjection to the fertilized ovum (oosperm) of the aimed animal (e.g. fertilized ovum (embryo) of rabbit) whereupon the transgenic animal which produces the galanin receptor protein in a high amount can be prepared.

Examples of the promoters used are promoters derived from virus and ubiquitous expression promoters such as metallothionein promoters may be used but, preferably, enolase gene promoters and NGF gene promoters capable of specifically expressing in brain are used.

Transfer of the galanin receptor protein DNA at a fertilized ovum cell stage is secured in order that the DNA can be present in all of embryonal cells and body somatic cells of an aimed animal. The fact that the galanin receptor protein is present in the fertilized ovum cells of the produced transgenic animal after the DNA transfer means that all progeny of the produced transgenic animal have the galanin receptor protein in all of their embryonal cells and somatic cells. Descendants (offsprings) of the animal of this type which inherited the gene have the galanin receptor protein in all of their embryonal cells and somatic cells.

The transgenic animal to which the galanin receptor protein DNA is transferred can be subjected to a mating and a breeding for generations under a common breeding circumstance as the animal holding said DNA after confirming that the gene can be stably retained. Moreover, male and female animals having the desired DNA are mated to give a homozygote having the transduced gene in both homologous chromosomes and then those male and female animals are mated whereby it is possible to breed for generations so that all descendants have said DNA.

The animal to which the galanin receptor protein DNA is transferred highly expresses the galanin receptor protein and, accordingly, it is useful as the animal for screening for an agonist or an antagonist to said galanin receptor protein.

The DNA-transferred animal can be used as a cell source for a tissue culture. For example, DNA or RNA in the tissue of the DNA-transferred mouse is directly analyzed or protein tissues expressed by gene are analyzed whereupon the galanin receptor protein can be analyzed. Cells of the galanin receptor protein-containing tissue are cultured by standard tissue culture techniques whereupon it is possible to study the function of the cells which are usually difficult to culture (e.g. those derived from brain and peripheral tissues) using the resulting culture. By using said cells, it is also possible to select the pharmaceuticals which can potentiate, for example, the functions of various tissues. Moreover, if a cell strain with a high expression is available, it is possible to separate and purify galanin receptor proteins therefrom.

In the specification and drawings of the present application, the abbreviations used for bases (nucleotides), amino acids and so forth are those recommended by the IUPAC-IUB Commission on Biochemical Nomenclature or those conventionally used in the art. Examples thereof are given below. Amino acids for which optical isomerism is possible are, unless otherwise specified, in the L form.

| | |
|---|---|
| DNA: | Deoxyribonucleic acid |
| cDNA: | Complementary deoxyribonucleic acid |
| A: | Adenine |
| T: | Thymine |
| G: | Guanine |
| C: | Cytosine |
| RNA: | Ribonucleic acid |
| mRNA: | Messenger ribonucleic acid |
| dATP: | Deoxyadenosine triphosphate |
| dTTP: | Deoxythymidine triphosphate |
| dGTP: | Deoxyguanosine triphosphate |
| dCTP: | Deoxycytidine triphosphate |
| ATP: | Adenosine triphosphate |
| EDTA: | Ethylenediamine tetraacetic acid |
| SDS: | Sodium dodecyl sulfate |
| EIA: | Enzyme Immunoassay |
| G, Gly: | Glycine (or Glycyl) |
| A, Ala: | Alanine (or Alanyl) |
| V, Val: | Valine (or Valyl) |
| L, Leu: | Leucine (or Leucyl) |
| I, Ile: | Isoleucine (or Isoleucyl) |
| S, Ser: | Serine (or Seryl) |
| T, Thr: | Threonine (or Threonyl) |
| C, Cys: | Cysteine (or Cysteinyl) |
| M, Met: | Methionine (or Methionyl) |
| E, Glu: | Glutamic acid (or Glutamyl) |
| D, Asp: | Aspartic acid (or Aspartyl) |
| K, Lys: | Lysine (or Lysyl) |
| R, Arg: | Arginine (or Arginyl) |
| H, His: | Histidine (or Histidyl) |
| F, Phe: | Pheylalanine (or Pheylalanyl) |
| Y, Tyr: | Tyrossine (or Tyrosyl) |
| W, Trp: | Tryptophan (or Tryptophanyl) |
| P, Pro: | Proline (or Prolyl) |
| N, Asn: | Asparagine (or Asparaginyl) |
| Q, Gln: | Glutamine (or Glutaminyl) |
| NVal: | Norvaline (or Norvalyl) |
| pGlu: | Pyroqlutamic acid (or Pyroglutamyl) |
| Blc: | γ-Butyrolacton-γ-carbonyl |
| Kpc: | 2-Ketopiperidinyl-6-carbonyl |
| Otc: | 3-Oxoperhydro-1,4-thiazin-5-carbonyl |
| Me: | Methyl |
| Et: | Ethyl |
| Bu: | Butyl |
| Ph: | Phenyl |
| TC: | Thiazolidinyl-4(R)-carboxamide |

The transformant *Escherichia coli*, designated JM109/p3H2-34, which is obtained in the Example 3 mentioned herein below, is on deposit under the terms of the Budapest Treaty from Oct. 12, 1994, with the National Institute of Bioscience and Human-Technology (NIBH), Agency of Industrial Science and Technology, Ministry of International Trade and Industry, Japan and has been assigned the Accession Number FERM BP-4828. It is also on deposit from Oct. 12, 1994 with the Institute for Fermentation, Osaka, Japan (IFO) and has been assigned the Accession Number IFO 15749.

The transformant *Escherichia coli*, designated JM109/pMGR20, which is obtained in the Example 4 mentioned herein below, is on deposit under the terms of the Budapest Treaty from Dec. 15, 1994, with NIBH and has been assigned the Accession Number FERM BP-4937. It is also on deposit from Dec. 14, 1994 with IFO and has been assigned the Accession Number IFO 15773.

The mouse pancreatic β cell line, designated MIN6, is on deposit under the terms of the Budapest Treaty from Dec. 27, 1994, with NIBH and has been assigned the Accession Number FERM BP-4954. It is also on deposit from Apr. 11, 1995 with IFO and has been assigned the Accession Number IFO 50454.

The transformant *Escherichia coli*, designated SURE/pTS863, which is obtained in the Example 12 mentioned herein below, is on deposit under the terms of the Budapest Treaty from May 25, 1995, with NIBH and has been assigned the Accession Number FERM BP-5110. It is also on deposit from Jun. 1, 1995 with IFO and has been assigned the Accession Number IFO 15826.

The transformant CHO cell, designated CHO/pTS863-5, which is obtained in the Example 13 mentioned herein below, is on deposit under the terms of the Budapest Treaty from May 25, 1995, with NIBH and has been assigned the Accession Number FERM BP-5111. It is also on deposit from June 1, 1995 with IFO and has been assigned the Accession Number IFO 50456.

The transformant CHO cell, designated CHO/pTS863-7, which is obtained in the Example 13 mentioned herein below, is on deposit under the terms of the Budapest Treaty from May 25, 1995, with NIBH and has been assigned the Accession Number FERM BP-5112. It is also on deposit from Jun. 1, 1995 with IFO and has been assigned the Accession Number IFO 50457.

Each SEQ ID NO set forth in the SEQUENCE LISTING of the specification refers to the following sequence:

[SEQ ID NO: 1] is a partial amino acid sequence encoded by the mouse pancreatic β-cell line, MIN6-derived galanin receptor protein cDNA included in p3H2-34,

[SEQ ID NO: 2] is a full length amino acid sequence encoded by the mouse pancreatic β-cell line, MIN6-derived galanin receptor protein cDNA included in pMGR20,

[SEQ ID NO: 3] is a nucleotide sequence of the mouse pancreatic β-cell line, MIN6-derived galanin receptor protein cDNA fragment included in p3H2-34,

[SEQ ID NO: 4] is a nucleotide sequence of the translational unit in the mouse pancreatic β-cell line, MIN6-derived galanin receptor protein cDNA fragment included in pMGR20,

[SEQ ID NO: 5] is a full length amino acid sequence encoded by the human galanin receptor protein cDNA obtained in Example 11.

[SEQ ID NO: 6] is a nucleotide sequence of the translational unit in the human galanin receptor protein cDNA obtained in Example 11.

The practice of the present invention will employ, otherwise indicated, conventional techniques of molecular biology, microbiology, recombinant DNA, pharmacology, immunology, bioscience, and medical technology, which are within the skill of the art. All patents, patent applications, and publications mentioned herein, both supra and infra, are hereby incorporated herein by reference.

EXAMPLES

Described below are working examples of the present invention which are provided only for illustrative purposes, and not to limit the scope of the present invention. In light of the present disclosure, numerous embodiments within the scope of the claims will be apparent to those of ordinary skill in the art. Incidentally, the gene operation using *Escherichia coli* is carried out by a method described in Maniatis, et al.: "Molecular Cloning" (Cold Spring Harbor Laboratory, 1989).

Reference Example 1

Preparation of Synthetic DNA Primer for Amplifying DNA Coding for G Protein Coupled Receptor Protein A comparison of deoxyribonucleotide sequences coding for the known amino acid sequences corresponding to or near the first membrane-spanning domain each of human-derived TRH receptor protein (HTRHR), human-derived RANTES receptor protein (L10918, HUMRANTES), human Burkitt's lymphoma-derived unknown ligand receptor protein (X68149, HSBLR1A), human-derived soma- Gene/Protein Sequencing Data Base (CD019, Hitachi Software Engineering, Japan) and are usually called "Accession Number" or "Entry Names". HTRHR is, however, the sequence as disclosed in Japanese Unexamined Patent Publication No. 286986/1993 (EPA 638645).

Specifically, it was planned to incorporate mixed bases relying upon the base regions that were in agreement with cDNAs coding for a large number of receptor proteins in order to enhance base agreement of sequences with as many receptor cDNAs as possible even in other regions. Based upon these sequences, the degenerate synthetic DNA having a nucleotide sequence represented by SEQ ID NO: 7 which is complementary to the homologous nucleotide sequence and the degenerate synthetic DNA having a nucleotide sequence represented by SEQ ID NO: 8 which is complementary to the homologous nucleotide sequence were produced. Nucleotide synthesis was carried out by a DNA synthesizer.

```
[Synthetic DNAs]                                                         (SEQ ID NO: 7)
5'-CGTGG (G or C) C (A or C) T (G or C) (G or C) TGGGCAAC
   (A, G, C or T) (C or T) CCTG-3'

5'-GT (A, G, C or T) G (A or T) (A or G) (A or G) GGCA       (SEQ ID NO: 8)
   (A, G, C or T) CCAGCAGA (G or T) GGCAAA-3'
``` tostatin receptor protein (L14856, HUMSOMAT), rat-derived μ-opioid receptor protein (U02083, RNU02083), rat-derived κ-opioid receptor protein (U00442, U00442), human-derived neuromedin B receptor protein (M73482, HUMNMBR), human-derived muscarinic acetylcholine receptor protein (X15266, HSHM4), rat-derived adrenaline $\alpha_1$B receptor protein (L08609, RATAADRE01), human-derived somatostatin 3 receptor protein (M96738, HUMSSTR3X), human-derived $C_5$a receptor protein (HUMC5AAR), human-derived unknown ligand receptor protein (HUMRDC1A), human-derived unknown ligand receptor protein (M84605, HUMOPIODRE) and rat-derived adrenaline $\alpha_2$B receptor protein (M91466, RATA2BAR) was made. As a result, highly homologous regions or parts were found.

Further, a comparison of deoxynucleotide sequences coding for the known amino acid sequences corresponding to or near the sixth membrane-spanning domain each of mouse-derived unknown ligand receptor protein (M80481, MUSGIR), human-derived bombesin receptor protein (L08893, HUMBOMB3S), human-derived adenosine A2 receptor protein (S46950, S46950), mouse-derived unknown ligand receptor protein (D21061, MUSGPCR), mouse-derived TRH receptor protein (S43387, S43387), rat-derived neuromedin K receptor protein (J05189, RATNEURA), rat-derived adenosine A1 receptor protein (M69045, RATA1ARA), human-derived neurokinin A receptor protein (M57414, HUMNEKAR), rat-derived adenosine A3 receptor protein (M94152, RATADENREC), human-derived somatostatin 1 receptor protein (M81829, HUMSRI1A), human-derived neurokinin 3 receptor protein (S86390, S86371S4), rat-derived unknown ligand receptor protein (X61496, RNCGPCR), human-derived somatostatin 4 receptor protein (L07061, HUMSSTR4Z) and rat-derived GnRH receptor protein (M31670, RATGNRHA) was made. As a result, highly homologous regions or parts were found.

The aforementioned abbreviations in the parentheses are identifiers (reference numbers) which are indicated when GenBank/EMBL Data Bank is retrieved by using DNASIS The parentheses indicate the incorporation of a plurality of bases, leading to multiple oligonucleotides in the primer preparation. In other words, nucleotide residues in parentheses of the aforementioned DNAs were incorporated in the presence of a mixture of plural bases at the time of synthesis.

Example 1

Preparation of Poly(A)$^+$RNA Fraction from Mouse Pancreatic β-Cell Strain, MIN6 and Synthesis of cDNA A total RNA was prepared from the mouse pancreatic β-cell strain, MIN6 (Jun-ichi Miyazaki et al., Endocrinology, Vol. 127, No. 1, p.126–132) according to the guanidine thiocyanate method (Kaplan B. B. et al., Biochem. J., 183, 181–184 (1979)) and, then, poly(A)$^+$RNA fractions were prepared with a mRNA purifying kit (Pharmacia Co.). Next, to 5 μg of the poly(A)$^+$RNA fraction was added a random DNA hexamer (BRL Co.) as a primer, and the resulting mixture was subjected to reaction with mouse Moloney Leukemia virus (MMLV) reverse transcriptase (BRL Co.) in the buffer attached to the MMLV reverse transcriptase kit to synthesize complementary DNAs. The reaction product was extracted with phenol/chloroform (1:1), precipitated in ethanol, and was then dissolved in 30 μl of TE buffer (10 mM Tris-HCl at pH8.0, 1 mM EDTA at pH8.0).

Example 2

Amplification of Receptor cDNA by PCR Using MIN6-Derived cDNA and Sequencing

By using, as a template, 5 μl of cDNA prepared from the mouse pancreatic β-cell strain, MIN6 in Example 1, PCR amplification using the DNA primers synthesized in Reference Example 1 was carried out. A reaction solution was composed of the synthetic DNA primers each in an amount of 100 pM, 0.25 mM dNTPs, 1 μl of Taq DNA polymerase and 10 µl of 10×buffer attached to the enzyme kit, and the total amount of the reaction solution was made to be 100 µl, The cycle for amplification including 96° C. for 30 sec., 45° C. for 1 min. and 60° C. for 3 min. was repeated 30 times by using a Thermal Cycler (Perkin-Elmer Co.). Prior to adding Taq DNA polymerase, the remaining reaction solution was mixed and was heated at 95° C. for 5 minutes and at 65° C. for 5 minutes. The amplified products were confirmed relying upon 1.2% agarose gel electrophoresis and ethidium bromide staining.

Example 3

Subcloning of PCR Product into Plasmid Vector and Selection of Novel Receptor Candidate Clone via Decoding Nucleotide Sequence of Inserted cDNA Region The PCR products obtained in Example 2 were separated with a 0.8% low-melting temperature agarose gel, the band parts were excised from the gel with a razor blade, and were heat-melted, extracted with phenol and precipitated in ethanol to recover DNAs. According to the protocol attached to a TA Cloning Kit (Invitrogen Co.), the recovered DNAs were subcloned to the plasmid vector, pCR™II (Invitrogen Co.). The recombinant vectors were introduced into *E. coli* JM109 competent cells (Takara Shuzo Co., Japan) to produce transformants. Then, transformant clones having a cDNA-inserted fragment were selected in an LB (Luria-Bertani) agar culture medium containing ampicillin, IPTG (isopropylthio-β-D-galactoside) and X-gal (5-bromo-4-chloro-3-indolyl-β-D-galactoside). Only transformant clones exhibiting white color were picked with a sterilized toothstick to obtain transformant *Escherichia coli* JM109/p3H2-34.

The individual clones were cultured overnight in an LB culture medium containing ampicillin and treated with an automatic plasmid extracting machine (Kurabo Co., Japan) to prepare plasmid DNAs. An aliquot of the DNAs thus prepared was cut by EcoRI to confirm the size of the cDNA fragment that was inserted. An aliquot of the remaining DNAs was further processed with RNase, extracted with phenol/chloroform, and precipitated in ethanol so as to be condensed. Sequencing was carried out by using a DyeDeoxy terminator cycle sequencing kit (ABI Co.), the DNAs were decoded by using a fluorescent automatic sequencer, and the data of the nucleotide sequences obtained were read by using DNASIS (Hitachi System Engineering Co., Japan).

Homology retrieval was carried out based upon the determined nucleotide sequence [FIG. 1]. As a result, it was learned that a novel G protein coupled receptor protein was encoded by the cDNA fragment insert in the plasmid possessed by the transformant *Escherichia coli* JM109/p3H2-34. To further confirm this fact, by using DNASIS (Hitachi System Engineering Co., Japan) the nucleotide sequence were converted into an amino acid sequence [FIG. 1], and homology retrieval was carried out in view of hydrophobicity plotting [FIG. 2] and at the amino acid sequence level to find homology relative to human somatostatin receptor subtype 4 (JN0605), human somatostatin receptor subtype 2 (B41795) and rat-derived ligand unknown receptor (A39297) [FIG. 3]. Abbreviations in parentheses are reference numbers assigned when they are registered as data to NBRF-PIR/Swiss-PROT and are usually called "Accession Numbers" or "Entry Names".

Example 4

Cloning of cDNA containing Whole Coding Region for Receptor Protein from Mouse Pancreatic β-Cell Strain, MIN6-Derived cDNA Library Superscript™ Lambda System (BRL, Cat. 8256) distributed by BRL Co. and Gigapack II Gold (Stratagene, Cat. 200215) distributed by Stratagene Co. were used to construct MIN6-derived cDNA libraries. By using the above kits, a MIN6 cDNA library with $2.2\times10^6$ pfu (plaque forming units) was constructed from 10 µg of MIN6 poly(A)$^+$ RNA. The cDNA library was mixed with *E. coli* Y1090r$^-$ treated with magnesium sulfate, and incubated at 37° C. for 15 minutes followed by addition of 0.5% agarose (Pharmacia Co.) LB. The *E. coli* was plated onto a 1.5% agar (Wako Pure Chemical Co., Japan) LB plate (containing 50 µg/ml of ampicillin). A nitrocellulose filter was placed on the plate on which plaques were formed and the plaque was transferred onto the filter. The filter was denatured with an alkali and then heated at 80° C. for 3 hours to fix DNAs.

The filter was incubated overnight at 42° C. together with the probe mentioned herein below in a buffer containing 50% formamide, 4×SSPE(20×SSPE (pH 7.4) is 3 M NaCl, 0.2 M $NaH_2PO_4\cdot H_2O$, 25 mM EDTA), 5×Denhardt's solution, 0.1% SDS and 100 µg/ml of salmon sperm DNA for hybridization.

The probe used was obtained by cutting the DNA fragment inserted in the plasmid, p3H2-34, obtained in Example 2, with EcoRI, followed by recovery and labeling by incorporation of [$^{32}$P]dCTP (Dupont/NEN) with a random prime DNA labelling kit (Amersham Co.).

It was washed with 2×SSC (150 mM NaCl and 15 mM sodium citrate), 0.1% SDS at 55° C. for 1 hour and, then, subjected to an autoradiography at −80° C. to detect hybridized plaques.

In this screening, hybridization signals were recognized in two independent plaques. Each DNA was prepared from the two clones. The DNAs digested with SalI and NotI were subjected to an agarose electrophoresis and were analyzed. Inserted fragments were identified at about 2.0 kb and 3.0 kb, respectively. Between them, the DNA fragment corresponding to the band at about 3.0 kb (λ No. 20) was selected. The λ No. 20-derived NotI-SalI fragment with about 3.0 kb was subcloned into the NotI-SalI site of the plasmid, pbluescript™II SK(+), and *E. coli* JM109 was transformed with the plasmid to obtain a transformant *E. coli* JM109/pMGR20. A restriction enzyme map of the plasmid, pMGR20, was prepared relying upon a restriction enzyme map deduced from the nucleotide sequence as shown in Example 2. As a result, it was learned that it carried a full-length receptor protein-encoding DNA which was predicted from the receptor protein-encoding DNA as shown in Example 2.

Example 5

Sequencing of MIN6-Derived Receptor Protein Full-Length cDNA

Among the NotI-SalI fragments inserted in the plasmid, pMGR20, obtained in Example 4, the nucleotide sequence with total 1607bp, including not only a region that is considered to be a receptor protein-coding region (ORF) but also a neighboring region thereof was sequenced. Concretely speaking, by utilizing restriction enzyme sites that exist in the NotI-SalI fragments, unnecessary parts were removed or necessary fragments were subcloned in order to prepare template plasmids for analyzing the nucleotide sequence thereof. As for the nucleotide sequences of part of the regions, primers for sequencing were synthesized based upon the nucleotide sequences that were determined already and used to make confirmation.

The reaction for determining the nucleotide sequence (sequencing) was carried out with a DyeDeoxy terminator cycle sequencing kit (ABI Co.), the DNA was decoded with the fluorescent automatic sequencer (ABI Co.), and the data of the nucleotide sequence obtained were analyzed with DNASIS (Hitachi System Engineering Co., Japan).

FIG. 4 shows a nucleotide sequence around an open reading frame (ORF) of a mouse galanin receptor protein encoded by the cDNA insert in pMGR20. The nucleotide sequence of mouse galanin receptor protein-encoding DNA corresponds to from the 481st to 1525th nucleotides of the nucleotide sequence in FIG. 4. The amino acid sequence of the receptor protein encoded by the DNA insert was that as represented by SEQ ID NO: 2 (FIG. 4). Since the amino acid sequence has 92% homology to the human-derived galanin receptor protein at the amino acid sequence level, it was learned that the cDNA insert in the pMGR20 is a mouse-derived galanin receptor protein-encoding cDNA.

Example 6

Galanin Receptor Binding Experiment using MIN6 Cell Membrane Fraction (1) Preparation of Membrane Fractions from MIN6 Cells.

MIN6 cells were cultured by a known method (Endocrinology, vol. 127, pages 126–132, 1990). Thus, the culturing was carried out in a Dulbecco modified Eagle's medium containing 15% of fetal bovine serum, 4.5 g/liter of glucose, 5 µl/liter of mercaptoethanol, 75 mg/ml of penicillin and 50 mg/ml of streptomycin in the presence of 5% carbon dioxide gas. The cultured cells were washed with PBS containing EDTA and exfoliated from the culturing device. The exfoliated cells were recovered by centrifugation and subjected to the following method of preparing the membrane fractions.

The recovered cells (about 2.5 ml) were suspended in a buffer for homogenization (containing 10 mM of $NaHCO_3$, 5 mM of EDTA, 0.5 mM of PMSF, 10 µg/ml of pepstatin, 20 µg/ml of leupeptin and 4 µg/ml of E-64; pH: 7.2) and homogenized with a polytron homogenizer (Kinematica) at 23,000 rpm for one minute. The resulting homogenate was centrifuged in a Hitachi RP24A rotor using a Hitachi High-Speed Centrifuging Machine (type: CR26H) at 5,000 rpm for ten minutes. The supernatant liquid after centrifugation was recovered and subjected to an ultracentrifugation in a Hitachi RP42 rotor using a Hitachi Ultracentrifugal Machine (type: SCP70H) at 30,000 rpm for one hour to give pellets. The resulting pellets were again suspended in a buffer for the homogenization and stored at −70° C. until its actual use.

(2) Receptor Binding Experiment using MIN6 Cell Membrane Fractions.

The MIN6 cell membrane fractions prepared by the method of the above-mentioned (1) were diluted with a buffer for the receptor binding experiment (containing 20 mM of Tris, 1 mM of EDTA, 0.03% of $NaN_3$, 0.1% of BSA, 0.05% of CHAPS, 0.5 mM of PMSF, 10 µg/ml of pepstatin, 20 µg/ml of leupeptin and 4 µg/ml of E-64; pH: 7.4) to make the membrane protein concentration 50µg/ml. Each 100 µl of the diluted membrane fractions was charged in a test tube made of polypropylene (Falcon; type 2038) and subjected to the following receptor binding experiment. In the meanwhile, porcine galanin (New England Nuclear) which was labeled with a commercially available [$^{125}$I] radioisotope was diluted with a buffer for the receptor binding experiment to make its concentration 5 nM and used in the following experiments.

Standard porcine galanin solution or galanin-related peptide solution (3 µl) with varied concentrations and 2 µl of 5 nM labeled galanin solution were mixed with 100 µl of the above-mentioned membrane fraction. The mixture was allowed to stand in a water bath of 25° C. for 75 minutes to promote the receptor binding reaction. Thereafter, 1.5 ml of an ice-cooled buffer for the binding experiment was added to the reaction solution for quenching the binding reaction and filtered with a glass fiber filter (GF/F, manufactured by Whatman) immediately whereupon the membrane fractions were collected on the filter paper. Then the filter paper was washed with 1.5 ml of the same buffer and the amount of the radioisotope in the filter paper was determined by a gamma-ray detector.

Amount of the labeled galanin bound therewith was expressed in terms of PMB (percent of maximum binding) as calculated by the following equation (2):

$$PMB = [(B-NSB)/(B_0-NSB)] \times 100 \qquad (2)$$

in which PMB: percent of maximum binding

B: the value when the sample is added

NSB: nonspecific binding amount (the binding amount of the labeled galanin in the presence of 1 µM of standard galanin)

$B_0$: maximum binding amount (the binding amount of the labeled galanin in the absence of the standard porcine galanin)

Figure 7:
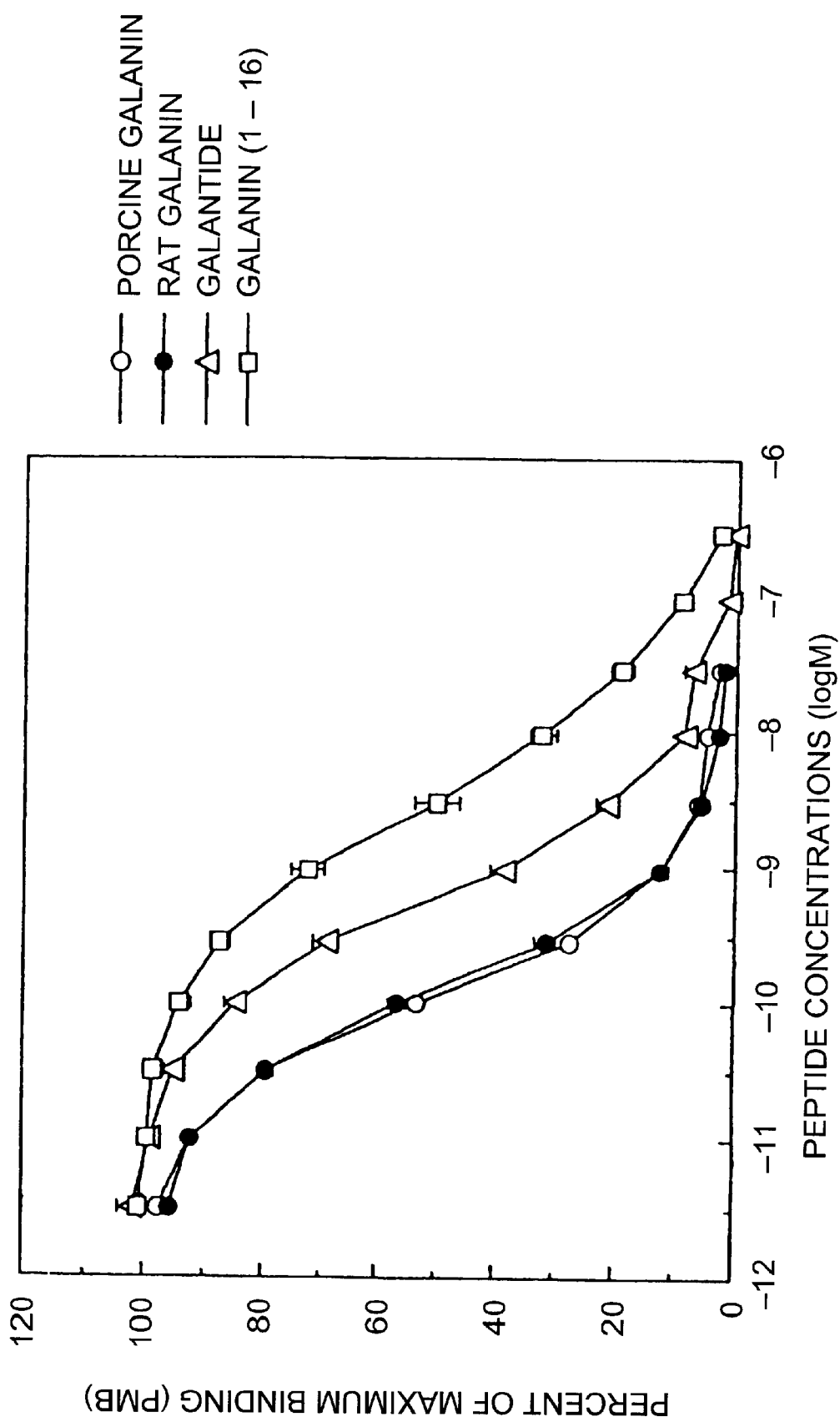
FIG. 7 is the plotting profile of the binding amounts (PMB) of labeled galanin to MIN 6 cells against the concentrations of standard porcine galanin, rat galanin, galanin (1–16) partial peptide or galanin antagonist (galantide).

The result wherein the binding amounts (PMB) of the labeled galanin as determined hereinabove were plotted against the concentrations of standard porcine galanin, rat galanin, galanin (1–16) partial peptide or galanin antagonist (galantide) is shown in FIG. 7. From the result, each of the concentrations ($IC_{50}$) giving 50% of PMB was calculated and given in Table 1.

TABLE 1

| Peptides | $IC_{50}$ |
| --- | --- |
| Porcine Galanin | 0.12 nM |
| Rat Galanin | 0.13 nM |
| Galanin (1–16) | 3.3 nM |
| Galantide | 0.69 nM |

It is noted from Table 1 that, when the cell membrane fractions of MIN6 cells were used, the receptor binding affinity of the ligand to the galanin receptor was able to be determined by means of a galanin receptor binding experiments.

Example 7

Screening of Galanin Receptor Agonist/Antagonist by Galanin Receptor Binding Experiments It is possible to conduct a screening of galanin receptor angonist/antagonist by a method mentioned in Example 6. Thus, 1 µl of the solution of test compounds and 2 µl of a 5 nM labeled galanin solution are mixed with 100 µl of MIN6 cell membrane fractions by the same manner as in Example 6. Thereafter, the binding amount is determined by the same manner as in Example 6 whereby the compounds which decreased the PMB to an extent of lower than a certain level are screened as galanin receptor agonists/antagonists.

Example 8

Detection for Biological Activity of Galanin Using MIN6 Cells

It has been known that galanin is biologically active in inhibiting the insulin secretion of a Langerhans islet of pancreas by stimulation of glucose. Such an activity can be easily detected by the following methods using MIN6 cells. Among the detecting methods, measurement of insulin secretion by glucose stimulation was principally conducted according to a known method (Diabetologia, volume 36, pages 1139–1145, 1993).

Briefly, $3 \times 10^5$ MIN6 cells were seeded on a 24-well plate and cultured in a Dulbecco modified Eagle's medium (supplemented with 15% of fetal bovine serum, 4.5 g/liter of glucose, 5 μl/liter of mercaptoethanol, 75 mg/ml of penicillin and 50 mg/ml of streptomycin) in the presence of 5% carbon dioxide gas for three days.

The cells were washed for three times with a Krebs-Ringer- HEPES buffer (containing 119 mM of NaCl, 4.74 mM of KCl, 2.54 mM of $CaCl_2$, 1.19 mM of $MgSO_4$, 1.19 mM of $KH_2PO_4$, 25 mM of $NaHCO_3$, 10 mM of HEPES and 0.5% of BSA) and cultured in a Krebs-Ringer-HEPES buffer to which 5 mM of glucose was added at 37° C. for 30 minutes.

Then the cells were washed with the Krebs-Ringer-HEPES buffer twice. The cells were cultured at 37° C. for 90 minutes in a Krebs-Ringer-HEPES buffer to which a varied amount of rat galanin and 25 mM of glucose. The supernatant liquid after the culturing was collected and the amount of insulin which was secreted into the supernatant liquid was determined by a commercially available radioimmunoassay kit (Amersham).

Figure 8:
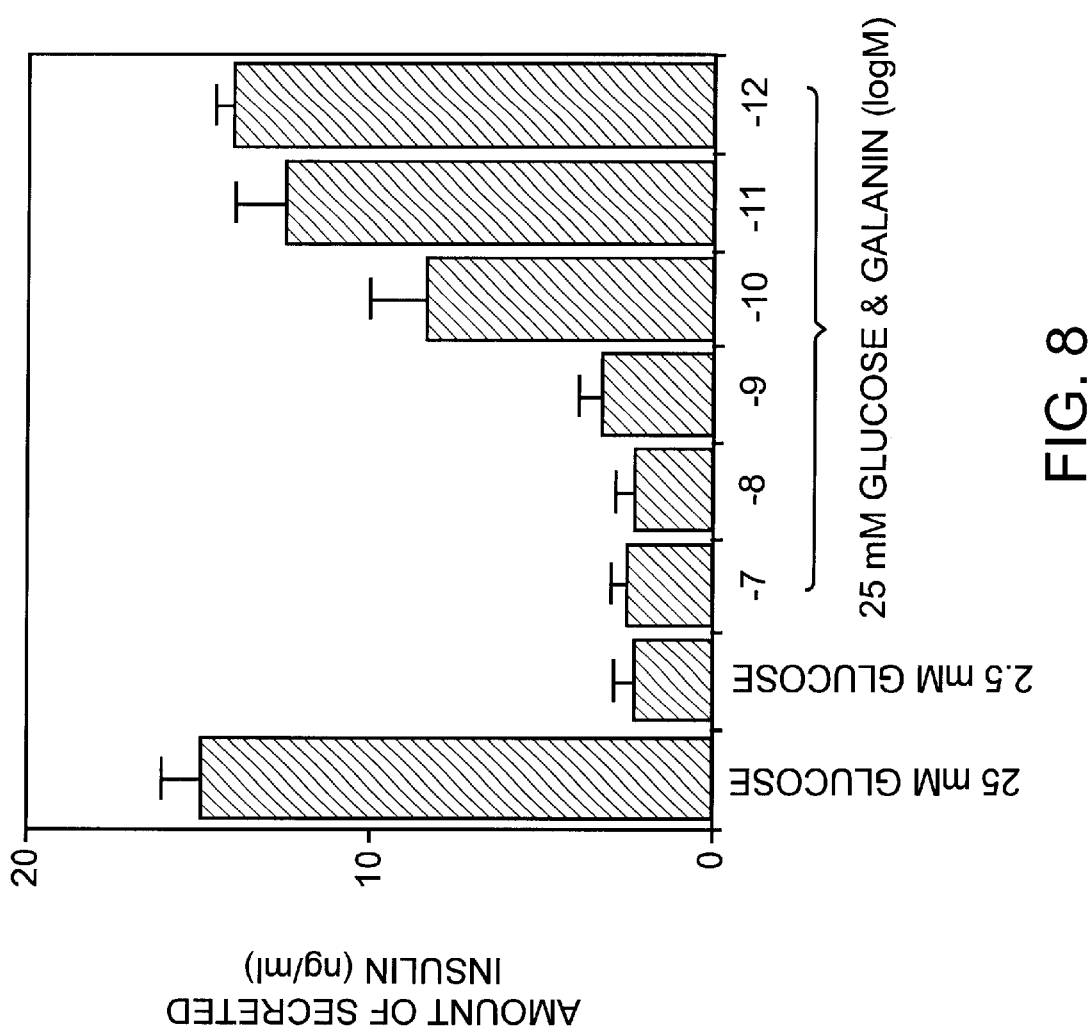
FIG. 8 is the plotting profile of the amount of insulin secretion from MIN 6 cells against the amount of galanin.

FIG. 8 shows the result in which the amount of insulin secretion was plotted against the amount of galanin. It is apparent from FIG. 8 that, when about 100 pM of galanin is added, the insulin secretion which increased by a glucose stimulation is decreased to an extent of about one half. As such, it is now clear that the activity of galanin can be easily detected using the above-mentioned method.

Example 9

Detection for Biological Activity of Galanin Using MIN6 Cells

When MIN6 cells were treated with forskolin, the cAMP concentration in the cells increased whereupon secretion of insulin increased. Such a phenomenon can be inhibited by addition of galanin and can be used as a method of measuring the biological activity of galanin.

The cells which were cultured and pretreated (by the operations of washing, treating with 5 mM of glucose and washing) by the same manner as in Example 8 were cultured at 37° C. for 90 minutes in a Krebs-Ringer-HEPES buffer to which varied concentration of rat-type galanin, 100 μM of forskolin, 200 μM of isobutylmethylxantine (IBMX) and 6.25 mM of glucose were added.

Figure 9:
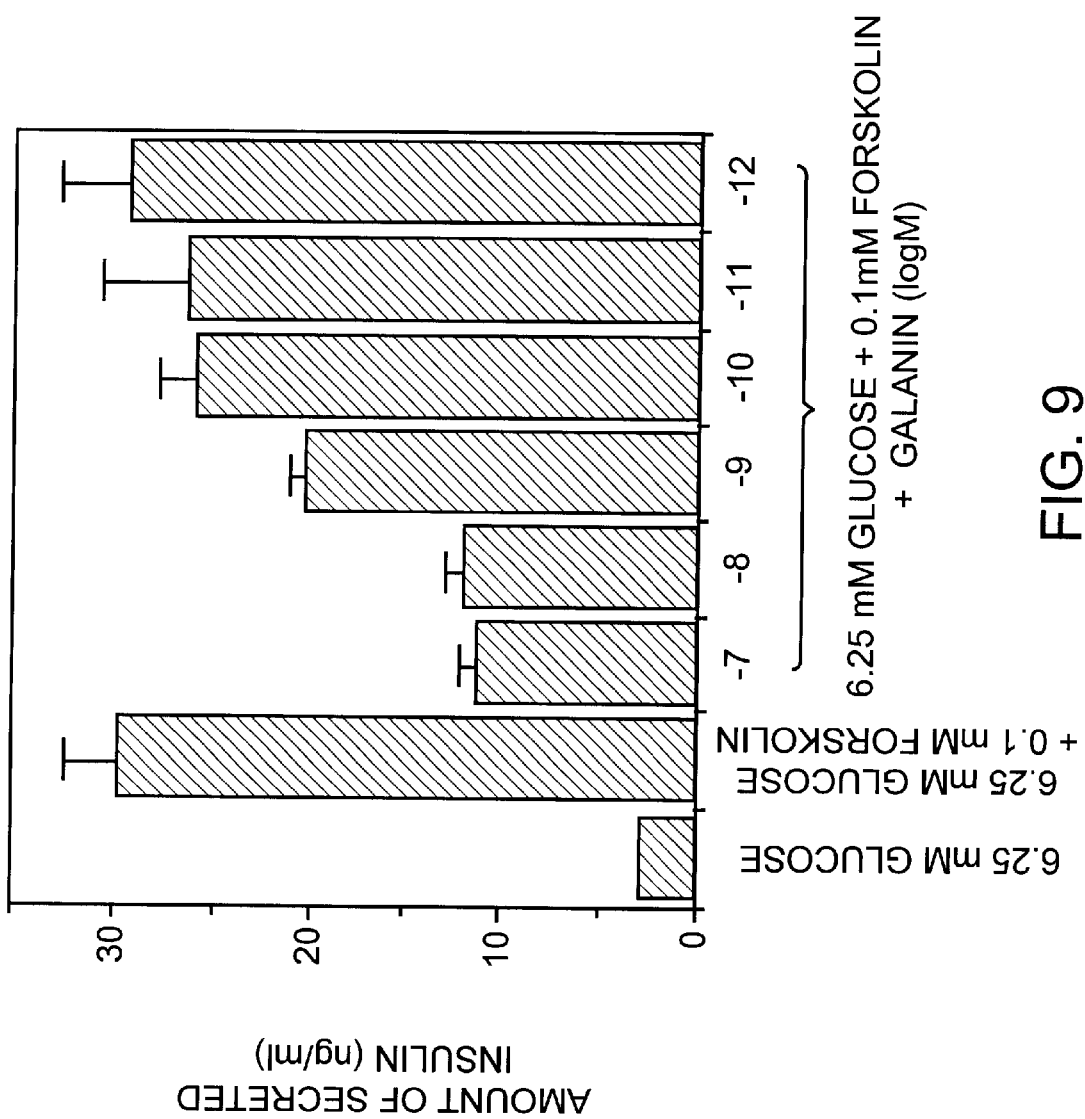
FIG. 9 is the plotting profile of the amount of insulin secretion from MIN 6 cells against the amount of galanin.
Figure 10:
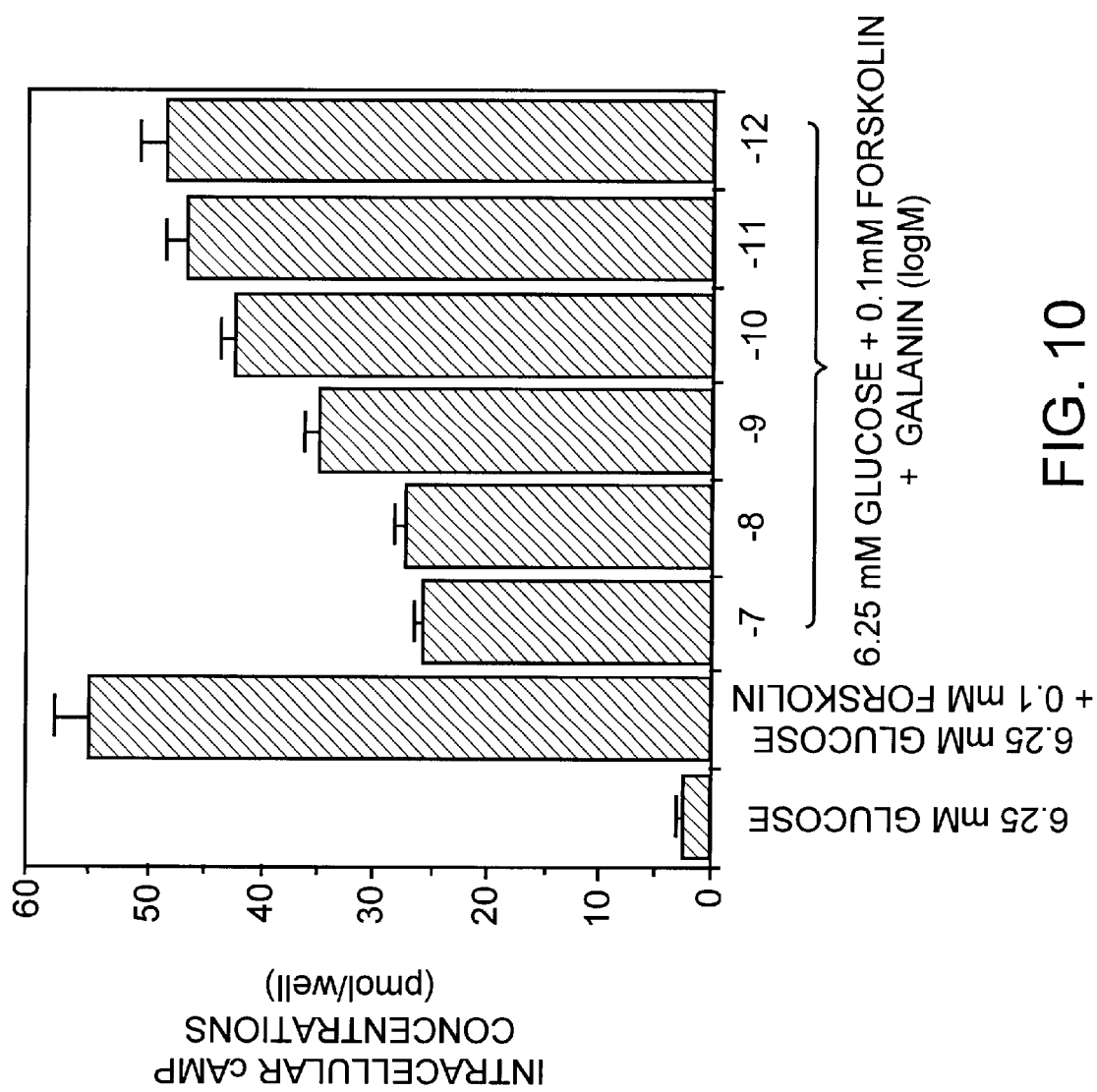
FIG. 10 is the plotting profile of the amount of intracellular cAMP in MIN 6 cells against the amount of galanin.

The supernatant after the culturing was recovered and the amount of insulin which was secreted into the supernatant was determined by a commercially available radioimmunoassay kit (Amersham). In addition, the cells were treated with perchloric acid to extract the cAMP in the cells and the cAMP in the extract was determined by a commercially available radioimmunoassay kit (Amersham). FIG. 9 shows the result in which the secreted amount of insulin is plotted against the amount of galanin. FIG. 10 shows the result in which the amount of intracellular cAMP was plotted. From FIG. 9 and FIG. 10, it is noted that the activity of galanin can be easily detected when secretion of insulin from MIN6 cells or cAMP concentration in MIN6 cells was measured.

Example 10

Detection for Biological Activity of Galanin Agonist/Antagonist Using MIN6 Cells It is possible to measure the activity of galanin agonist/antagonist by a method as mentioned in Example 8. Briefly, the cells which are cultured and pretreated (by the operations of washing, treating with 5 mM of glucose and washing) by the same manner as in Example 8 are cultured at 37° C. for 90 minutes in a Krebs-Ringer-HEPES buffer to which a suitable concentration of test compounds, 100 pM of rat galanin and 25 mM of glucose are added.

The supernatant liquid after the culturing is recovered and the amount of insulin secreted into the supernatant liquid is determined using a commercially available radioimmunoassay kit (Amersham). As a control, the amount of insulin is determined by the same manner for the supernatant liquid obtained after culturing in a Krebs-Ringer-HEPES buffer containing 25 mM glucose only and also in a Krebs-Ringer-HEPES buffer containing 100 pM of rat galanin and 25 mM of glucose. It is noted from the result that the activity of galanin agonist/antagonist can be easily measured using MIN6 cells.

Example 11

Cloning of cDNA Coding for Human Galanin Receptor Protein

Human melanoma Bowes cells were cultured using a DMEM medium with high concentrations of glucose containing 10% fetal bovine serum at 37° C. under the condition of 95% air/5% $CO_2$ and, when it became almost confluent, total RNA was prepared by a guanidine-thiocyanate method. From the resulting total RNA was prepared a poly $A^+RNA$ fraction by an oligo(dT) cellulose column. The poly $A^+RNA$ (10 μg) was treated with a random hexamer and a reverse trasnscriptase to synthesize a single-stranded DNA and then treated with *Escherichia coli* DNA polymerase I and RNase H to synthesize a double-stranded DNA whereupon a double-stranded cDNA was synthesized from poly $A^+RNA$. This double-stranded cDNA was blunt ended with a T4 DNA polymerase and then EcoRI adapters were added thereto. The resulting double-stranded cDNA wherein both terminals were added with EcoRI adapters was subjected to a gel filtration to remove cDNA of about 1,000 bp and less and then phosphate group was introduced into the EcoRI adapters using a T4 polynucleotide kinase.

Then this cDNA was incorporated into a γgt11 EcoRI arm and subjected to an in vitro packaging to prepare a cDNA library (average chain length: about 1.6 kbp; rate of insertion: 98%) of melanoma Bowes cells having about $1.5 \times 10^6$ pfu in total. The γ phage of this cDNA library was infected with *Escherichia coli* Y1090r⁻ strain, seeded on each of soft agar plates at about $1.8 \times 10^4$ plaques each and incubated overnight at 42° C. to form plaques. The plaques were transferred to a nitrocellulose filter, successively treated with a modifying solution (0.5N sodium hydroxide and 1.5M sodium chloride), a neutralizing solution (0.5M Tris-HCl (pH: 7.0) and 1.5M sodium chloride) and 3×SSC (20×SSC= 3M sodium chloride and 0.3M sodium citrate), air-dried and baked at 80° C. for three hours whereupon the phage DNA was immobilized on the nitrocellulose filter.

On the other hand, in order to obtain the cDNA fragments to be used as a probe, synthetic oligonucleotides ① and ② were synthesized based upon a base sequence of the known human galanin receptor cDNA [Habert-Ortoll, E. et al., Proceedings of the National Academy of Sciences of the U.S.A., 91, 9780–9783 (1994)].

① (SEQ ID NO: 9)
5'-TCCGTGGACCGCTACGTGGCCATCGTG-3'

It is a synthetic oligonucleotide containing a sense sequence of +388 to +414 (wherein the translation initiation site was named +1).

② (SEQ ID NO: 10)
5'-GACTTATCACACATGAGTACAATTGGTTGATGG-3'

It is a synthetic oligonucleotide containing an antisense sequence of +1024 to +1053.

An RT-PCR was carried out using those two synthetic nucleotides as primers and 5 μg of human melanoma Bowes cell poly A⁺RNA as a template whereupon cDNA fragments of 669 bp containing C-terminals of human galanin receptor protein were obtained. The cDNA fragments were incorporated into the HincII site of pUC119 to give a plasmid pHGR54-7. The pHGR54-7 was subjected to a double digestion with BamHI and HincII and the resulting cDNA fragments containing the human galanin receptor protein C-terminal were used as probes for screening the human melanoma Bowes cell cDNA library.

Labeling of the probes was conducted by subjecting the above-mentioned cDNA fragments to a random priming method using [α-$^{32}$P]dCTP. A hybridization was carried out at 85° C. in a buffer for hybridization (5×SSPE, 5× Denhardt's solution, 100 μg/l thermally modified salmon sperm DNA, 0.1% SDS) containing labeled probes. The filter was finally washed in 0.1×SSC, 0.1% SDS solution at 50° C. and subjected to an autoradiography to detect the plaques which were hybridized with the probes.

Figure 12A:
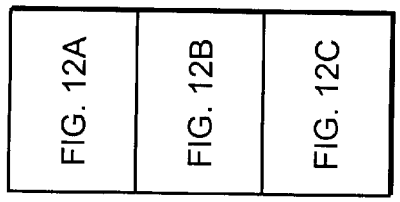
FIG. 12 is the nucleotide sequence nucleotides 1127-1882 of (SEQ ID NO: 15) and deduced amino acid sequence (136th to 349th) amino acids 136-349 of (SEQ ID NO: 5) of the human galanin receptor protein obtained in Example 11.

After the phage DNA was extracted from the phage clone lambda HGR2 obtained by that method, cDNA fragments were cut out by digesting with a restriction enzyme EcoRI and inserted into the EcoRI sites of the pUC118 plasmid to give pHGR2-3. The base sequence of the cDNA fragments inserted thereinto was determined by a conventional method using [α-$^{32}$P]dCTP whereupon it was found that said cDNA fragment was composed of 1,882 bp (FIG. 11 and FIG. 12; SEQ ID NO: 6). There was one substitution with a base as compared with the base sequence of the human galanin receptor cDNA which was reported already [Habert-Ortoll, E. et al., Proceedings of the National Academy of Sciences of the U.S.A., 91, 9780–9783 (1994)]. Said substitution with a base was within a translation domain and is accompanied by an amino acid substitution, i.e., $^{15}$Cys(TGT)→$^{15}$Trp (TGG) (FIG. 11 and FIG. 12; SEQ ID NO: 6). As such, a plasmid pHGR2-3 containing the human galanin receptor DNA fragments was obtained.

Example 12

Construction of Expression Plasmid containing Human Galanin Receptor Protein cDNA pAKKO-111 (shown as pA1-11 in FIG. 13) was used as an expression vector. The pAKKO-111 was constructed as follows: Briefly, pTB1417 according to Japanese Unexamined Patent Publication No. Hei-05/076385 was treated with HindIII and ClaI to give DNA fragments of 1.4 kb containing SRα promoters and poly A added signals. Further, pTB348 [Naruo, K. et al., Biochemical and Biophysical Research Communications, 128, 256–264(1985)] was treated with ClaI and SalI to give DNA fragments of 4.5 kb containing dihydrofolate reductase (dhfr) genes. Those DNA fragments were blunt ended with a T4 polymerase and ligated by a T4 ligase to construct pAKKO-111 plasmid.

Human galanin receptor cDNA expression plasmid was prepared by a method as shown in FIG. 13 from the plasmids pHGR2-3 and pHGR54-7 containing the human galanin receptor cDNA fragments obtained in Example 11. First, pHGR2-3 was subjected to a double digestion using restriction enzymes BamHI and MunI and the resulting DNA fragments of about 1,190 bp were inserted between BamHI and MunI sites of pHGR54-7. In the meanwhile, pHGR2-3 was digested with NcoI, the resulting fragments of 495 bp were blunt ended with DNA polymerase I Klenow fragments, SalI linkers were added thereto, then subjected to a double digestion with AgeI and SacII and the resulting DNA fragments of 200 bp were inserted between XmaI and SacII sites of the above-prepared plasmid whereupon a plasmid pTS862 which contained the translation unit only of the human galanin receptor cDNA was obtained.

Finally, SalI DNA fragments containing the translation domain of the human galanin receptor protein cDNA of about 1.0 kbp obtained by digesting the plasmid pTS862 with SalI were introduced into the SalI site of pAKKO-111 in a regular order to give a human galanin receptor protein cDNA expression plasmid pTS863. This expression plasmid pTS863 was introduced into *Escherichia coli* to give a transformant *Escherichia coli* SURE/pTS863.

Example 13

Expression of Human Galanin Receptor Protein cDNA in CHO (dhfr⁻) Cells

Four kinds of CHO (dhfr⁻) cells (in which cell numbers were stepwisely changed within a range of 3×10⁴ to 1×10⁶ cells) were sowed on laboratory dishes with 10 cm diameter and cultured for 24 hours with a Ham's F12 medium containing 10% of fetal bovine serum. The human galanin receptor cDNA expression plasmid pTS863 (1.5 μg) obtained in Example 12 was transfected to the above-prepared cells by a calcium phosphate method. After 24 hours from the transfection, the medium was substituted with a DMEM medium containing 10% of dialyzed fetal bovine serum and the cells wherein the plasmid was incorporated in chromosomes were selected. Colonies of the selected cells were cloned to give two clones of cell strains CHO/pTS863-5 and CHO/pTS863-7 which highly expressed the human galanin receptor in a stable manner.

Example 14

Measurement of Human Galanin Receptor Activity of Human Galanin Receptor Expression CHO Cells Human galanin receptor expression CHO cells were seeded on a 12-well plate, cultured at 37° C. under the condition of 95% air/5% CO₂ using a DMEM medium containing 10% of dialyzed fetal bovine serum until a confluent was resulted and the medium was exchanged on one day before the binding experiment was done whereupon the human galanin receptor having an amino acid sequence having SEQ ID NO: 5 was expressed.

Then the binding experiment to [$^{125}$I] galanin (porcine) was conducted as follows. First, the cells were washed twice with each 1 ml of a buffer for measuring a binding (Hanks solution containing 0.1% BSA and 0.05% of CHAPS) warmed at 37° C., said buffer for binding measurement was sucked, then 0.5 ml of a buffer for binding measurement containing 100 pM of [$^{125}$I] galanin (porcine) was added and a binding reaction was carried out for one hour at 37° C. under the condition of 95% air/5% $CO_2$. After completion of the reaction, the buffer for the binding measurement was removed and washed thrice with each 1 ml of a buffer for the binding measurement warmed at 37° C. The amount of [$^{125}$I] galanin (porcine) bound with the cells was measured by a gamma-counter after removing the cells with 0.2N sodium hydroxide and was defined as a total binding amount. Incidentally, the same operation was conducted after adding 1 μM of unlabeled galanin (porcine) at the binding reaction and the amount of [$^{125}$I] galanin bound with the cells was defined as the nonspecific binding amount. The results are given in Table 2.

TABLE 2

| Cell Strain No. | Total Binding Amt. (cpm) | Nonspecific Binding Amt (cpm) |
| --- | --- | --- |
| CHO/pTS863-5 | 50466.8 ± 502.9 | 1458 ± 100.1 |
| CHO/pTS863-7 | 59158.6 ± 2095.1 | 1962.4 ± 56.3 |

It was confirmed from Table 2 that CHO/pTS863-5 and CHO/pTS863-7 which are cell strains expressing the human galanin receptor protein of the present invention in a high and stable manner were capable of specifically binding with galanin which is a ligand.

Example 15

Saturation Binding Experiments and Scatchard Plot Analysis with Human [$^{125}$I] Galanin in GAL5 Cell Membrane Fractions CHO cells expressing human galanin receptor proteins (GAL5 cell, denoted by CHO/pTS863-5 in Example 13) were cultured in a DMEM medium containing 10% dialyzed serum, 2 mM glutamine, penicillin and streptomycin at 37° C. under the condition of 95% air/5% $CO_2$. The cells were collected with a phosphate-buffered saline (PBS) containing 1 g/l EDTA, suspended in a buffer for homogenization (10 mM HEPES, 5 mM EDTA, 0.03 % $NaN_3$, 10 μg/ml of pepstatin, 0.5 mM phenylmethylsulfonyl fluoride (PMSF), 20 μg/ml of E-64, 40 μg/ml of leupeptin, pH 7.3) and homogenized with a Polytron homogenizer. The resultant homogenates were centrifuged at 2,500 rpm for 10 min under 4° C. The resultant supernatant was ultracentrifuged at 30,000 rpm for 60 min under 4° C. Pellets were suspended in a buffer for homogenization to form a suspension as a GAL5 cell membrane fraction.

The GAL5 cell membrane fraction was diluted with an assay buffer (20 mM Tris., 1 mM EDTA, 0.08 % $NaN_3$, 10 μg/ml of pepstatin, 0.5 mM PMSF, 20 μg/ml of E-64, 40 μg/ml of leupeptin, 0.1% BSA, and 0.05% CHAPS, pH 7.4) to make the membrane protein concentration 2 μg/ml. Each 100 μl of the diluted membrane fractions was charged in a test tube.

The GAL5 cell membrane fractions were incubated with 15 pM to 500 pM concentrations of human [$^{125}$I] galanin for 75 min at 25° C., then diluted with 1.5 ml of a filtration buffer (20 mM Tris., 1 mM EDTA, 0.03 % $NaN_3$, 0.1% BSA, and 0.05% CHAPS, pH 7.4, 4° C.) and subjected to filtration through glass fiber filters (GF/F, Whatman, Kent, UK) treated with polyethylenimine. The filters were rinsed with 1.5 ml of the same filtration buffer and the radiolabeled ligands remaining were quantitated with an auto-γ-counter (Beckman Instruments, Inc., Palo Alto, Calif.). Nonspecific binding was determined in the presence of 20 nM of unlabeled human galanin. Scatchard plot analysis indicated its dissociation constant ($K_d$) of 20 pM and maximal number of binding sites ($B_{MAX}$) of 9.6 pmol/mg protein.

Example 16

Northern Blot Analysis Using Mouse Galanin Receptor Protein Encoding cDNA

Figure 14:
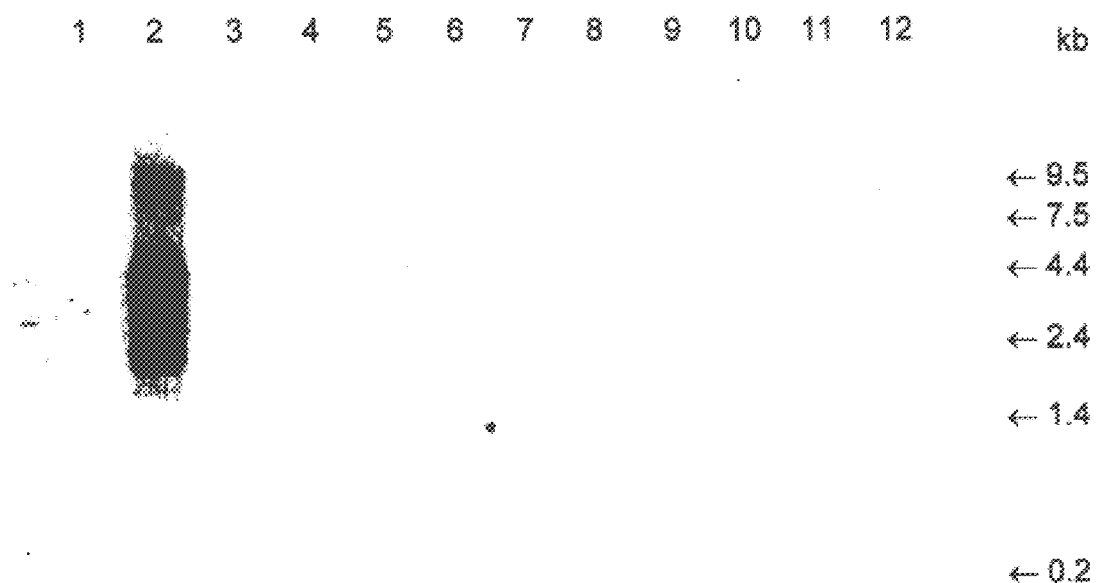
FIG. 14 depicts a profile of northern blot analysis of poly(A)$^+$RNA from mouse tissues, Neuro-2a, and MIN6 cells with p3H2-34. Poly(A)$^+$RNA (5 μg/lane) was denatured by treatment with glyoxal and then electrophoresed on a 1.2% agarose gel. The RNAs were transferred onto a nitrocellulose filter and hybridized with a $^{32}$P-labeled cDNA insert of p3H2-34 as a probe. Lanes: 1, Neuro-2a; 2, MIN6; 3, intestinal smooth muscle; 4, testis; 5, pancreas; 6, kidney; 7, liver; 8, heart; 9, lung; 10, spleen; 11, thymus; 12, brain.

Five micrograms of poly (A)$^+$RNAs from mouse brain, thymus, spleen, lung, heart, liver, kidney, pancreas, testis, intestinal smooth muscle, MIN6, and Neuro-2a were electrophoresed on 1.2% agarose gel after denaturation with glyoxal and dimethyl sulfoxide (Thomas, P. S., Proc. Natl. Acad. Sci. U.S.A., 77, 5201–5205, 1980). After the electrophoresis, the RNAs were transferred onto a nitrocellulose filter (Schleicher & Schuell, Dassel, Germany) and the filter was baked at 80° C. for 2 hr. As a probe, the cDNA insert of p3H2-34 was excised by EcoRI digestion and labeled with [α-$^{32}$P]dCTP(222 TBq/mmol, Dupont/NEN) by a Multiprime DNA labeling kit (Amersham International PLC, Amersham Place, UK). Hybridization was conducted overnight at 42° C. in a buffer containing 50% formamide, 5×SSC, 50 mM $NaHPO_4$, pH 6.5, 10× Denhardt's solution, and 100 μg/ml salmon sperm DNA. The filter was then washed with 2×SSC, 0.1% SDS at 50° C., and then autoradiographed at −80° C. for 12 days on an X-Omat film AR (Eastman Kodak Company, Rochester, N.Y.) with an intensifying screen. In Northern blot analysis using poly(A)$^+$ RNAs from mouse tissues, the faintly hybridizing signals for the mouse galanin receptor only in the brain and small intestine (FIG. 14) were detected . The result of the Northern blot indicated that the expression level of galanin receptor mRNA was substantially lower in mouse normal tissues.

Example 17

(1) Expression of Mouse Galanin Receptor cDNA in CHO Cells

A cDNA clone with a complete translation unit, pMGR20 (obtained in Example 4), was digested with NotI, blunt ended, and ligated with XbaI linker (Takara Shuzo Co., Ltd., Kyoto, Japan). The cDNA fragment was excised by SalI and XbaI digestion and inserted between SalI and SpeI sites of a mammalian cell expression vector, pAKKO-111H (Hinuma, et al., Biochim. Biophys. Acta, 1219, 251–259 (1994)).

A resultant expression plasmid with the mouse galanin receptor cDNA downstream of the SRα promoter and with dhfr gene as a selection marker was designated as pAKKO-MGR20. The plasmid DNA was transfected into CHO dhfr$^-$ cells with a CellPhect Transfection Kit (Pharmacia). Transformants were selected in α-MEM medium without deoxyribonucleoside and ribonucleoside (GIBCO BRL) supplemented with dialyzed fetal bovine serum (GIBCO BRL).

(2) Binding Assay with Porcine [$^{125}$I] Galanin

CHO cells transformed with pAKKOMGR20 and pAKKO-111H were grown in a 12-well tissue culture plate at 2.0×10$^5$ cells/well and cultured for one day. After two washings with Hanks' balanced salt solution (HBSS) containing 0.1% BSA, the cells were incubated with 100 pM porcine [$^{125}$I] galanin (Dupont/NEN) at room temperature for 1 hour in the presence or absence of unlabeled porcine galanin (1 μM at final concentration). The cells were then washed three times with HBSS containing BSA, lysed with 0.1N NaOH, 1% SDS, and the radiolabeled ligands remaining were quantitated with an auto-γ-counter (Beckman Instruments, Inc., Palo Alto, Calif.). For competitive binding experiments and Scatchard plot analysis, membrane fractions were prepared from the transformed CHO cells. The cells grown in 225-cm$^2$ tissue culture flasks for three days were dispersed in a phosphate-buffered saline (PBS) containing 5 mM EDTA and then harvested by centrifugation. The cells were washed with the same buffer, and then suspended in 10 mM sodium carbonate buffer (pH 7.5), including 1 mM EDTA, 0.5 mM phenylmethylsulfonyl fluoride (PMSF), 20 μg/ml of leupeptin, 4 μg/ml of E-64, and 0.5 μg/ml of pepstatin. After the cells were homogenized with a Polytron homogenizer, the homogenates were centrifuged at 3,000 rpm for 10 min in a Hitachi RR2A2 rotor. The resultant supernatant was ultracentrifuged at 30,000 rpm for 60 min in a Beckman Type 30 rotor. Pellet suspension was then done in a buffer containing 20 mM Tris-HCl (pH 7.5), 5 mM EDTA, 0.5 mM PMSF, 20 μg/ml of leupeptin, 4 μg/ml of E-64, and 0.5 μg/ml of pepstatin, and used as a membrane fraction.

Competitive binding and saturation binding experiments were performed as described by Ohtaki et al. (J. Biol. Chem., 268, 26650–26657, (1993)).

In brief, the membrane fractions were incubated in a buffer containing 20 mM Tris-HCl (pH 7.5), 0.05% CHAPS, 0.1% BSA, 5 mM EDTA, 0.5 mM of PMSF, 20 μg/ml of leupeptin, 4 μg/ml of E-64, and 0.5 μg/ml of pepstatin with porcine [$^{125}$I] galanin at 25° C. for 75 min. Bound and free ligands were separated by filtration through glass fiber filters (GF/F, Whatman, Kent, UK) treated with 0.3% of polyethylenimine. Nonspecific binding was determined in the presence of 1 μM of unlabeled porcine galanin. In competitive binding experiments the concentrations of galanin and galanin analogs were added to the buffer simultaneously with porcine [$^{125}$I] galanin.

CHO cells transformed with the expression plasmid for the mouse galanin receptor cDNA bound significant amounts of [$^{125}$I] galanin as compared with control cells (FIG. 15).

Membrane fractions (1 μg of protein) were incubated with concentrations of porcine [$^{125}$I] galanin for 75 min at 25° C. in Scatchard plot analysis. The results shown are from one representative experiment performed in triplicate assays.

Each symbol represents the mean value±S.E.M.

B, [$^{125}$I] galanin bound (pmol/mg protein), B/F, bound to free ratio (pmol/mg protein·nM).

Scatchard plot analysis indicated the presence of a single class of high-affinity binding site with a dissociation constant ($K_d$) of 45 pM and maximal number of binding sites ($B_{MAX}$) of 5 pmol/mg protein (FIG. 17).

Competitive experiments on the binding of porcine [$^{125}$I] galanin to mouse galanin receptor were conducted. Competitions to the porcine [$^{125}$I] galanin (100 pM at final concentrations) bindings were examined with unlabeled porcine (Δ), rat (●), human (■) galanins, galanin-(1–16) (○), and M15 (▼). Membrane fractions (1 μg of protein) were incubated with the ligands for 75 min at 25° C. The amounts of [$^{125}$I] galanin bound were expressed as percentages against the control. Each symbol represents the mean value±S.E.M. of the triplicate assays. IC$_{50}$ values were 0.25±0.03 nM (porcine galanin), 0.25±0.01 nM (rat galanin), 0.43±0.03 nM (human galanin), 0.83±0.01 nM (M15), and 3.6±0.04 nM [galanin-(1–16)], respectively.

The binding of [$^{125}$I] galanin was competitively inhibited by galanin and galanin-derived peptides. Porcine and rat galanin exhibited almost the same high efficiency in inhibiting the [$^{125}$I] galanin binding whereas human galanin was somewhat lower. The Ki values of porcine, rat, and human galanins were 0.072±0.008, 0.069±0.002, and 0.12±0.008 nM, respectively. The galanin receptor antagonists M15 and galanin-(1–16) also effectively inhibit the [$^{125}$I] galanin binding, and their Ki values were 0.23±0.003 and 1.0±0.011 nM, respectively (FIG. 18). These obtained values were almost comparable to those from MIN6 cell membranes.

(3) cAMP Assay

The CHO cells were seeded at 2.0×10$^5$ cells/well in 24-well tissue culture plates and cultured for two days. The cells were washed two times with HBSS containing 0.1% BSA and 1 mM IBMX, and then the same buffer with experimental agents were added to the wells. After incubation at 37° C. for 30 min, the media were discarded and intracellular cAMP was extracted with ice-cold ethanol. The aliquots of extracts were evaporated and the amounts of cAMP were quantitated by a cAMP EIA system (Amersham) as described by the manufacturer.

Galanin receptor-mediated inhibition of forskolin-stimulated cAMP production was observed. CHO-MGR20 or mock transformed CHO cells were incubated with forskolin (10 μM) and porcine galanin (0.1 μM) at 37° C. for 30 min. The reaction was terminated by extracting the cells with ice-cold ethanol. The amounts of intracellular cAMP were quantitated by EIA. Values indicated are mean±S.E.M. in triplicate assays.

It is examined by the assessment of galanin-induced signal transduction to confirm further that the mouse galanin receptor expressed in CHO cells was functional. The pancreatic galanin receptor has been demonstrated to induce the inhibition of insulin release through a pathway involving G proteins negatively coupled to adenylate cyclase (Cormont, M.,et al., Diabates, 40, 1170–1176, 1991; Gillison, S., et al., Diabates, 43, 24–32, 1994). The treatment with porcine galanin potently inhibited forskolin-stimulated CAMP accumulation in the galanin receptor cDNA-introduced CHO cells (FIG. 19). The CHO transformants with the plasmid vector without cDNA insert also showed forskolin-stimulated cAMP accumulation, but it was not inhibited by the galanin treatment. The treatment with galanin alone did not alter the cAMP levels in CHO transformants (FIG. 19).

The galanin receptor protein of the present invention and the DNA coding for said protein can be used for ① acquisition of antibody and antiserum; ② construction of expression system for of a recombinant type receptor protein; ③ development of the receptor binding assay system using said expression system and screening of the candidate compounds for pharmaceuticals; ④ conducting a drug design based upon a comparison with structurally analogous ligands and receptors; ⑤ preparation of probes and PCR primers for a gene diagnosis; ⑥ preparation of transgenic animals; and ⑦ preparation of model patient animals deficient in the receptor protein DNA. Elucidation of the structure and property of the mouse-derived galanin receptor is particularly related to the development of unique pharmaceuticals which act on such a system.

Furthermore, the human galanin receptor protein of the present invention is a novel protein having an amino acid sequence which is different from that of the known human galanin receptor protein. The cells (particularly CHO cells) retaining the expression vector containing the human galanin receptor of the present invention are capable of expressing far more amount of human galanin receptor protein than the known COS cells containing the human galanin receptor protein are.

The human galanin receptor protein of the present invention or partial peptide thereof or the cells containing the human galanin receptor protein or a cell membrane fraction thereof is capable of effectively screening the human galanin receptor agonist or antagonist.

When the screening method of the present invention is used, it is possible to advantageously select the agonist or the antagonist whereby pharmaceutical agents can be developed in earlier stage. The agonist is useful, for example, as an inhibitor for acetylcholine liberation, an inhibitor for insulin secretion, an inhibitor for a learning behavior or an inhibitor for satiety and also as a preventive and therapeutic agent for schizophrenic disease and as sedative while the antagonist is useful, for example, as an accelerator for acetylcholine liberation, an accelerator for insulin secretion, an inhibitor for growth hormone secretion, an accelerator for a learning behavior or as an accelerator for satiety and also as a preventive and therapeutic agent for diabetes, Alzheimer's disease and dementia.

What is claimed is:

1. An isolated galanin receptor protein comprising an amino acid sequence selected from the group consisting of SEQ ID NO:1, SEQ ID NO:2 and sufficient portion thereof possessing ligand binding activity or a salt thereof.

2. An isolated galanin receptor protein comprising an amino acid sequence of SEQ ID NO:5 or a salt thereof.

3. The receptor protein according to claim 1 or claim 2, which is produced by a transformed CHO cell.

4. An isolated DNA which comprises a nucleotide sequence coding for a galanin receptor protein comprising (i) an amino acid sequence selected from the group consisting of SEQ ID NO:1 and SEQ ID NO:2 or a sufficient portion thereof possessing ligand binding activity or (ii) an amino acid sequence of SEQ ID NO:5.

5. A DNA according to claim 4, comprising a nucleotide sequence of SEQ ID NO:3 or SEQ ID NO:4.

6. A DNA according to claim 4, comprising a nucleotide sequence of SEQ ID NO:6.

7. A vector comprising a DNA which comprises a nucleotide sequence coding for a galanin receptor protein comprising (i) an amino acid sequence selected from the group consisting of SEQ ID NO:1 and SEQ ID NO:2 or a sufficient portion thereof possessing ligand binding activity or (ii) an amino acid sequence of SEQ ID NO:5.

8. A transformed host cell culture or cell line comprising the vector comprising a DNA receptor comprising a nucleotide sequence coding for a galanin receptor protein comprising (i) an amino acid sequence selected from the group consisting of SEQ ID NO:1 and SEQ ID NO:2 or a sufficient portion thereof possessing galanin receptor activity or (ii) an amino acid sequence of SEQ ID NO:5.

9. The transformed host cell culture or cell line according to claim 8, wherein the host cell is a CHO cell.

10. The transformed host cell culture or cell line according to claim 8, wherein the host cell is 293 cell, CHO cell, Vero cell, L cell, myeloma cell, C127 cell, Balb/c3T3 cell or Sp-2/O cell.

11. The transformed host cell culture or cell line according to claim 8, which is CHO/pTS863-5 or CHO/pTS863-7.

12. A process for producing galanin receptor protein which comprises culturing the transformed host cell line or cell culture of claim 8, under conditions suitable to express said galanin receptor protein.

13. A kit for the screening of one or more agonists or antagonists to a galanin receptor protein according to claim 1, which comprises at least one component selected from the group consisting of a galanin receptor protein comprising an amino acid sequence selected from the group consisting of SEQ ID NO:1, SEQ ID NO:2, a sufficient portion of a galanin receptor protein comprising an amino acid sequence selected from the group consisting of SEQ ID NO:1 and SEQ ID NO:2 possessing ligand binding activity and a mixture of said receptor protein and sufficient portion.

14. A kit for the screening of one or more agonists or antagonists to a galanin receptor protein according to claim 2, which comprises a galanin receptor protein of SEQ ID NO:5 and a galanin.

\* \* \* \* \*

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
        (A) LENGTH:      128
        (B) TYPE:        Amino acid
        (C) TOPOLOGY:    Linear (ii) MOLECULE TYPE:    Peptide (xi) SEQUENCE DESCRIPTION:   SEQ ID NO: 1:

```
Ala Ala Met Ser Val Asp Arg Tyr Val Ala Ile Val His Ser Arg Arg
 1               5                  10                  15

Ser Ser Ser Leu Arg Val Ser Arg Asn Ala Leu Leu Gly Val Gly Phe
            20                  25                  30

Ile Trp Ala Leu Ser Ile Ala Met Ala Ser Pro Val Ala Tyr His Gln
        35                  40                  45

Arg Leu Phe His Arg Asp Ser Asn Gln Thr Phe Cys Trp Glu Gln Trp
    50                  55                  60

Pro Asn Lys Leu His Lys Lys Ala Tyr Val Val Cys Thr Phe Val Phe
65                  70                  75                  80

Gly Tyr Leu Leu Pro Leu Leu Leu Ile Cys Phe Cys Tyr Ala Lys Val
                85                  90                  95

Leu Asn His Leu His Lys Lys Leu Lys Asn Met Ser Lys Lys Ser Glu
                100                 105                 110

Ala Ser Lys Lys Lys Thr Ala Gln Thr Val Leu Val Val Val Val Val
                115                 120                 125
```

(2) INFORMATION FOR SEQ ID NO: 2:

(i) SEQUENCE CHARACTERISTICS:
        (A) LENGTH:      348
        (B) TYPE:        Amino acid
        (C) TOPOLOGY:    Linear (ii) MOLECULE TYPE:    Peptide (xi) SEQUENCE DESCRIPTION:   SEQ ID NO: 2:

```
Met Glu Leu Ala Met Val Asn Leu Ser Glu Gly Asn Gly Ser Asp Pro
 1               5                  10                  15

Glu Pro Pro Ala Pro Glu Ser Arg Pro Leu Phe Gly Ile Gly Val Glu
            20                  25                  30

Asn Phe Ile Thr Leu Val Val Phe Gly Leu Ile Phe Ala Met Gly Val
            35                  40                  45

Leu Gly Asn Ser Leu Val Ile Thr Val Leu Ala Arg Ser Lys Pro Gly
```

| | | | | | | | | | | | | | | |
|---|---|---|---|---|---|---|---|---|---|---|---|---|---|---|
| | | 50 | | | | 55 | | | | 60 | | | | |
| Lys | Pro | Arg | Ser | Thr | Thr | Asn | Leu | Phe | Ile | Leu | Asn | Leu | Ser | Ile | Ala |
| 65 | | | | 70 | | | | 75 | | | | 80 | | |

Lys Pro Arg Ser Thr Thr Asn Leu Phe Ile Leu Asn Leu Ser Ile Ala
65              70              75              80

Asp Leu Ala Tyr Leu leu Phe Cys Ile Pro Phe Gln Ala Thr Val Tyr
                85              90              95

Ala Leu Pro Thr Trp Val Leu Gly Ala Phe Ile Cys Lys Phe Ile His
            100             105             110

Tyr Phe Phe Thr Val Ser Met Leu Val Ser Ile Phe Thr Leu Ala Ala
            115             120             125

Met Ser Val Asp Arg Tyr Val Ala Ile Val His Ser Arg Arg Ser Ser
130             135             140

Ser Leu Arg Val Ser Arg Asn Ala Leu Leu Gly Val Gly Phe Ile Trp
145             150             155             160

Ala Leu Ser Ile Ala Met Ala Ser Pro Val Ala Tyr His Gln Arg Leu
            165             170             175

Phe His Arg Asp Ser Asn Gln Thr Phe Cys Trp Glu Gln Trp Pro Asn
            180             185             190

Lys Leu His Lys Lys Ala Tyr Val Val Cys Thr Phe Val Phe Gly Tyr
    195             200             205

Leu Leu Pro Leu Leu Leu Ile Cys Phe Cys Tyr Ala Lys Val Leu Asn
    210             215             220

His Leu His Lys Lys Leu Lys Asn Met Ser Lys Lys Ser Glu Ala Ser
225             230             235             240

Lys Lys Lys Thr Ala Gln Thr Val Leu Val Val Val Val Val Phe Gly
            245             250             255

Ile Ser Trp Leu Pro His His Val His Leu Trp Ala Glu Phe Gly
            260             265             270

Ala Phe Pro Leu Thr Pro Ala Ser Phe Phe Arg Ile Thr Ala His
            275             280             285

Cys Leu Ala Tyr Ser Asn Ser Ser Val Asn Pro Ile Ile Tyr Ala Phe
290             295             300

Leu Ser Glu Asn Phe Arg Lys Ala Tyr Lys Gln Val Phe Lys Cys His
305             310             315             320

Val Cys Asp Glu Ser Pro Arg Ser Glu Thr Lys Glu Asn Lys Ser Arg
            325             330             335

Met Asp Thr Pro Pro Ser Thr Asn Cys Thr His Val
            340             345

(2) INFORMATION FOR SEQ ID NO: 3:

(i) SEQUENCE CHARACTERISTICS:
        (A) LENGTH:      384
        (B) TYPE:        Nucleic acid
        (C) STRANDEDNESS: Double
        (D) TOPOLOGY:    Linear (ii) MOLECULE TYPE:   cDNA (ix) FEATURE:
        (C) IDENTIFICATION METHOD:   S (xi) SEQUENCE DESCRIPTION: SEQ ID NO: 3:

```
GCCGCGATGT CTGTGGATCG CTACGTGGCC ATTGTGCACT CGCGGCGCTC CTCCTCCCTC      60

AGGGTGTCCC GCAACGCACT GCTGGGCGTG GGCTTCATCT GGGCGCTGTC CATCGCCATG     120

GCCTCGCCGG TGGCCTACCA CCAGCGTCTT TTCCATCGGG ACAGCAACCA GACCTTCTGC     180

TGGGAGCAGT GGCCCAACAA GCTCCACAAG AAGGCTTACG TGGTGTGCAC TTTCGTCTTT     240
```

```
GGGTACCTTC TGCCCTTACT GCTCATCTGC TTTTGCTATG CCAAGGTCCT TAATCATCTG        300

CATAAAAAGC TGAAAAACAT GTCAAAAAAG TCTGAAGCAT CCAAGAAAAA GACTGCACAG        360

ACCGTCCTGG TGGTCGTTGT AGTA                                              384

(2) INFORMATION FOR SEQ ID NO: 4:

(i) SEQUENCE CHARACTERISTICS:
          (A) LENGTH:      1044
          (B) TYPE:        Nucleic acid
          (C) STRANDEDNESS: Double
          (D) TOPOLOGY:    Linear (ii) MOLECULE TYPE:   cDNA (ix) FEATURE:
          (C) IDENTIFICATION METHOD:   S (xi) SEQUENCE DESCRIPTION:  SEQ ID NO: 4:

ATGGAACTGG CTATGGTGAA CCTCAGTGAA GGGAATGGGA GCGACCCAGA GCCGCCAGCC         60

CCGGAGTCCA GGCCGCTCTT CGGCATTGGC GTGGAGAACT TCATTACGCT GGTAGTGTTT        120

GGCCTGATTT TCGCGATGGG CGTGCTGGGC AACAGCCTGG TGATCACCGT GCTGGCGCGC        180

AGCAAACCAG GCAACCCCCG CAGCACCACC AACCTGTTTA TCCTCAATCT GAGCATCGCA        240

GACCTGGCCT ACCTGCTCTT CTGCATCCCT TTTCAGGCCA CCGTGTATGC ACTGCCCACC        300

TGGGTGCTGG GCGCCTTCAT CTGCAAGTTT ATACACTACT TCTTCACCGT GTCCATGCTG        360

GTGAGCATCT TCACCCTGGC CGCGATGTCT GTGGATCGCT ACGTGGCCAT TGTGCACTCG        420

CGGCGCTCCT CCTCCCTCAG GGTGTCCCGC AACGCACTGC TGGGCGTGGG CTTCATCTGG        480

GCGCTGTCCA TCGCCATGGC CTCGCCGGTG GCCTACCACC AGCGTCTTTT CCATCGGGAC        540

AGCAACCAGA CCTTCTGCTG GGAGCAGTGG CCCAACAAGC TCCACAAGAA GGCTTACGTG        600

GTGTGCACTT TCGTCTTTGG GTACCTTCTG CCCTTACTGC TCATCTGCTT TTGCTATGCC        660

AAGGTCCTTA ATCATCTGCA TAAAAAGCTG AAAAACATGT CAAAAAAGTC TGAAGCATCC        720

AAGAAAAAGA CTGCACAGAC CGTCCTGGTG GTCGTTGTAG TATTTGGCAT ATCCTGGCTG        780

CCCCATCATG TCGTCCACCT CTGGGCTGAG TTTGGAGCCT TCCCACTGAC GCCAGCTTCC        840

TTCTTCTTCA GAATCACCGC CCATTGCCTG GCATACAGCA ACTCCTCAGT GAACCCCATC        900

ATATATGCCT TTCTCTCAGA AAACTTCCGG AAGGCGTACA AGCAAGTGTT CAAGTGTCAT        960

GTTTGCGATG AATCTCCACG CAGTGAAACT AAGGAAAACA AGAGCCGGAT GGACACCCCG       1020

CCATCCACCA ACTGCACCCA CGTG                                             1044

(2) INFORMATION FOR SEQ ID NO: 5:

(i) SEQUENCE CHARACTERISTICS:
          (A) LENGTH:      349
          (B) TYPE:        Amino acid
          (C) TOPOLOGY:    Linear (ii) MOLECULE TYPE:   Peptide (xi) SEQUENCE DESCRIPTION:  SEQ ID NO: 5:

Met Glu Leu Ala Val Gly Asn Leu Ser Glu Gly Asn Ala Ser Trp Pro
 1               5                  10                  15

Glu Pro Pro Ala Pro Glu Pro Gly Pro Leu Phe Gly Ile Gly Val Glu
                20                  25                  30

Asn Phe Val Thr Leu Val Val Phe Gly Leu Ile Phe Ala Leu Gly Val
            35                  40                  45
```

Leu Gly Asn Ser Leu Val Ile Thr Val Leu Ala Arg Ser Lys Pro Gly
                50                  55                  60

Lys Pro Arg Ser Thr Thr Asn Leu Phe Ile Leu Asn Leu Ser Ile Ala
 65                  70                  75                  80

Asp Leu Ala Tyr Leu Leu Phe Cys Ile Pro Phe Gln Ala Thr Val Tyr
                 85                  90                  95

Ala Leu Pro Thr Trp Val Leu Gly Ala Phe Ile Cys Lys Phe Ile His
                100                 105                 110

Tyr Phe Phe Thr Val Ser Met Leu Val Ser Ile Phe Thr Leu Ala Ala
                115                 120                 125

Met Ser Val Asp Arg Tyr Val Ala Ile Val His Ser Arg Arg Ser Ser
    130                 135                 140

Ser Leu Arg Val Ser Arg Asn Ala Leu Leu Gly Val Gly Cys Ile Trp
145                 150                 155                 160

Ala Leu Ser Ile Ala Met Ala Ser Pro Val Ala Tyr His Gln Gly Leu
                165                 170                 175

Phe His Pro Arg Ala Ser Asn Gln Thr Phe Cys Trp Glu Gln Trp Pro
                180                 185                 190

Asp Pro Arg His Lys Lys Ala Tyr Val Val Cys Thr Phe Val Phe Gly
                195                 200                 205

Tyr Leu Leu Pro Leu Leu Ile Cys Phe Cys Tyr Ala Lys Val Leu
                210                 215                 220

Asn His Leu His Lys Lys Leu Lys Asn Met Ser Lys Lys Ser Glu Ala
225                 230                 235                 240

Ser Lys Lys Lys Thr Ala Gln Thr Val Leu Val Val Val Val Val Phe
                245                 250                 255

Gly Ile Ser Trp Leu Pro His His Ile Ile His Leu Trp Ala Glu Phe
                260                 265                 270

Gly Val Phe Pro Leu Thr Pro Ala Ser Phe Leu Phe Arg Ile Thr Ala
                275                 280                 285

His Cys Leu Ala Tyr Ser Asn Ser Ser Val Asn Pro Ile Ile Tyr Ala
    290                 295                 300

Phe Leu Ser Glu Asn Phe Arg Lys Ala Tyr Lys Gln Val Phe Lys Cys
305                 310                 315                 320

His Ile Arg Lys Asp Ser His Leu Ser Asp Thr Lys Glu Asn Lys Ser
                325                 330                 335

Arg Ile Asp Thr Pro Pro Ser Thr Asn Cys Thr His Val
                340                 345

(2) INFORMATION FOR SEQ ID NO: 6:

(i) SEQUENCE CHARACTERISTICS:
        (A) LENGTH:      1047
        (B) TYPE:        Nucleic acid
        (C) STRANDEDNESS: Double
        (D) TOPOLOGY:    Linear (ii) MOLECULE TYPE:   cDNA (ix) FEATURE:
        (C) IDENTIFICATION METHOD:  S (xi) SEQUENCE DESCRIPTION: SEQ ID NO: 6:

ATGGAGCTGG CGGTCGGGAA CCTCAGCGAG GGCAACGCGA GCTGGCCGGA GCCCCCCGCC    60

CCGGAGCCCG GGCCGCTGTT CGGCATCGGC GTGGAGAACT TCGTCACGCT GGTGGTGTTC   120

GGCCTGATCT TCGCGCTGGG CGTGCTGGGC AACAGCCTAG TGATCACCGT GCTGGCGCGC   180

```
AGCAAGCCGG GCAAGCCGCG GAGCACCACC AACCTGTTCA TCCTCAACCT GAGCATCGCC      240

GACCTGGCCT ACCTGCTCTT CTGCATCCCC TTCCAGGCCA CCGTGTACGC GCTGCCCACC      300

TGGGTGCTGG GCGCCTTCAT CTGCAAGTTC ATCCACTACT TCTTCACCGT GTCCATGCTG      360

GTGAGCATCT TCACCCTGGC CGCGATGTCC GTGGACCGCT ACGTGGCCAT CGTGCACTCG      420

CGGCGCTCCT CCTCCCTCAG GGTGTCCCGC AACGCGCTGC TGGGCGTGGG CTGCATCTGG      480

GCGCTGTCCA TTGCCATGGC CTCGCCCGTG GCCTACCACC AGGGCCTCTT CCACCCGCGC      540

GCCAGCAACC AGACCTTCTG CTGGGAGCAG TGGCCCGACC CTCGCCACAA GAAGGCCTAC      600

GTGGTGTGCA CCTTCGTCTT CGGCTACCTG CTGCCGCTCC TGCTCATCTG CTTCTGCTAT      660

GCCAAGGTCC TTAATCACTT GCATAAAAAG TTGAAGAACA TGTCAAAGAA GTCTGAAGCA      720

TCCAAGAAAA AGACTGCACA GACAGTTCTG GTGGTGGTTG TGGTGTTTGG AATCTCCTGG      780

CTGCCGCACC ACATCATCCA TCTCTGGGCT GAGTTTGGAG TTTTCCCGCT GACGCCGGCT      840

TCCTTCCTCT TCAGAATCAC CGCCCACTGC CTGGCGTACA GCAATTCCTC CGTGAATCCT      900

ATCATTTATG CATTTCTCTC TGAAAATTTC AGGAAGGCCT ATAAACAAGT GTTCAAGTGT      960

CACATTCGCA AGATTCACA CCTGAGTGAT ACTAAAGAAA ATAAAAGTCG AATAGACACC      1020

CCACCATCAA CCAATTGTAC TCATGTG                                         1047
```

(2) INFORMATION FOR SEQ ID NO: 7:

(i) SEQUENCE CHARACTERISTICS:
    (A) LENGTH: 25
    (B) TYPE: Nucleic acid
    (C) STRANDEDNESS: Single
    (D) TOPOLOGY: Linear (ii) MOLECULE TYPE: Other nucleic acid
    Synthetic DNA (iii) FEATURE: N is A, G, C, or T (xi) SEQUENCE DESCRIPTION: SEQ ID NO: 7:

```
CGTGGSCMTS STGGGCAACN YCCTG                                             25
```

(2) INFORMATION FOR SEQ ID NO: 8:

(i) SEQUENCE CHARACTERISTICS:
    (A) LENGTH: 27
    (B) TYPE: Nucleic acid
    (C) STRANDEDNESS: Single
    (D) TOPOLOGY: Linear (ii) MOLECULE TYPE: Other nucleic acid
    Synthetic DNA (iii) FEATURE: N is A, G, C, or T (xi) SEQUENCE DESCRIPTION: SEQ ID NO: 8:

```
GTNGWRRGGC ANCCAGCAGA KGGCAAA                                           27
```

(2) INFORMATION FOR SEQ ID NO: 9:

(i) SEQUENCE CHARACTERISTICS:
    (A) LENGTH: 27
    (B) TYPE: Nucleic acid
    (C) STRANDEDNESS: Single
    (D) TOPOLOGY: Linear (ii) MOLECULE TYPE: Other nucleic acid
    Synthetic DNA (xi) SEQUENCE DESCRIPTION: SEQ ID NO: 9:

TCCGTGGACC GCTACGTGGC CATCGTG                                27

(2) INFORMATION FOR SEQ ID NO: 10:

(i) SEQUENCE CHARACTERISTICS:
        (A) LENGTH:       33
        (B) TYPE:         Nucleic acid
        (C) STRANDEDNESS: Single
        (D) TOPOLOGY:     Linear (ii) MOLECULE TYPE:   Other nucleic acid
        Synthetic DNA (xi) SEQUENCE DESCRIPTION: SEQ ID NO: 10:

GACTTATCAC ACATGAGTAC AATTGGTTGA TGG                          33

(2) INFORMATION FOR SEQ ID NO:11:

(i) SEQUENCE CHARACTERISTICS:
        (A) LENGTH: 1882 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 722...1768
        (D) OTHER INFORMATION:

(xi) SEQUENCE DESCRIPTION: SEQ ID NO:11:

```
CGCGGATTTC AGCCGAGCTG TTTTCGCCTC TCAGTTGCAG CAGAGAAGCC CCTGGCACCC    60

GACTCTATCC ACCACCAGGA AGCCTCCCAA AAGAGCTCTC GCCCTGTGGA CGACTCGGAA   120

TCCCTGGAAA AGCCGGGAGG GAGTCGGAGG CGCCAGCCCA CTGGGGAGGT GGCGCTGGGC   180

GCGCGGGATG CGCGGGGAGC CTTCTCTGCA GGAGCCGCAC AGTGCACTGC TGCGCGCTGG   240

GCAGTGCGGG GAAGCGCCGC GGGAAGGAGC GGCTCCGAGC AACAGGTGCA GCACGCAGCC   300

GCTCCGGGAG CCAGGGAAAA CCGCCGGCGA AGATCTGGAG CGGTAAGGCG GAGAGAAGGG   360

TCTTTCCACC TGCGCGGCTG CAGCCGGCGG ATCCCTCTTC CCAGGCTCCG TGGTCGCGCA   420

GCGGGCGGAG GCGCCCGGGC AGGGGACCCC CAGTGCTCTC GAGATCACCG TCCCTTCCCG   480

AGAAGGTCCA GCTCCGGGCT CCCGAACCCA CCCTCTCTCA GAAGGTCGCG GCGCAAAGAC   540

GGTGCCACCA GGCACGGCCA CCGGATCCCC GCTCCCGCTG GCTCGCGCCT CGGGGGAAGC   600

TCAGACTCCT AAACTCGCAC TCTCCGTGCT TTGCGCCGGG ACCCTGGCC ACCCCCGGCG   660

CCTGCTATCC CGCCCTCCCT CCCCGCGCGC CCCGCCGCTC GCCGGGACAG CCCCGCGGGC   720
```

```
C ATG GAG CTG GCG GTC GGG AAC CTC AGC GAG GGC AAC GCG AGC TGG CCG   769
  Met Glu Leu Ala Val Gly Asn Leu Ser Glu Gly Asn Ala Ser Trp Pro
  1               5                  10                  15

GAG CCC CCC GCC CCG GAG CCC GGG CCG CTG TTC GGC ATC GGC GTG GAG   817
Glu Pro Pro Ala Pro Glu Pro Gly Pro Leu Phe Gly Ile Gly Val Glu
                20                  25                  30

AAC TTC GTC ACG CTG GTG GTG TTC GGC CTG ATC TTC GCG CTG GGC GTG   865
Asn Phe Val Thr Leu Val Val Phe Gly Leu Ile Phe Ala Leu Gly Val
            35                  40                  45

CTG GGC AAC AGC CTA GTG ATC ACC GTG CTG GCG CGC AGC AAG CCG GGC   913
Leu Gly Asn Ser Leu Val Ile Thr Val Leu Ala Arg Ser Lys Pro Gly
        50                  55                  60

AAG CCG CGG AGC ACC ACC AAC CTG TTC ATC CTC AAC CTG AGC ATC GCC   961
Lys Pro Arg Ser Thr Thr Asn Leu Phe Ile Leu Asn Leu Ser Ile Ala
65                  70                  75                  80
```

```
GAC CTG GCC TAC CTG CTC TTC TGC ATC CCC TTC CAG GCC ACC GTG TAC     1009
Asp Leu Ala Tyr Leu Leu Phe Cys Ile Pro Phe Gln Ala Thr Val Tyr
                85                  90                  95

GCG CTG CCC ACC TGG GTG CTG GGC GCC TTC ATC TGC AAG TTC ATC CAC     1057
Ala Leu Pro Thr Trp Val Leu Gly Ala Phe Ile Cys Lys Phe Ile His
            100                 105                 110

TAC TTC TTC ACC GTG TCC ATG CTG GTG AGC ATC TTC ACC CTG GCC GCG     1105
Tyr Phe Phe Thr Val Ser Met Leu Val Ser Ile Phe Thr Leu Ala Ala
        115                 120                 125

ATG TCC GTG GAC CGC TAC GTG GCC ATC GTG CAC TCG CGG CGC TCC TCC     1153
Met Ser Val Asp Arg Tyr Val Ala Ile Val His Ser Arg Arg Ser Ser
    130                 135                 140

TCC CTC AGG GTG TCC CGC AAC GCG CTG CTG GGC GTG GGC TGC ATC TGG     1201
Ser Leu Arg Val Ser Arg Asn Ala Leu Leu Gly Val Gly Cys Ile Trp
145                 150                 155                 160

GCG CTG TCC ATT GCC ATG GCC TCG CCC GTG GCC TAC CAC CAG GGC CTC     1249
Ala Leu Ser Ile Ala Met Ala Ser Pro Val Ala Tyr His Gln Gly Leu
                165                 170                 175

TTC CAC CCG CGC GCC AGC AAC CAG ACC TTC TGC TGG GAG CAG TGG CCC     1297
Phe His Pro Arg Ala Ser Asn Gln Thr Phe Cys Trp Glu Gln Trp Pro
            180                 185                 190

GAC CCT CGC CAC AAG AAG GCC TAC GTG GTG TGC ACC TTC GTC TTC GGC     1345
Asp Pro Arg His Lys Lys Ala Tyr Val Val Cys Thr Phe Val Phe Gly
        195                 200                 205

TAC CTG CTG CCG CTC CTC ATC TGC TTC TGC TAT GCC AAG GTC CTT         1393
Tyr Leu Leu Pro Leu Leu Ile Cys Phe Cys Tyr Ala Lys Val Leu
    210                 215                 220

AAT CAC TTG CAT AAA AAG TTG AAG AAC ATG TCA AAG AAG TCT GAA GCA     1441
Asn His Leu His Lys Lys Leu Lys Asn Met Ser Lys Lys Ser Glu Ala
225                 230                 235                 240

TCC AAG AAA AAG ACT GCA CAG ACA GTT CTG GTG GTG GTT GTG GTG TTT     1489
Ser Lys Lys Lys Thr Ala Gln Thr Val Leu Val Val Val Val Val Phe
                245                 250                 255

GGA ATC TCC TGG CTG CCG CAC CAC ATC ATC CAT CTC TGG GCT GAG TTT     1537
Gly Ile Ser Trp Leu Pro His His Ile Ile His Leu Trp Ala Glu Phe
            260                 265                 270

GGA GTT TTC CCG CTG ACG CCG GCT TCC TTC CTC TTC AGA ATC ACC GCC     1585
Gly Val Phe Pro Leu Thr Pro Ala Ser Phe Leu Phe Arg Ile Thr Ala
        275                 280                 285

CAC TGC CTG GCG TAC AGC AAT TCC TCC GTG AAT CCT ATC ATT TAT GCA     1633
His Cys Leu Ala Tyr Ser Asn Ser Ser Val Asn Pro Ile Ile Tyr Ala
    290                 295                 300

TTT CTC TCT GAA AAT TTC AGG AAG GCC TAT AAA CAA GTG TTC AAG TGT     1681
Phe Leu Ser Glu Asn Phe Arg Lys Ala Tyr Lys Gln Val Phe Lys Cys
305                 310                 315                 320

CAC ATT CGC AAA GAT TCA CAC CTG AGT GAT ACT AAA GAA AAT AAA AGT     1729
His Ile Arg Lys Asp Ser His Leu Ser Asp Thr Lys Glu Asn Lys Ser
                325                 330                 335

CGA ATA GAC ACC CCA CCA TCA ACC AAT TGT ACT CAT GTG TGATAAAAGA TA   1780
Arg Ile Asp Thr Pro Pro Ser Thr Asn Cys Thr His Val
            340                 345

GAGTATCCTT ATGGTTGAGT TTCCATATAA GTGGACCAGA CACAGAAACA AACAGAATGA   1840

GCTAGTAAGC GATGCTGCAA CTTGTTATCT TAACAAGAAT TC                      1882

(2) INFORMATION FOR SEQ ID NO:12:

(i) SEQUENCE CHARACTERISTICS:
        (A) LENGTH: 145 amino acids
        (B) TYPE: amino acid
```

(C) STRANDEDNESS: single
            (D) TOPOLOGY: linear (ii) MOLECULE TYPE: None (xi) SEQUENCE DESCRIPTION: SEQ ID NO:12:

Val Gly Leu Val Gly Asn Phe Leu Ala Ala Met Ser Val Asp Arg Tyr
1               5                   10                  15

Val Ala Ile Val His Ser Arg Arg Ser Ser Leu Arg Val Ser Arg
            20              25                  30

Asn Ala Leu Leu Gly Val Gly Phe Ile Trp Ala Leu Ser Ile Ala Met
            35              40                  45

Ala Ser Pro Val Ala Tyr His Gln Arg Leu Phe His Arg Asp Ser Asn
50              55                  60

Gln Thr Phe Cys Trp Glu Gln Trp Pro Asn Lys Leu His Lys Lys Ala
65              70                  75                  80

Tyr Val Val Cys Thr Phe Val Phe Gly Tyr Leu Leu Pro Leu Leu Leu
                85                  90                  95

Ile Cys Phe Cys Tyr Ala Lys Val Leu Asn His Leu His Lys Lys Leu
                100                 105                 110

Lys Asn Met Ser Lys Lys Ser Glu Ala Ser Lys Lys Lys Thr Ala Gln
            115                 120                 125

Thr Val Leu Val Val Val Val Phe Ala Leu Cys Trp Leu Pro Phe
    130                 135                 140

Tyr
145

(2) INFORMATION FOR SEQ ID NO:13:

(i) SEQUENCE CHARACTERISTICS:
        (A) LENGTH: 147 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:13:

Met Phe Thr Ser Val Phe Cys Leu Thr Val Leu Ser Val Asp Arg Tyr
1               5                   10                  15

Val Ala Val Val His Pro Leu Arg Ala Ala Thr Tyr Arg Arg Pro Ser
            20                  25                  30

Val Ala Lys Leu Ile Asn Leu Gly Val Trp Leu Ala Ser Leu Leu Val
            35                  40                  45

Thr Leu Pro Ile Ala Ile Phe Ala Asp Thr Arg Pro Ala Arg Gly Gly
50                  55                  60

Gln Ala Val Ala Cys Asn Leu Gln Trp Pro His Pro Ala Trp Ser Ala
65                  70                  75                  80

Val Phe Val Val Tyr Thr Phe Leu Leu Gly Phe Leu Leu Pro Val Leu
                85                  90                  95

Ala Ile Gly Leu Cys Tyr Leu Leu Ile Val Gly Lys Met Arg Ala Val
                100                 105                 110

Ala Leu Arg Ala Gly Trp Gln Gln Arg Arg Ser Glu Lys Lys Ile
            115                 120                 125

Thr Arg Leu Val Leu Met Val Val Val Phe Val Leu Cys Trp Met
    130                 135                 140

Pro Phe Tyr
145

(2) INFORMATION FOR SEQ ID NO:14:

(i) SEQUENCE CHARACTERISTICS:
        (A) LENGTH: 148 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:14:

```
Gln Phe Thr Ser Ile Phe Cys Leu Thr Val Met Ser Ile Asp Arg Tyr
 1               5                  10                  15

Leu Ala Val Val His Pro Ile Lys Ser Ala Lys Trp Arg Arg Pro Arg
            20                  25                  30

Thr Ala Lys Met Ile Thr Met Ala Val Trp Gly Val Ser Leu Leu Val
        35                  40                  45

Ile Leu Pro Ile Met Ile Tyr Ala Gly Leu Arg Ser Asn Gln Trp Gly
50                  55                  60

Arg Ser Ser Cys Thr Ile Asn Trp Pro Gly Glu Ser Gly Ala Trp Tyr
65                  70                  75                  80

Thr Gly Phe Ile Ile Tyr Thr Phe Ile Leu Gly Phe Leu Val Pro Leu
                85                  90                  95

Thr Ile Ile Cys Leu Cys Tyr Leu Phe Ile Ile Lys Val Lys Ser
            100                 105                 110

Ser Gly Ile Arg Val Gly Ser Ser Lys Arg Lys Lys Ser Glu Lys Lys
            115                 120                 125

Val Thr Arg Met Val Ser Ile Val Val Ala Asx Phe Ile Phe Cys Trp
        130                 135                 140

Leu Pro Phe Tyr
145
```

(2) INFORMATION FOR SEQ ID NO:15:

(i) SEQUENCE CHARACTERISTICS:
        (A) LENGTH: 148 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:15:

```
Met Phe Thr Ser Ile Tyr Cys Leu Thr Val Leu Ser Val Asp Arg Tyr
 1               5                  10                  15

Val Ala Val Val His Pro Ile Lys Ala Ala Arg Tyr Arg Arg Pro Thr
            20                  25                  30

Val Ala Lys Val Val Asn Leu Gly Val Trp Val Leu Ser Leu Leu Val
        35                  40                  45

Ile Leu Pro Ile Val Val Phe Ser Arg Thr Ala Ala Asn Ser Asp Gly
50                  55                  60

Thr Val Ala Cys Asn Met Leu Met Pro Glu Pro Ala Gln Arg Trp Leu
65                  70                  75                  80

Val Gly Phe Val Leu Thr Tyr Phe Leu Met Gly Phe Leu Leu Pro Val
                85                  90                  95

Gly Ala Ile Cys Leu Cys Tyr Cys Leu Ile Ile Ala Lys Met Arg Met
            100                 105                 110

Val Ala Leu Lys Ala Gly Trp Gln Gln Arg Lys Arg Ser Glu Arg Lys
```

```
                115                 120                125
Ile Thr Leu Met Val Met Met Val Val Met Val Phe Val Ile Cys Trp
        130                 135                140

Met Pro Phe Tyr
145
```

(2) INFORMATION FOR SEQ ID NO:16:

(i) SEQUENCE CHARACTERISTICS:
        (A) LENGTH: 436 base pairs
        (B) TYPE: nucleic acid
        (C) STRANDEDNESS: single
        (D) TOPOLOGY: linear (xi) SEQUENCE DESCRIPTION: SEQ ID NO:16:

```
GTGGGCCTGG TGGGCAACTT CCTGGCCGCG ATGTCTCGTG CATCGCTACG TGGCCATTGT      60

GCACTCGCGG CGCTCCTCCT CCCTCAGGGT GTCCCGCAAC GCACTGCTGG GCGTGGGCTT     120

CATCTGGGCG CTGTCCATCG CCATGGCCTC GCCGGTGGCC TACCACCAGC GTCTTTTCCA     180

TCGGGACAGC AACCAGACCT TCTGCTGGGA GCAGTGGCCC AACAAGCTCC ACAAGAAGGC     240

TTACGTGGTG TGCACTTTCG TCTTTGGGTA CCTTCTGCCC TTACTGCTCA TCTGCTTTTG     300

CTATGCCAAG GTCCTTAATC ATCTGCATAA AAAGCTGAAA AACATGTCAA AAAAGTCTGA     360

AGCATCCAAG AAAAAGACTG CACAGACCGT CCTGGTGGTC GTTGTAGTAT TTGCCCTCTG     420

CTGGCTGCCT TTCTAC                                                     436
```

(2) INFORMATION FOR SEQ ID NO:17:

(i) SEQUENCE CHARACTERISTICS:
        (A) LENGTH: 1607 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 484...1524
        (D) OTHER INFORMATION:

(xi) SEQUENCE DESCRIPTION: SEQ ID NO:17:

```
ATGGAACTGG CTATGGTGAA CCTCAGTGAA GGGAATGGGA GCGACCCAGA GCCGCCAGCC      60

CCGGAGTCCA GGCCGCTCTT CGGCATTGGC GTGGAGAACT TCATTACGCT GGTAGTGTTT     120

GGCCTGATTT TCGCGATGGG CGTGCTGGGC AACAGCCTGG TGATCACCGT GCTGGCGCGC     180

AGCAAACCAG GCAACCCCCG CAGCACCACC AACCTGTTTA TCCTCAATCT GAGCATCGCA     240

GACCTGGCCT ACCTGCTCTT CTGCATCCCT TTTCAGGCCA CCGTGTATGC ACTGCCCACC     300

TGGGTGCTGG GCGCCTTCAT CTGCAAGTTT ATACACTACT TCTTCACCGT GTCCATGCTG     360

CTGTCCTGGG CCACTCCGTG ATCCTAGGCT ACCTCCAGAG CCAGTTTTCC CTGGCTGGCA     420

CAACTCTCCA GGGCGCTCCG GTCCGTTGCA CAGCGCCCCA AGGGGGTATC CCAGTAAGTG     480

ATG GAA CTG GCT ATG GTG AAC CTC AGT GAA GGG AAT GGG AGC GAC CCA        528
Met Glu Leu Ala Met Val Asn Leu Ser Glu Gly Asn Gly Ser Asp Pro
 1               5                  10                  15

GAG CCG CCA GCC CCG GAG TCC AGG CCG CTC TTC GGC ATT GGC GTG GAG        576
Glu Pro Pro Ala Pro Glu Ser Arg Pro Leu Phe Gly Ile Gly Val Glu
                20                  25                  30

AAC TTC ATT ACG CTG GTA GTG TTT GGC CTG ATT TTC GCG ATG GGC GTG        624
Asn Phe Ile Thr Leu Val Val Phe Gly Leu Ile Phe Ala Met Gly Val
                35                  40                  45
```

```
CTG GGC AAC AGC CTG GTG ATC ACC GTG CTG GCG CGC AGC AAA CCA GGC      672
Leu Gly Asn Ser Leu Val Ile Thr Val Leu Ala Arg Ser Lys Pro Gly
            50                  55                  60

AAG CCG CGC AGC ACC ACC AAC CTG TTT ATC CTC AAT CTG AGC ATC GCA      720
Lys Pro Arg Ser Thr Thr Asn Leu Phe Ile Leu Asn Leu Ser Ile Ala
 65                  70                  75

GAC CTG GCC TAC CTG CTC TTC TGC ATC CCT TTT CAG GCC ACC GTG TAT      768
Asp Leu Ala Tyr Leu Leu Phe Cys Ile Pro Phe Gln Ala Thr Val Tyr
 80                  85                  90                  95

GCA CTG CCC ACC TGG GTG CTG GGC GCC TTC ATC TGC AAG TTT ATA CAC      816
Ala Leu Pro Thr Trp Val Leu Gly Ala Phe Ile Cys Lys Phe Ile His
                100                 105                 110

TAC TTC TTC ACC GTG TCC ATG CTG GTG AGC ATC TTC ACC CTG GCC GCG      864
Tyr Phe Phe Thr Val Ser Met Leu Val Ser Ile Phe Thr Leu Ala Ala
            115                 120                 125

ATG TCT GTG GAT CGC TAC GTG GCC ATT GTG CAC TCG CGG CGC TCC TCC      912
Met Ser Val Asp Arg Tyr Val Ala Ile Val His Ser Arg Arg Ser Ser
                130                 135                 140

TCC CTC AGG GTG TCC CGC AAC GCA CTG CTG GGC GTG GGC TTC ATC TGG      960
Ser Leu Arg Val Ser Arg Asn Ala Leu Leu Gly Val Gly Phe Ile Trp
            145                 150                 155

GCG CTG TCC ATC GCC ATG GCC TCG CCG GTG GCC TAC CAC CAG CGT CTT     1008
Ala Leu Ser Ile Ala Met Ala Ser Pro Val Ala Tyr His Gln Arg Leu
160                 165                 170                 175

TTC CAT CGG GAC AGC AAC CAG ACC TTC TGC TGG GAG CAG TGG CCC AAC     1056
Phe His Arg Asp Ser Asn Gln Thr Phe Cys Trp Glu Gln Trp Pro Asn
                180                 185                 190

AAG CTC CAC AAG AAG GCT TAC GTG GTG TGC ACT TTC GTC TTT GGG TAC     1104
Lys Leu His Lys Lys Ala Tyr Val Val Cys Thr Phe Val Phe Gly Tyr
            195                 200                 205

CTT CTG CCC TTA CTG CTC ATC TGC TTT TGC TAT GCC AAG GTC CTT AAT     1152
Leu Leu Pro Leu Leu Leu Ile Cys Phe Cys Tyr Ala Lys Val Leu Asn
                210                 215                 220

CAT CTG CAT AAA AAG CTG AAA AAC ATG TCA AAA AAG TCT GAA GCA TCC     1200
His Leu His Lys Lys Leu Lys Asn Met Ser Lys Lys Ser Glu Ala Ser
            225                 230                 235

AAG AAA AAG ACT GCA CAG ACC GTC CTG GTG GTC GTT GTA GTA TTT GGC     1248
Lys Lys Lys Thr Ala Gln Thr Val Leu Val Val Val Val Val Phe Gly
240                 245                 250                 255

ATA TCC TGG CTG CCC CAT CAT GTC GTC CAC CTC TGG GCT GAG TTT GGA     1296
Ile Ser Trp Leu Pro His His Val Val His Leu Trp Ala Glu Phe Gly
                260                 265                 270

GCC TTC CCA CTG ACG CCA GCT TCC TTC TTC TTC AGA ATC ACC GCC CAT     1344
Ala Phe Pro Leu Thr Pro Ala Ser Phe Phe Phe Arg Ile Thr Ala His
            275                 280                 285

TGC CTG GCA TAC AGC AAC TCC TCA GTG AAC CCC ATC ATA TAT GCC TTT     1392
Cys Leu Ala Tyr Ser Asn Ser Ser Val Asn Pro Ile Ile Tyr Ala Phe
            290                 295                 300

CTC TCA GAA AAC TTC CGG AAG GCG TAC AAG CAA GTG TTC AAG TGT CAT     1440
Leu Ser Glu Asn Phe Arg Lys Ala Tyr Lys Gln Val Phe Lys Cys His
            305                 310                 315

GTT TGC GAT GAA TCT CCA CGC AGT GAA ACT AAG GAA AAC AAG AGC CGG     1488
Val Cys Asp Glu Ser Pro Arg Ser Glu Thr Lys Glu Asn Lys Ser Arg
320                 325                 330                 335

ATG GAC ACC CCG CCA TCC ACC AAC TGC ACC CAC GTG TGAAGGTTTG CGGGAG   1540
Met Asp Thr Pro Pro Ser Thr Asn Cys Thr His Val
                340                 345
```

-continued

```
CCTCCCGACT TCCAGCTCCC ATGTGTGTTA GAGAGAGGAG GGCGGAGCGA ATTATCAAGT   1600

AACATGG                                                              1607
```